(12) United States Patent
Altenburger et al.

(10) Patent No.: US 8,541,455 B2
(45) Date of Patent: Sep. 24, 2013

(54) DERIVATIVES OF 2-PYRIDIN-2-YL-PYRAZOL-3(2H)-ONE, PREPARATION AND THERAPEUTIC USE THEREOF AS HIF ACTIVATORS

(75) Inventors: Jean-Michel Altenburger, Paris (FR); Valérie Fossey, Paris (FR); Stéphane Illiano, Paris (FR); Géraldine Manette, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/172,305

(22) Filed: Jun. 29, 2011

(65) Prior Publication Data
US 2011/0294788 A1 Dec. 1, 2011

Related U.S. Application Data

(63) Continuation of application No. PCT/FR2009/052691, filed on Dec. 24, 2009.

(30) Foreign Application Priority Data

Dec. 29, 2008 (FR) ...................................... 08 07474
Aug. 28, 2009 (FR) ...................................... 09 04092

(51) Int. Cl.
*A61K 31/4439* (2006.01)
*C07D 401/04* (2006.01)

(52) U.S. Cl.
USPC ....................................... 514/341; 546/276.1

(58) Field of Classification Search
USPC ....................................... 546/276.1; 514/341
See application file for complete search history.

(56) References Cited

U.S. PATENT DOCUMENTS

| 5,175,176 | A | * | 12/1992 | Sasse et al. ................... 514/341 |
| 5,750,088 | A | | 5/1998 | Sworin et al. |
| 2005/0187276 | A1 | | 8/2005 | Park et al. |
| 2010/0035906 | A1 | | 2/2010 | Flamme et al. |
| 2010/0305085 | A1 | | 12/2010 | Thede et al. |

FOREIGN PATENT DOCUMENTS

| EP | 0469357 | 2/1992 |
| WO | WO 2006/114213 | 11/2006 |
| WO | WO 2007/103905 | 9/2007 |
| WO | WO 2008/047198 | 4/2008 |
| WO | WO 2008/067871 | 6/2008 |
| WO | WO 2008/141731 | 11/2008 |

OTHER PUBLICATIONS

U.S. Appl. No. 13/172,321, filed Jun. 29, 2011, Altenburger, et al.
Eglen, R. M., et al., Enzyme Fragment Complementation: A Flexible High Throughput Screening Assay Technology, Assay and Drug Development Technology, vol. 1, No. 1, (2002), pp. 97-104.
Bonjoch, J., et al., Synthesis of 2,5-piperidinediones. Regioselectivity in the Dieckmann Cyclization, Tetrahedron, vol. 40, No. 13, pp. 2505-2511, (1984).
Buechi, J., et al., Synthesis and Pharmacological Properties of Certain Pyridylpyrazol-5-Ones, Helvetica Chimica Acta, (1966), vol. 49, No. 1, pp. 272-280.
Conroy, et al., Using the Electrostatic Field Effect to Design a New Class of Inhibitors for Cysteine Proteases, J. Am. Chem. Soc., (1997), vol. 119, pp. 4285-4291.
Eglen, R. M., et al., B Galactosidase Enzyme Fragment Complementation as A Novel Technology for High Throughput Screening, Combinatorial Chemistry & High Throughput Screen, vol. 6, pp. 381-387, (2003).
International Search Report for WO2010/076524 dated Jul. 8, 2010.

* cited by examiner

*Primary Examiner* — Patricia L Morris
(74) *Attorney, Agent, or Firm* — Jiang Lin

(57) ABSTRACT

The present invention relates to novel substituted dihydropyrazolone derivatives, to their preparation and to their therapeutic use as activators of the transcription factor HIF.

10 Claims, No Drawings

DERIVATIVES OF 2-PYRIDIN-2-YL-PYRAZOL-3(2H)-ONE, PREPARATION AND THERAPEUTIC USE THEREOF AS HIF ACTIVATORS

This application is a Continuation of International Application No. PCT/FR2009/052691, filed Dec. 24, 2009, which is incorporated herein by reference in its entirety.

The present invention relates to novel substituted dihydropyrazolone derivatives, to their preparation and to their therapeutic use as activators of the transcription factor HIF.

Hypoxia-inducible factor (HIF) (HIF1α) is a transcription factor that is constitutively expressed in all tissues. This protein was discovered in 1994 by Gregg Semenza during studies on the regulatory sequences of the EPO gene. He identified a sequence located in the non-coding 3' position in the EPO promoter, which bears the name "hypoxia response element" (HRE) and which is a site of binding of the protein HIF1α allowing transcriptional activation of EPO. Thereafter, the HRE sequence was also located on more than 70 other genes, such as VEGF (vascular endothelial growth factor) or Glut1 (glucose transporter 1). The transcriptional complex HIF-1 is at the minimum a heterodimer formed from the protein HIF1α or HIF2α and another transcription factor ARNT (formerly known as HIF1β). ARNT is constitutively and stably expressed in cells and the main part of the transcription complex regulation is associated with the amount of HIF1α present in the cells, which is thus the limiting factor.

Under normal oxygen conditions, the protein HIF1α is rapidly degraded (half-life of 5 minutes). This degradation follows the hydroxylation of HIF1α or HIF2α, respectively, on prolines 402 and 563 and prolines 405 and 531 for the human forms with HIF prolyl hydroxylase (HIF-PHDs or EGLNs). This hydroxylation allows binding of the Von Hippell Lindau protein (pVHL) associated with a ubiquitin ligase, which results in the degradation of HIF1α or HIF2α by the ubiquitin proteasome system. When the cell or tissue are subjected to high hypoxia/ischaemia, HIF1α or HIF2α is no longer degraded by the ubiquitin-proteasome system and can then combine with the other transcription factors of the HIF complex to transfer into the nucleus and activate their target genes.

Although high hypoxia is the main cause of activation of the proteins HIF1α and HIF2α, other inducers, such as insulin and growth factors, may also play a role in their stabilization, especially via phosphorylation on their serines 641 and 643.

Phenotypic screening directed towards measuring the stabilization of the protein HIF1α and/or HIF2α was thus established to identify the compounds of the present invention.

The compounds according to the present invention correspond to formula (I) below:

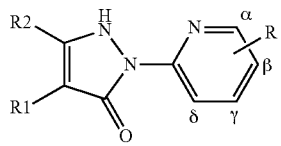

in which

R represents a group —SO$_2$—NR3R4, a hydrogen atom, a halogen atom, a group -halo(C1-C5)alkyl, a group —CO$_2$R5 or a group —SO$_2$—R4; R3, R4 and R5 being as defined below;

R1 represents a heterocycloalkyl group not containing a nitrogen atom, a group —W—(C3-C6)cycloalkyl, a group —W-aryl, a group —W-heteroaryl, a group —W-heterocycloalkyl, a group —W—COOR5 or a group —W—CONR5R6, (i) the said aryl, heteroaryl and heterocycloalkyl groups being optionally substituted on at least one carbon atom with at least one substituent chosen from halogen atoms, groups (C1-C5)alkyl, groups —(C1-C5)alkylene-O—(C1-C5)alkyl, groups —(C1-C5)alkoxy, a hydroxyl function, groups -halo(C1-C5)alkyl, a cyano function, groups —O(C1-C5)alkylene-O—(C1-C5)alkyl, groups —O—(C1-C5)alkylene-NR5R6, groups —SO$_2$—(C1-C5)alkyl, groups —NR5R6 and groups —CO$_2$R5, and (ii) it being understood that when it is a heterocycloalkyl group, the said group comprising at least one nitrogen atom, this atom may optionally bear a substituent chosen from groups (C1-C5)alkyl, R2 represents a hydrogen atom, a group —(C1-C5)alkyl, a group —(C1-C5)alkylene-O—(C1-C5)alkyl, a group -halo(C1-C5)alkyl, a group —W—COOR5, a group —W—C(O)NHR5 or a group —W—C(O)—NR5R6;

W, R5 and R6 being as defined below;

it being understood that:

n represents 0, 1 or 2;

W is
(i) a group —(C1-C5)alkylene-, optionally substituted with a group chosen from groups —(CH$_2$)n—CO$_2$R5 and groups —(CH$_2$)n—(CO)NR5R6, with n as defined above and R5 and R6 as defined below; or
(ii) a group —(C3-C6)cycloalkylene-, R3 and R4
(i) which may be identical or different, represent, independently of each other, a hydrogen atom, a group —(C1-C5)alkyl, a group —(C3-C6)cycloalkyl, a group —(C1-C5)alkylene-O—(C1-C5)alkyl, an aryl, a group —CH$_2$-aryl, a heteroaryl, a heterocycloalkyl, a group —W—OH, a group —W—CHOH—CH$_2$OH, a group —W—CO$_2$R5, a group —W—NR5R6 or a group —W—O—(CH$_2$)n-aryl;

the said groups —(C3-C6)cycloalkyl and heterocycloalkyl being optionally substituted
on at least one carbon atom with at least one group chosen from —(C1-C5)alkyl, a group —(C1-C5)alkoxy, a hydroxyl function, a group —W—NR5R6 and a group —W—CO$_2$R5, in the case of the groups —(C3-C6)cycloalkyl and heterocycloalkyl and/or
on at least one heteroatom chosen from nitrogen with at least one group chosen from —(C1-C5)alkyl in the case of a heterocycloalkyl group, with W and n as defined previously and R5 and R6 as defined below and it being understood that when R3 and R4 are identical, they cannot be a hydrogen atom;

(ii) or alternatively R3 and R4 form, together with the nitrogen atom that bears them, a heterocycloalkyl group, optionally substituted on at least one carbon atom and/or, where appropriate, on at least one heteroatom, with at least one substituent chosen from groups —(C1-C5)alkyl and groups —CH$_2$-aryl;

R5 and R6, which may be identical or different, represent, independently of each other, a hydrogen atom, a group —(C1-C5)alkyl or a group —(C1-C5)haloalkyl, with the exclusion of the following compounds:
4-benzyl-2-(pyridin-2-yl)-1,2-dihydro-3H-pyrazol-3-one
4-(2,4-dichlorobenzyl)-2-(pyridin-2-yl)-1,2-dihydro-3H-pyrazol-3-one
4-(4-methoxybenzyl)-2-(pyridin-2-yl)-1,2-dihydro-3H-pyrazol-3-one
4-(4-bromobenzyl)-2-(pyridin-2-yl)-1,2-dihydro-3H-pyrazol-3-one
2-(pyridin-2-yl)-4-[2-(trifluoromethyl)benzyl]-1,2-dihydro-3H-pyrazol-3-one
4-(4-chlorobenzyl)-2-(pyridin-2-yl)-1,2-dihydro-3H-pyrazol-3-one
4-(1,3-benzodioxol-5-ylmethyl)-2-(pyridin-2-yl)-1,2-dihydro-3H-pyrazol-3-one
4-(3-methylbenzyl)-2-(pyridin-2-yl)-1,2-dihydro-3H-pyrazol-3-one
4-(2-chlorobenzyl)-2-(pyridin-2-yl)-1,2-dihydro-3H-pyrazol-3-one
4-(4-methylbenzyl)-2-(pyridin-2-yl)-1,2-dihydro-3H-pyrazol-3-one
4-(3-chlorobenzyl)-2-(pyridin-2-yl)-1,2-dihydro-3H-pyrazol-3-one
4-(4-tert-butylbenzyl)-2-(pyridin-2-yl)-1,2-dihydro-3H-pyrazol-3-one
4-benzyl-5-methyl-2-(pyridin-2-yl)-1,2-dihydro-3H-pyrazol-3-one
5-methyl-4-(1-phenylethyl)-2-(pyridin-2-yl)-1,2-dihydro-3H-pyrazol-3-one
4-benzyl-2-(6-chloropyridin-2-yl)-5-methyl-1,2-dihydro-3H-pyrazol-3-one
4-{1-[4-(diethylamino)phenyl]ethyl}-5-methyl-2-(pyridin-2-yl)-1,2-dihydro-3H-pyrazol-3-one.

The compounds of formula (I) may exist in the form of bases or salts, the compounds of formula (I) having in this case been salified with acids or bases, especially pharmaceutically acceptable acids or bases. They are then referred to as addition salts, which form part of the invention.

These salts are advantageously prepared with pharmaceutically acceptable acids, but the salts of other acids that are useful, for example, for purifying or isolating the compounds of formula (I) also form part of the invention.

The compounds of formula (I) may also exist in the form of hydrates or solvates, namely in the form of associations or combinations with one or more water molecules or with a solvent. Such hydrates and solvates also form part of the invention.

The various tautomeric forms of the compounds of formula (I) also form part of the invention.

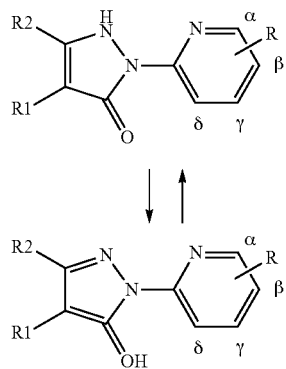

Furthermore, a subject of the invention is also a uniform test process for the direct measurement by beta-galactosidase complementation of the amount of HIF1-alpha protein in the nucleus of cells, preferably HEK cells, after treating the said cells with one or more test compounds, which consists in:
(a) inoculating, preferably in 384-well plates, the said cells in a suitable culture medium, preferably 1% foetal calf serum (abbreviated as FCS);
(b) adding the test compound(s) at a suitable concentration in a suitable solvent to the cells previously inoculated in the said culture medium; preferably the test compounds are diluted in 0.1% FCS;
(c) incubating the said cells thus prepared in an indicator at about 37° C., advantageously for about 6 hours;
(d) lysing the cells with a lysis buffer containing a chemiluminescent substrate for beta-galactosidase;
(e) incubating in the absence of light, before reading and measuring the luminescence, which is a function of the beta-galactosidase activity.

The compounds according to the invention underwent a screening test according to the test as defined above.

In the context of the present invention, and unless otherwise mentioned in the text, the following definitions apply:
a halogen atom: a fluorine, chlorine, bromine or iodine atom;
an alkyl group: a linear or branched, saturated aliphatic group, which may contain 1, 2, 3, 4 or 5 carbon atoms (abbreviated as —(C1-C5)alkyl). Examples that may be mentioned include, as (i) group —C1alkyl, the methyl group, as (ii) group —C2alkyl, the ethyl group, as (iii) group —C3alkyl, the propyl or isopropyl group, as (iv) group —C4alkyl, the butyl, isobutyl or tert-butyl group, as (v) group —C5alkyl the pentyl or isopentyl group;
an alkylene group: a linear or branched, saturated divalent alkyl group as defined previously, which may contain 1, 2, 3, 4 or 5 carbon atoms (abbreviated as —(C1-C5)alkylene-). Examples that may be mentioned include methylene (or —CH$_2$—), ethylene (or —CH$_2$—CH$_2$—) or propylene (—CH$_2$—CH$_2$—CH$_2$— or —C(CH$_3$)$_2$—) groups;
a cycloalkyl group: a cyclic alkyl group which may contain 3, 4, 5 or 6 carbon atoms, also abbreviated as —(C3-C6)cycloalkyl. Examples that may be mentioned include cyclopropyl, cyclobutyl, cyclopentyl and cyclohexyl groups;
a cycloalkylene groups: a saturated divalent cycloalkyl group, as defined previously, which may contain 3, 4, 5 or 6 carbon atoms and which is then abbreviated as —(C3-C6)cycloalkylene-. Examples that may be mentioned include the radicals -cyclopropylene-, -cyclobutylene-, -cyclopentylene- and -cyclohexylene-;
an alkoxy group: a radical —O-alkyl in which the alkyl group is as defined previously. Examples that may be mentioned include the groups —O—(C1-C5)alkyl or —(C1-C5)alkoxy, and in particular, as (i) group —O—C1alkyl, the group —Omethyl, as (ii) group —O—C2alkyl, the group —Oethyl, as (iii) group —O—C3alkyl, the group —Opropyl or —Oisopropyl, as (iv) group —O—C4alkyl, the group —Obutyl, —Oisobutyl or —Otert-butyl, as (v) group —O—C5alkyl the group —Opentyl or —Oisopentyl;
an alkoxy-alkyl group: a radical of formula -alkylene-O-alkyl, in which the alkyl and alkylene groups, comprising the same number of carbon atoms or not comprising the same number of carbon atoms, are as defined previously. Examples that may be mentioned include groups —(C1-C5)alkylene-O—(C1-C5)alkyl, with —(C1-C5) alkylene- and —(C1-C5)alkyl as defined above;

an alkoxy-alkoxy group: a radical of formula —O-alkylene-O-alkyl, in which the alkylene and alkyl groups, comprising the same number of carbons or not comprising the same number of carbons, are as defined previously;

a haloalkyl group: an alkyl group as defined above, substituted with 1, 2, 3, 4 or 5 halogen atoms, as defined previously. Examples that will be mentioned include groups -halo(C1-C5)alkyl, with (C1-C5)alkyl as defined above, for instance the trifluoromethyl group (abbreviated as —CF$_3$) or the group —CH$_2$—CF$_3$;

an aryl group: a cyclic aromatic group containing 5 or 6 carbon atoms. An example of aryl groups that may be mentioned is the phenyl group;

a heteroaryl group: a cyclic aromatic group containing 2, 3, 4 or 5 carbon atoms and comprising 1 to 3 heteroatoms, which can be chosen from the nitrogen atom, the oxygen atom and the sulfur atom, independently of one another, in such a way as to be identical or different, when there are 2 of them, or independently of one another, in such a way as to be identical or different, when there are 3 of them. Mention may be made of pyridyl, pyrrole and furanyl groups;

a heterocycloalkyl: an optionally bridged cyclic alkyl group containing 4, 5, 6 or 7 carbon atoms and comprising 1, 2 or 3 heteroatoms chosen from oxygen, nitrogen and sulfur. Mention may be made especially of piperidyl, piperazinyl, pyrrolidinyl, hexamethyleneimino, morpholinyl and 1,1-dioxydotetrahydrothienyl groups;

the letters α, β, γ and δ around the pyridine of the compounds of formula (I) make it possible to identify the positions of the various carbon atoms.

Among the compounds described in the present invention, mention may be made of a first group of compounds corresponding to formula (I) in which:

R represents a group —SO$_2$—NR3R4, a hydrogen atom, a halogen atom, a group -halo(C1-C5)alkyl, a group —CO$_2$R5 or a group —SO$_2$—R4; R3, R4 and R5 being as defined below;

and/or

R1 represents a heterocycloalkyl group not containing a nitrogen atom, a group —W—(C3-C6)cycloalkyl, a group —W-aryl, a group —W-heteroaryl, a group —W-heterocycloalkyl, a group —W—COOR5 or a group —W—CONR5R6, (i) the said aryl, heteroaryl and heterocycloalkyl groups being optionally substituted on at least one carbon atom with at least one substituent chosen from halogen atoms, groups (C1-C5)alkyl, groups —(C1-C5)alkylene-O—(C1-C5) alkyl, groups —(C1-C5)alkoxy, a hydroxyl function, groups -halo(C1-C5)alkyl, a cyano function, groups —O(C1-C5)alkylene-O—(C1-C5)alkyl, groups —O—(C1-C5)alkylene-NR5R6, groups —SO$_2$—(C1-C5)alkyl, groups —NR5R6 and groups —CO$_2$R5, and (ii) it being understood that when it is a heterocycloalkyl group, the said group comprising at least one nitrogen atom, this atom may optionally bear a substituent chosen from groups (C1-C5)alkyl, and/or R2 represents a hydrogen atom, a group —(C1-C5)alkyl, a group —(C1-C5)alkylene-0-(C1-C5)alkyl, a group -halo(C1-C5)alkyl, a group —W—COOR5, a group —W—C(O)NHR5 or a group —W—C(O)—NR5R6; W, R5 and R6 being as defined below;

and/or n represents 0, 1 or 2;

and/or

W is (i) a group —(C1-C5)alkylene-, optionally substituted with a group chosen from groups —(CH$_2$)n—CO$_2$R5 and groups —(CH$_2$)n—(CO)NR5R6, with n as defined above and R5 and R6 as defined below; or (ii) a group —(C3-C6)cycloalkylene-, and/or R3 and R4

(i) which may be identical or different, represent, independently of each other, a hydrogen atom, a group —(C1-C5)alkyl, a group —(C3-C6)cycloalkyl, a group —(C1-C5)alkylene-O—(C1-C5)alkyl, an aryl, a group —CH$_2$-aryl, a heteroaryl, a heterocycloalkyl, a group —W—OH, a group —W—CHOH—CH$_2$OH, a group —W—CO$_2$R5, a group —W—NR5R6 or a group —W—O—(CH$_2$)n-aryl;

the said groups —(C3-C6)cycloalkyl and heterocycloalkyl being optionally substituted on at least one carbon atom with at least one group chosen from —(C1-C5)alkyl, a group —(C1-C5)alkoxy, a hydroxyl function, a group —W—NR5R6 and a group —W—CO$_2$R5, in the case of the groups —(C3-C6)cycloalkyl and heterocycloalkyl and/or on at least one heteroatom chosen from nitrogen with at least one group chosen from —(C1-C5)alkyl, in the case of a heterocycloalkyl group, with W and n as defined previously and R5 and R6 as defined below and it being understood that when R3 and R4 are identical, they cannot be a hydrogen atom;

(ii) or alternatively R3 and R4 form, together with the nitrogen atom that bears them, a heterocycloalkyl group, optionally substituted on at least one carbon atom and/or, where appropriate, on at least one heteroatom, with at least one substituent chosen from groups —(C1-C5)alkyl and groups —CH$_2$-aryl;

and/or

R5 and R6, which may be identical or different, represent, independently of each other, a hydrogen atom, a group —(C1-C5)alkyl or a group —(C1-C5)haloalkyl; with the exclusion of the compounds already mentioned above per se.

A first subgroup of compounds of the invention is formed by the compounds of formula (I) in which R represents a group —SO$_2$—NR3R4, a group -halo(C1-C5)alkyl, a group —CO$_2$R5 or a group —SO$_2$—R4 with R3, R4 and R5 as defined above.

A second subgroup of compounds of the invention is formed by the compounds of formula (I) in which R represents a group —SO$_2$—NR3R4 or —CO$_2$R5 with R3, R5 and R4 as defined above.

A third subgroup of compounds of the invention is formed by the compounds of formula (I) in which R represents a hydrogen atom, a halogen atom, a group -halo(C1-C5)alkyl, a group —CO$_2$R5 or a group —SO$_2$—R4 with R4 and R5 as defined above.

A fourth subgroup of compounds of the invention is formed by the compounds of formula (I) in which R is a substituent of the atom in the 13 position of pyridine.

A fifth subgroup of compounds of the invention is formed by the compounds of formula (I) in which R1 represents a heterocycloalkyl group not containing a nitrogen atom, a group —W—(C3-C6)cycloalkyl, a group —W-aryl, a group —W-heteroaryl, a group —W-heterocycloalkyl, a group —W—COOR5 or a group —W—CONR5R6, the said aryl, heteroaryl and heterocycloalkyl groups being optionally substituted on at least one carbon atom with at least one substituent chosen from halogen atoms, groups (C1-C5)alkyl, groups —(C1-C5)alkylene-O—(C1-C5) alkyl, groups —(C1-C5)alkoxy, a hydroxyl function, groups -halo(C1-C5)alkyl, a cyano function, groups —O(C1-C5)alkylene-O—(C1-C5)alkyl, groups —O—(C1-C5)alkylene-NR5R6, groups —SO$_2$—(C1-C5) alkyl, groups —NR5R6 and groups —CO$_2$R5, and it being understood that when it is a heterocycloalkyl group, the said group comprising at least one nitrogen atom, this atom may optionally bear a substituent chosen from groups (C1-C5)alkyl, in which W is a group (C1-C5)alkylene or a group (C3-C6) cycloalkylene and in which R5 and R6, which may be identical or different, represent, independently of each other, a hydrogen atom, a group —(C1-C5)alkyl or a group —(C1-C5)haloalkyl.

Advantageously, the heterocycloalkyl group represents a piperidyl group, the aryl group represents a phenyl group and the heteroaryl group represents a pyridyl group.

A sixth subgroup of compounds of the invention is formed by the compounds of formula (I) in which R2 represents a hydrogen atom, a group —(C1-C5)alkyl, a group —(C1-C5) alkylene-O—(C1-C5)alkyl, a group -halo(C1-C5)alkyl, a group —W—COOR5, a group —W—C(O)NHR5 or a group —W—C(O)—NR5R6;

in which W, R5 and R6 are as defined above.

A seventh subgroup of compounds of the invention is formed by the compounds of formula (I) in which R represents a group —SO$_2$—NR3R4, advantageously in the β position of pyridine, and in which R3 and R4, which may be identical or different, represent, independently of each other, a hydrogen atom, a group —(C1-C5)alkyl, a group —(C3-C6)cycloalkyl, a group —(C1-C5)alkylene-O—(C1-C5) alkyl, an aryl, a group —CH$_2$-aryl, a heteroaryl, a heterocycloalkyl, a group —W—OH, a group —W—CHOH—CH$_2$OH, a group —W—CO$_2$R5, a group —W—NR5R6 or a group —W—O—(CH$_2$)n-aryl; it being understood that:

when R3 and R4 are identical, they cannot be a hydrogen atom; and that when R3 and/or R4 are chosen from the said groups —(C3-C6)cycloalkyl and heterocycloalkyl, these groups may be optionally substituted on at least one carbon atom, with at least one group chosen from —(C1-C5)alkyl, a group —(C1-C5) alkoxy, a hydroxyl function, a group —W—NR5R6 and a group —W—CO$_2$R5, in the case of the groups —(C3-C6)cycloalkyl and heterocycloalkyl, and/or on at least one heteroatom chosen from nitrogen with at least one group chosen from —(C1-C5)alkyl, in the case of a heterocycloalkyl group, in which W, R5 and R6 are as defined above and in which n represents 0, 1 or 2.

Advantageously, the heterocycloalkyl group represents a piperidyl group, the aryl group represents a phenyl group and the heteroaryl group represents a pyridyl group.

An eighth subgroup of compounds of the invention is formed by the compounds of formula (I) in which R represents a group —SO$_2$—NR3R4, advantageously in the β position of pyridine, and in which R3 and R4 form, together with the nitrogen atom that bears them, a heterocycloalkyl group, optionally substituted on at least one carbon atom and/or, where appropriate, on at least one heteroatom, with at least one substituent chosen from groups —(C1-C5)alkyl and groups —CH$_2$-aryl.

Advantageously, the said heterocycloalkyl group represents a group chosen from piperidyl, piperazinyl, morpholinyl, pyrrolidinyl and hexamethyleneimino groups, and the aryl group represents a phenyl group.

A seventh subgroup of compounds of the invention is formed by the compounds of formula (I) in which the group(s) R, R1 and/or R2 comprise the group(s) R5 and/or R6, R5 or R6 is a hydrogen atom, a group —(C1-C5)alkyl or a group —(C1-C5)haloalkyl, or R5 and R6, which may be identical or different, represent, independently of each other, a hydrogen atom, a group —(C1-C5)alkyl or a group —(C1-C5)haloalkyl.

Advantageously, R5 and/or R6 are chosen from groups (C1-C5)alkyl.

A tenth subgroup of compounds of the invention is formed by the compounds of formula (I) in which R represents a group —SO$_2$—NR3R4 or a hydrogen atom with R3 and R4 as defined above and/or R2 represents a hydrogen atom or a group —(C1-C5)alkyl, advantageously a methyl and/or R1 represents a group —W-aryl or a group —W-heteroaryl, advantageously with the said W representing a —CH$_2$—, the said aryl representing a phenyl and the said heteroaryl representing a pyridyl.

The subgroups defined above, taken separately or in combination, also form part of the invention.

The compounds below are excluded from the present invention, namely:

the compounds 4R1-[2-pyrimidyl]-pyrazolin-5-one for which R1=

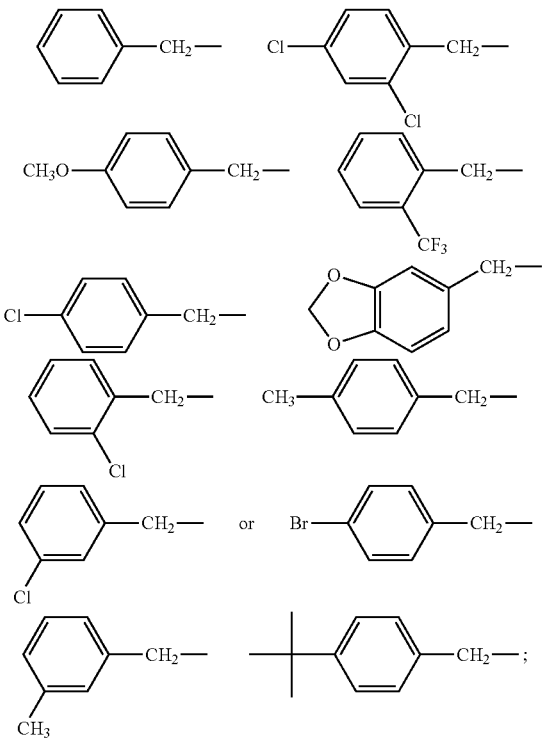

the compounds 3-methyl-4R1-[2-pyrimidyl]-pyrazoline-5-one below for which R1 represents:

a group

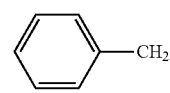

or a group

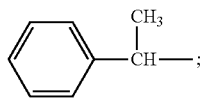

the compound:

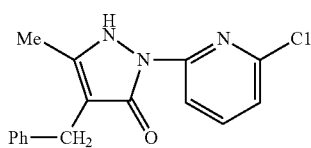

and
the compound:

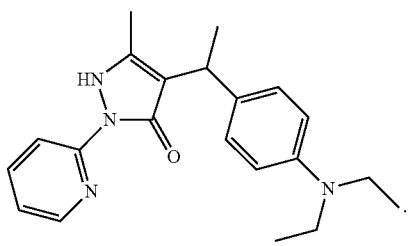 [SMILES: CCN(CC)c1ccc(C(C)c2c(C)[nH]n(-c3ccccn3)c2=O)cc1]

Among the compounds of formula (I) that are subjects of the invention, mention may be made especially of the following compounds:
4-(2-chlorobenzyl)-5-methyl-2-[5-(trifluoromethyl)pyridin-2-yl]-1,2-dihydro-3H-pyrazol-3-one;
Acide 6-[4-(2-chlorobenzyl)-3-methyl-5-oxo-2,5-dihydro-1H-pyrazol-1-yl]pyridine-3-carboxylic acid;
4-(2-chlorobenzyl)-5-methyl-2-(pyridin-2-yl)-1,2-dihydro-3H-pyrazol-3-one;
4-(2-chlorobenzyl)-5-methyl-2-{5-[(4-methylpiperazin-1-yl)sulfonyl]pyridin-2-yl}-1,2-dihydro-3H-pyrazol-3-one trifluoroacetate;
(±)-4-(2-chlorobenzyl)-2-(5-{[(3R,5S)-3,5-dimethylpiperidin-1-yl]sulfonyl}pyridin-2-yl)-5-methyl-1,2-dihydro-3H-pyrazol-3-one;
6-[4-(2-chlorobenzyl)-3-methyl-5-oxo-2,5-dihydro-1H-pyrazol-1-yl]-N,N-diethyl-pyridine-3-sulfonamide;
6-[4-(2-chlorobenzyl)-3-methyl-5-oxo-2,5-dihydro-1H-pyrazol-1-yl]-N-ethyl-N-phenyl-pyridine-3-sulfonamide;
6-[4-(2-chlorobenzyl)-3-methyl-5-oxo-2,5-dihydro-1H-pyrazol-1-yl]-N,N-di(propan-2-yl)pyridine-3-sulfonamide;
4-(2-chlorobenzyl)-5-methyl-2-[5-(piperidin-1-ylsulfonyl)pyridin-2-yl]-1,2-dihydro-3H-pyrazol-3-one;
N,N-diethyl-6-[4-(2-fluorobenzyl)-3-methyl-5-oxo-2,5-dihydro-1H-pyrazol-1-yl]-pyridine-3-sulfonamide;
4-(2-fluorobenzyl)-5-methyl-2-(pyridin-2-yl)-1,2-dihydro-3H-pyrazol-3-one;
4-(2-fluorobenzyl)-5-methyl-2-[5-(trifluoromethyl)pyridin-2-yl]-1,2-dihydro-3H-pyrazol-3-one;
4-(2-fluorobenzyl)-5-methyl-2-{5-[(4-methylpiperazin-1-yl)sulfonyl]pyridin-2-yl}-1,2-dihydro-3H-pyrazol-3-one trifluoroacetate;
2-(5-{[(3R,5S)-3,5-dimethylpiperidin-1-yl]sulfonyl}pyridin-2-yl)-4-(2-fluorobenzyl)-5-methyl-1,2-dihydro-3H-pyrazol-3-one;
N-ethyl-6-[4-(2-fluorobenzyl)-3-methyl-5-oxo-2,5-dihydro-1H-pyrazol-1-yl]-N-phenyl-pyridine-3-sulfonamide;
4-(2-fluorobenzyl)-5-methyl-2-[5-(piperidin-1-ylsulfonyl)pyridin-2-yl]-1,2-dihydro-3H-pyrazol-3-one;
4-(2,4-dichlorobenzyl)-5-methyl-2-(pyridin-2-yl)-1,2-dihydro-3H-pyrazol-3-one;
4-(2,4-dichlorobenzyl)-5-methyl-2-[5-(trifluoromethyl)pyridin-2-yl]-1,2-dihydro-3H-pyrazol-3-one;
4-(2,4-dichlorobenzyl)-5-methyl-2-{5-[(4-methylpiperazin-1-yl)sulfonyl]pyridin-2-yl}-1,2-dihydro-3H-pyrazol-3-one trifluoroacetate;
4-(2,4-dichlorobenzyl)-2-(5-{[(3R,5S)-3,5-dimethylpiperidin-1-yl]sulfonyl}pyridin-2-yl)-5-methyl-1,2-dihydro-3H-pyrazol-3-one;
6-[4-(2,4-dichlorobenzyl)-3-methyl-5-oxo-2,5-dihydro-1H-pyrazol-1-yl]-N-ethyl-N-phenylpyridine-3-sulfonamide;
6-[4-(2,4-dichlorobenzyl)-3-methyl-5-oxo-2,5-dihydro-1H-pyrazol-1-yl]-N,N-di(propan-2-yl)pyridine-3-sulfonamide;
4-(2,4-dichlorobenzyl)-5-methyl-2-[5-(piperidin-1-ylsulfonyl)pyridin-2-yl]-1,2-dihydro-3H-pyrazol-3-one;
4-(2-chloro-6-fluorobenzyl)-5-methyl-2-[5-(trifluoromethyl)pyridin-2-yl]-1,2-dihydro-3H-pyrazol-3-one;
4-(2-chloro-6-fluorobenzyl)-5-methyl-2-{5-[(4-methylpiperazin-1-yl)sulfonyl]pyridin-2-yl}-1,2-dihydro-3H-pyrazol-3-one trifluoroacetate;
4-(2-chloro-6-fluorobenzyl)-2-(5-{[(3R,5S)-3,5-dimethylpiperidin-1-yl]sulfonyl}pyridin-2-yl)-5-methyl-1,2-dihydro-3H-pyrazol-3-one;
6-[4-(2-chloro-6-fluorobenzyl)-3-methyl-5-oxo-2,5-dihydro-1H-pyrazol-1-yl]-N,N-diethylpyridine-3-sulfonamide;
6-[4-(2-chloro-6-fluorobenzyl)-3-methyl-5-oxo-2,5-dihydro-1H-pyrazol-1-yl]-N-ethyl-N-phenylpyridine-3-sulfonamide;
6-[4-(2-chloro-6-fluorobenzyl)-3-methyl-5-oxo-2,5-dihydro-1H-pyrazol-1-yl]-N,N-di(propan-2-yl)pyridine-3-sulfonamide;
4-(2-chloro-6-fluorobenzyl)-5-methyl-2-[5-(piperidin-1-ylsulfonyl)pyridin-2-yl]-1,2-dihydro-3H-pyrazol-3-one;
methyl 6-[4-(2-chlorobenzyl)-3-methyl-5-oxo-2,5-dihydro-1H-pyrazol-1-yl]pyridine-3-carboxylate;
4-(4-chlorobenzyl)-5-methyl-2-(pyridin-2-yl)-1,2-dihydro-3H-pyrazol-3-one;
4-(4-chlorobenzyl)-5-methyl-2-{5-[(4-methylpiperazin-1-yl)sulfonyl]pyridin-2-yl}-1,2-dihydro-3H-pyrazol-3-one;
4-(4-chlorobenzyl)-2-{5-[(R3R,5S)-3,5-dimethylpiperidin-1-yl]sulfonyl}pyridin-2-yl)-5-methyl-1,2-dihydro-3H-pyrazol-3-one;
6-[4-(4-chlorobenzyl)-3-methyl-5-oxo-2,5-dihydro-1H-pyrazol-1-yl]-N,N-diethylpyridine-3-sulfonamide;
6-[4-(4-chlorobenzyl)-3-methyl-5-oxo-2,5-dihydro-1H-pyrazol-1-yl]-N-ethyl-N-phenylpyridine-3-sulfonamide;
6-[4-(4-chlorobenzyl)-3-methyl-5-oxo-2,5-dihydro-1H-pyrazol-1-yl]-N,N-di(propan-2-yl)pyridine-3-sulfonamide;
4-(4-chlorobenzyl)-5-methyl-2-[5-(piperidin-1-ylsulfonyl)pyridin-2-yl]-1,2-dihydro-3H-pyrazol-3-one;
6-[4-(2-fluorobenzyl)-3-methyl-5-oxo-2,5-dihydro-1H-pyrazol-1-yl]-N,N-di(propan-2-yl)pyridine-3-sulfonamide;
4-(1,1-dioxidotetrahydrothiophen-3-yl)-5-methyl-2-[5-(piperidin-1-ylsulfonyl)pyridin-2-yl]-1,2-dihydro-3H-pyrazol-3-one;
6-[4-(1,1-dioxidotetrahydrothiophen-3-yl)-3-methyl-5-oxo-2,5-dihydro-1H-pyrazol-1-yl]-N-ethyl-N-phenylpyridine-3-sulfonamide;

6-[4-(1,1-dioxidotetrahydrothiophen-3-yl)-3-methyl-5-oxo-2,5-dihydro-1H-pyrazol-1-yl]-N,N-di(propan-2-yl)pyridine-3-sulfonamide;
2-{[5-methyl-3-oxo-2-(pyridin-2-yl)-2,3-dihydro-1H-pyrazol-4-yl]methyl}benzonitrile;
4-{[5-methyl-3-oxo-2-(pyridin-2-yl)-2,3-dihydro-1H-pyrazol-4-yl]methyl}benzonitrile;
N-ethyl-6-{4-[4-(methoxymethyl)benzyl]-3-methyl-5-oxo-2,5-dihydro-1H-pyrazol-1-yl}-N-phenylpyridine-3-sulfonamide;
4-[3-(methoxymethyl)benzyl]-5-methyl-2-(pyridin-2-yl)-1,2-dihydro-3H-pyrazol-3-one;
N-ethyl-6-{4-[3-(methoxymethyl)benzyl]-3-methyl-5-oxo-2,5-dihydro-1H-pyrazol-1-yl}-N-phenylpyridine-3-sulfonamide;
6-[4-(3-cyanobenzyl)-3-methyl-5-oxo-2,5-dihydro-1H-pyrazol-1-yl]-N-ethyl-N-phenylpyridine-3-sulfonamide;
6-[4-(4-cyanobenzyl)-3-methyl-5-oxo-2,5-dihydro-1H-pyrazol-1-yl]-N-ethyl-N-phenylpyridine-3-sulfonamide;
5-methyl-2-(pyridin-2-yl)-4-(pyridin-4-ylmethyl)-1,2-dihydro-3H-pyrazol-3-one;
3-{[5-methyl-3-oxo-2-(pyridin-2-yl)-2,3-dihydro-1H-pyrazol-4-yl]methyl}benzonitrile;
4-benzyl-2-(5-bromopyridin-2-yl)-5-methyl-1,2-dihydro-3H-pyrazol-3-one;
6-[4-(2-cyanobenzyl)-3-methyl-5-oxo-2,5-dihydro-1H-pyrazol-1-yl]-N-ethyl-N-phenylpyridine-3-sulfonamide;
N-ethyl-6-{4-[3-(2-methoxyethoxy)benzyl]-3-methyl-5-oxo-2,5-dihydro-1H-pyrazol-1-yl}-N-phenylpyridine-3-sulfonamide;
4-(3,5-dimethoxybenzyl)-5-methyl-2-(pyridin-2-yl)-1,2-dihydro-3H-pyrazol-3-one;
5-methyl-4-[4-(methylsulfonyl)benzyl]-2-(pyridin-2-yl)-1,2-dihydro-3H-pyrazol-3-one;
N-ethyl-6-{3-methyl-4-[4-(methylsulfonyl)benzyl]-5-oxo-2,5-dihydro-1H-pyrazol-1-yl}-N-phenylpyridine-3-sulfonamide;
4-[3-(2-methoxyethoxy)benzyl]-5-methyl-2-(pyridin-2-yl)-1,2-dihydro-3H-pyrazol-3-one;
4-benzyl-5-methyl-2-(pyridin-2-yl)-1,2-dihydro-3H-pyrazol-3-one;
N-ethyl-6-[3-methyl-5-oxo-4-(pyridin-4-ylmethyl)-2,5-dihydro-1H-pyrazol-1-yl]-N-phenylpyridine-3-sulfonamide;
N-ethyl-6-[3-methyl-5-oxo-4-(pyridin-2-ylmethyl)-2,5-dihydro-1H-pyrazol-1-yl]-N-phenylpyridine-3-sulfonamide;
5-methyl-2-(pyridin-2-yl)-4-(pyridin-3-ylmethyl)-1,2-dihydro-3H-pyrazol-3-one;
6-(4-benzyl-3-methyl-5-oxo-2,5-dihydro-1H-pyrazol-1-yl)-N-ethyl-N-phenylpyridine-3-sulfonamide;
N-ethyl-6-[3-methyl-5-oxo-4-(pyridin-3-ylmethyl)-2,5-dihydro-1H-pyrazol-1-yl]-N-phenylpyridine-3-sulfonamide;
4-(2,5-dimethoxybenzyl)-5-methyl-2-(pyridin-2-yl)-1,2-dihydro-3H-pyrazol-3-one;
6-[4-(2,5-dimethoxybenzyl)-3-methyl-5-oxo-2,5-dihydro-1H-pyrazol-1-yl]-N-ethyl-N-phenylpyridine-3-sulfonamide;
N-ethyl-6-{3-methyl-4-[(1-methylpiperidin-4-yl)methyl]-5-oxo-2,5-dihydro-1H-pyrazol-1-yl}-N-phenylpyridine-3-sulfonamide;
N-ethyl-6-{3-methyl-5-oxo-4-[4-(trifluoromethyl)benzyl]-2,5-dihydro-1H-pyrazol-1-yl}-N-phenylpyridine-3-sulfonamide;
N-ethyl-6-{3-methyl-5-oxo-4-[3-(trifluoromethyl)benzyl]-2,5-dihydro-1H-pyrazol-1-yl}-N-phenylpyridine-3-sulfonamide;
5-methyl-2-(pyridin-2-yl)-4-[3-(trifluoromethyl)benzyl]-1,2-dihydro-3H-pyrazol-3-one;
5-methyl-2-(pyridin-2-yl)-4-[4-(trifluoromethyl)benzyl]-1,2-dihydro-3H-pyrazol-3-one;
6-[4-(3,5-dimethoxybenzyl)-3-methyl-5-oxo-2,5-dihydro-1H-pyrazol-1-yl]-N-ethyl-N-phenylpyridine-3-sulfonamide;
4-(4-hydroxybenzyl)-5-methyl-2-(pyridin-2-yl)-1,2-dihydro-3H-pyrazol-3-one;
N-ethyl-6-[4-(4-hydroxybenzyl)-3-methyl-5-oxo-2,5-dihydro-1H-pyrazol-1-yl]-N-phenylpyridine-3-sulfonamide;
6-(4-{4-[2-(dimethylamino)ethoxy]benzyl}-3-methyl-5-oxo-2,5-dihydro-1H-pyrazol-1-yl)-N-ethyl-N-phenylpyridine-3-sulfonamide;
6-{4-[4-(dimethylamino)benzyl]-3-methyl-5-oxo-2,5-dihydro-1H-pyrazol-1-yl}-N-ethyl-N-phenylpyridine-3-sulfonamide;
5-methyl-2-(pyridin-2-yl)-4-[2-(trifluoromethyl)benzyl]-1,2-dihydro-3H-pyrazol-3-one;
4-[4-(dimethylamino)benzyl]-5-methyl-2-(pyridin-2-yl)-1,2-dihydro-3H-pyrazol-3-one;
N-ethyl-6-{3-methyl-5-oxo-4-[2-(trifluoromethyl)benzyl]-2,5-dihydro-1H-pyrazol-1-yl}-N-phenylpyridine-3-sulfonamide;
6-(4-benzyl-3-methyl-5-oxo-2,5-dihydro-1H-pyrazol-1-yl)-N-(3-methylbutyl)pyridine-3-sulfonamide;
4-[3-(dimethylamino)benzyl]-5-methyl-2-(pyridin-2-yl)-1,2-dihydro-3H-pyrazol-3-one;
6-{4-[3-(dimethylamino)benzyl]-3-methyl-5-oxo-2,5-dihydro-1H-pyrazol-1-yl}-N-ethyl-N-phenylpyridine-3-sulfonamide;
4-(4-methoxybenzyl)-5-methyl-2-(pyridin-2-yl)-1,2-dihydro-3H-pyrazol-3-one;
N-ethyl-6-[4-(4-methoxybenzyl)-3-methyl-5-oxo-2,5-dihydro-1H-pyrazol-1-yl]-N-phenylpyridine-3-sulfonamide;
4-(2-methoxybenzyl)-5-methyl-2-(pyridin-2-yl)-1,2-dihydro-3H-pyrazol-3-one;
4-(3-methoxybenzyl)-5-methyl-2-(pyridin-2-yl)-1,2-dihydro-3H-pyrazol-3-one;
N-ethyl-6-[4-(3-methoxybenzyl)-3-methyl-5-oxo-2,5-dihydro-1H-pyrazol-1-yl]-N-phenylpyridine-3-sulfonamide;
6-(4-{3-[2-(dimethylamino)ethoxy]benzyl}-3-methyl-5-oxo-2,5-dihydro-1H-pyrazol-1-yl)-N-ethyl-N-phenylpyridine-3-sulfonamide;
N-ethyl-6-[4-(2-methoxybenzyl)-3-methyl-5-oxo-2,5-dihydro-1H-pyrazol-1-yl]-N-phenylpyridine-3-sulfonamide;
4-benzyl-5-methyl-2-[5-(morpholin-4-ylsulfonyl)pyridin-2-yl]-1,2-dihydro-3H-pyrazol-3-one;
N-ethyl-6-[4-(3-hydroxybenzyl)-3-methyl-5-oxo-2,5-dihydro-1H-pyrazol-1-yl]-N-phenylpyridine-3-sulfonamide;
6-(4-benzyl-3-ethyl-5-oxo-2,5-dihydro-1H-pyrazol-1-yl)-N-ethyl-N-phenylpyridine-3-sulfonamide;
4-(3-hydroxybenzyl)-5-methyl-2-(pyridin-2-yl)-1,2-dihydro-3H-pyrazol-3-one;
N-ethyl-6-{4-[4-(2-methoxyethoxy)benzyl]-3-methyl-5-oxo-2,5-dihydro-1H-pyrazol-1-yl}-N-phenylpyridine-3-sulfonamide;
4-benzyl-5-ethyl-2-(pyridin-2-yl)-1,2-dihydro-3H-pyrazol-3-one;
4-benzyl-5-methyl-2-[5-(pyrrolidin-1-ylsulfonyl)pyridin-2-yl]-1,2-dihydro-3H-pyrazol-3-one;
2-[5-(azepan-1-ylsulfonyl)pyridin-2-yl]-4-benzyl-5-methyl-1,2-dihydro-3H-pyrazol-3-one;

N,N-diethyl-6-[3-methyl-5-oxo-4-(pyridin-3-ylmethyl)-2,5-dihydro-1H-pyrazol-1-yl]pyridine-3-sulfonamide;
N,N-diethyl-6-[3-methyl-5-oxo-4-(pyridin-3-ylmethyl)-2,5-dihydro-1H-pyrazol-1-yl]pyridine-3-sulfonamide hydrochloride;
N,N-dimethyl-6-[3-methyl-5-oxo-4-(pyridin-3-ylmethyl)-2,5-dihydro-1H-pyrazol-1-yl]pyridine-3-sulfonamide;
N,N-dimethyl-6-[3-methyl-5-oxo-4-(pyridin-3-ylmethyl)-2,5-dihydro-1H-pyrazol-1-yl]pyridine-3-sulfonamide hydrochloride;
6-(4-benzyl-5-oxo-3-propyl-2,5-dihydro-1H-pyrazol-1-yl)-N-ethyl-N-phenylpyridine-3-sulfonamide hydrochloride;
6-[3-methyl-5-oxo-4-(pyridin-3-ylmethyl)-2,5-dihydro-1H-pyrazol-1-yl]-N-(propan-2-yl)pyridine-3-sulfonamide hydrochloride;
5-methyl-4-(pyridin-3-ylmethyl)-2-[5-(pyrrolidin-1-ylsulfonyl)pyridin-2-yl]-1,2-dihydro-3H-pyrazol-3-one hydrochloride;
N-tert-butyl-6-[3-methyl-5-oxo-4-(pyridin-3-ylmethyl)-2,5-dihydro-1H-pyrazol-1-yl]-pyridine-3-sulfonamide hydrochloride;
N-cyclopropyl-6-[3-methyl-5-oxo-4-(pyridin-3-ylmethyl)-2,5-dihydro-1H-pyrazol-1-yl]pyridine-3-sulfonamide hydrochloride;
N-cyclopentyl-6-[3-methyl-5-oxo-4-(pyridin-3-ylmethyl)-2,5-dihydro-1H-pyrazol-1-yl]pyridine-3-sulfonamide hydrochloride;
N-ethyl-6-[3-methyl-5-oxo-4-(2-phenylethyl)-2,5-dihydro-1H-pyrazol-1-yl]-N-phenylpyridine-3-sulfonamide;
5-methyl-4-(2-phenylethyl)-2-(pyridin-2-yl)-1,2-dihydro-3H-pyrazol-3-one;
N-methyl-6-[3-methyl-5-oxo-4-(pyridin-3-ylmethyl)-2,5-dihydro-1H-pyrazol-1-yl]-N-(pyridin-2-yl)pyridine-3-sulfonamide hydrochloride;
2-{5-[(4-benzylpiperidin-1-yl)sulfonyl]pyridin-2-yl}-5-methyl-4-(pyridin-3-ylmethyl)-1,2-dihydro-3H-pyrazol-3-one;
N-ethyl-6-[3-methyl-5-oxo-4-(2-phenylpropan-2-yl)-2,5-dihydro-1H-pyrazol-1-yl]-N-phenylpyridine-3-sulfonamide;
N-ethyl-6-{4-[(6-methoxypyridin-2-yl) methyl]-3-methyl-5-oxo-2,5-dihydro-1H-pyrazol-1-yl}-N-phenylpyridine-3-sulfonamide;
6-[3-methyl-5-oxo-4-(pyridin-3-ylmethyl)-2,5-dihydro-1H-pyrazol-1-yl]-N-(pyridin-2-yl)pyridine-3-sulfonamide hydrochloride;
N-ethyl-6-[3-methyl-5-oxo-4-(1-phenylcyclopropyl)-2,5-dihydro-1H-pyrazol-1-yl]-N-phenylpyridine-3-sulfonamide;
N-ethyl-6-{4-[(3-methoxypyridin-2-yl)methyl]-3-methyl-5-oxo-2,5-dihydro-1H-pyrazol-1-yl}-N-phenylpyridine-3-sulfonamide hydrochloride;
6-[4-benzyl-3-(methoxymethyl)-5-oxo-2,5-dihydro-1H-pyrazol-1-yl]-N-ethyl-N-phenylpyridine-3-sulfonamide;
6-[4-benzyl-5-oxo-3-(trifluoromethyl)-2,5-dihydro-1H-pyrazol-1-yl]-N-ethyl-N-phenylpyridine-3-sulfonamide;
1-[5-(azepan-1-ylsulfonyl)pyridin-2-yl]-3-methyl-4-(pyridin-3-ylmethyl)-1H-pyrazol-5-olate;
N-ethyl-6-{3-methyl-5-oxo-4-[2-(pyridin-2-yl)ethyl]-2,5-dihydro-1H-pyrazol-1-yl}-N-phenylpyridine-3-sulfonamide;
N-ethyl-6-{4-[(5-methoxypyridin-3-yl)methyl]-3-methyl-5-oxo-2,5-dihydro-1H-pyrazol-1-yl}-N-phenylpyridine-3-sulfonamide;
N-(2-methoxyethyl)-N-methyl-6-[3-methyl-5-oxo-4-(pyridin-3-ylmethyl)-2,5-dihydro-1H-pyrazol-1-yl]pyridine-3-sulfonamide;
6-[4-benzyl-3-(2-methylpropyl)-5-oxo-2,5-dihydro-1H-pyrazol-1-yl]-N-ethyl-N-phenylpyridine-3-sulfonamide;
N-ethyl-6-[3-methyl-5-oxo-4-(pyridin-3-ylmethyl)-2,5-dihydro-1H-pyrazol-1-yl]pyridine-3-sulfonamide;
6-[3-methyl-5-oxo-4-(pyridin-3-ylmethyl)-2,5-dihydro-1H-pyrazol-1-yl]-N-phenylpyridine-3-sulfonamide;
N-ethyl-6-[3-methyl-5-oxo-4-(3-phenylpropyl)-2,5-dihydro-1H-pyrazol-1-yl]-N-phenylpyridine-3-sulfonamide;
6-(4-benzyl-5-oxo-2,5-dihydro-1H-pyrazol-1-yl)-N-ethyl-N-phenylpyridine-3-sulfonamide;
N-cyclopropyl-N-methyl-6-[3-methyl-5-oxo-4-(pyridin-3-ylmethyl)-2,5-dihydro-1H-pyrazol-1-yl]pyridine-3-sulfonamide;
N-tert-butyl-6-{4-[(5-methoxypyridin-3-yl)methyl]-3-methyl-5-oxo-2,5-dihydro-1H-pyrazol-1-yl}pyridine-3-sulfonamide;
6-{4-[(5-cyanopyridin-3-yl)methyl]-3-methyl-5-oxo-2,5-dihydro-1H-pyrazol-1-yl}-N-ethyl-N-phenylpyridine-3-sulfonamide;
tert-butyl 6-[5-oxo-4-(pyridin-3-ylmethyl)-2,5-dihydro-1H-pyrazol-1-yl]pyridine-3-carboxylate;
tert-butyl 6-[3-methyl-5-oxo-4-(pyridin-3-ylmethyl)-2,5-dihydro-1H-pyrazol-1-yl]pyridine-3-carboxylate;
N-tert-butyl-6-[5-oxo-4-(pyridin-3-ylmethyl)-2,5-dihydro-1H-pyrazol-1-yl]pyridine-3-sulfonamide;
N-tert-butyl-6-[5-oxo-4-(pyridin-3-ylmethyl)-2,5-dihydro-1H-pyrazol-1-yl]pyridine-3-sulfonamide hydrochloride;
N-ethyl-6-[5-oxo-4-(pyridin-3-ylmethyl)-2,5-dihydro-1H-pyrazol-1-yl]-N-phenylpyridine-3-sulfonamide;
6-(4-benzyl-5-oxo-2,5-dihydro-1H-pyrazol-1-yl)-N-tert-butyl-N-methylpyridine-3-sulfonamide;
N-ethyl-6-{4-[(5-methoxypyridin-3-yl)methyl]-5-oxo-2,5-dihydro-1H-pyrazol-1-yl}-N-phenylpyridine-3-sulfonamide;
5-methyl-2-[5-(phenylsulfonyl)pyridin-2-yl]-4-(pyridin-3-ylmethyl)-1,2-dihydro-3H-pyrazol-3-one;
N-tert-butyl-6-{4-[(5-methoxypyridin-3-yl)methyl]-3-methyl-5-oxo-2,5-dihydro-1H-pyrazol-1-yl}-N-methylpyridine-3-sulfonamide;
6-{4-[(6-cyanopyridin-3-yl)methyl]-3-methyl-5-oxo-2,5-dihydro-1H-pyrazol-1-yl}-N-ethyl-N-phenylpyridine-3-sulfonamide;
(2-{5-[ethyl(phenyl)sulfamoyl]pyridin-2-yl}-3-oxo-2,3-dihydro-1H-pyrazol-4-yl)acetic acid;
2-(2-{5-[ethyl(phenyl)sulfamoyl]pyridin-2-yl}-3-oxo-2,3-dihydro-1H-pyrazol-4-yl)-N,N-dimethylacetamide;
methyl (2-{5-[ethyl(phenyl)sulfamoyl]pyridin-2-yl}-3-oxo-2,3-dihydro-1H-pyrazol-4-yl)acetate;
ethyl (4-benzyl-1-{5-[ethyl(phenyl)sulfamoyl]pyridin-2-yl}-5-oxo-2,5-dihydro-1H-pyrazol-3-yl)acetate;
2-(2-{5-[ethyl(phenyl)sulfamoyl]pyridin-2-yl}-3-oxo-2,3-dihydro-1H-pyrazol-4-yl)-N-methylacetamide;
N-tert-butyl-6-{4-[(5-methoxypyridin-2-yl)methyl]-3-methyl-5-oxo-2,5-dihydro-1H-pyrazol-1-yl}-N-methylpyridine-3-sulfonamide;
2-(4-benzyl-1-{5-[ethyl(phenyl)sulfamoyl]pyridin-2-yl}-5-oxo-2,5-dihydro-1H-pyrazol-3-yl)-N,N-dimethylacetamide;
3-(2-{5-[ethyl(phenyl)sulfamoyl]pyridin-2-yl}-3-oxo-2,3-dihydro-1H-pyrazol-4-yl)propanoic acid;
methyl 3-[(2-{5-[ethyl(phenyl)sulfamoyl]pyridin-2-yl}-5-methyl-3-oxo-2,3-dihydro-1H-pyrazol-4-yl)methyl]benzoate;
methyl 3-(2-{5-[ethyl(phenyl)sulfamoyl]pyridin-2-yl}-3-oxo-2,3-dihydro-1H-pyrazol-4-yl)propanoate;
methyl {2-[5-(tert-butylsulfamoyl)pyridin-2-yl]-3-oxo-2,3-dihydro-1H-pyrazol-4-yl}(phenyl)acetate;

methyl 2-[(2-{5-[ethyl(phenyl)Sulfamoyl]pyridin-2-yl}-5-methyl-3-oxo-2,3-dihydro-1H-pyrazol-4-yl)methyl]benzoate;
N-cyclopentyl-N-ethyl-6-[5-oxo-4-(pyridin-3-ylmethyl)-2,5-dihydro-1H-pyrazol-1-yl]pyridine-3-sulfonamide;
N-cyclopentyl-N-methyl-6-[5-oxo-4-(pyridin-3-ylmethyl)-2,5-dihydro-1H-pyrazol-1-yl]pyridine-3-sulfonamide;
2-[(1-{5-[ethyl(phenyl)sulfamoyl]pyridin-2-yl}-3-methyl-5-oxido-1H-pyrazol-4-yl)methyl]benzoate;
2-[5-(azepan-1-ylsulfonyl)pyridin-2-yl]-4-(pyridin-3-ylmethyl)-1,2-dihydro-3H-pyrazol-3-one;
N-cyclopentyl-N-methyl-6-[5-oxo-4-(pyridin-4-ylmethyl)-2,5-dihydro-1H-pyrazol-1-yl]pyridine-3-sulfonamide;
N-cyclopentyl-N-ethyl-6-[5-oxo-4-(pyridin-4-ylmethyl)-2,5-dihydro-1H-pyrazol-1-yl]pyridine-3-sulfonamide;
methyl 3-(2-{5-[cyclopentyl(methyl)sulfamoyl]pyridin-2-yl}-3-oxo-2,3-dihydro-1H-pyrazol-4-yl)-3-phenylpropanoate;
N-(2,2-dimethylpropyl)-N-methyl-6-[5-oxo-4-(pyridin-3-ylmethyl)-2,5-dihydro-1H-pyrazol-1-yl]pyridine-3-sulfonamide;
2,2-dimethylpropyl 6-[5-oxo-4-(pyridin-3-ylmethyl)-2,5-dihydro-1H-pyrazol-1-yl]pyridine-3-carboxylate;
methyl N-cyclopentyl-N-({6-[5-oxo-4-(pyridin-3-ylmethyl)-2,5-dihydro-1H-pyrazol-1-yl]pyridin-3-yl}sulfonyl)glycinate;
6-(4-benzyl-5-oxo-2,5-dihydro-1H-pyrazol-1-yl)-N-[2-(benzyloxy)ethyl]-N-cyclopentylpyridine-3-sulfonamide;
6-(4-benzyl-5-oxo-2,5-dihydro-1H-pyrazol-1-yl)-N-[3-(benzyloxy)propyl]-N-cyclopentylpyridine-3-sulfonamide;
6-(4-benzyl-5-oxo-2,5-dihydro-1H-pyrazol-1-yl)-N-cyclopentyl-N-(3-hydroxypropyl)pyridine-3-sulfonamide;
6-(4-benzyl-5-oxo-2,5-dihydro-1H-pyrazol-1-yl)-N-cyclopentyl-N-(2-hydroxyethyl)pyridine-3-sulfonamide;
methyl (1S,2R)-2-[methyl({6-[5-oxo-4-(pyridin-3-ylmethyl)-2,5-dihydro-1H-pyrazol-1-yl]pyridin-3-yl}sulfonyl)amino]cyclopentanecarboxylate;
6-(4-benzyl-5-oxo-2,5-dihydro-1H-pyrazol-1-yl)-N-cyclopentyl-N-(2,3-dihydroxypropyl)pyridine-3-sulfonamide;
6-(4-benzyl-5-oxo-2,5-dihydro-1H-pyrazol-1-yl)-N-cyclopentyl-N-[2-(dimethylamino)ethyl]pyridine-3-sulfonamide;
4-benzyl-2-{5-[(4-methylpiperazin-1-yl)sulfonyl]pyridin-2-yl}-1,2-dihydro-3H-pyrazol-3-one;
6-[4-(cyclopentylmethyl)-5-oxo-2,5-dihydro-1H-pyrazol-1-yl]-N-ethyl-N-phenylpyridine-3-sulfonamide;
4-benzyl-2-{5-[(4-methyl-1,4-diazepan-1-yl)sulfonyl]pyridin-2-yl}-1,2-dihydro-3H-pyrazol-3-one;
N-(2,2-dimethylpropyl)-6-[5-oxo-4-(pyridin-3-ylmethyl)-2,5-dihydro-1H-pyrazol-1-yl]pyridine-3-sulfonamide;
N-(2-methylbutan-2-yl)-6-[5-oxo-4-(pyridin-3-ylmethyl)-2,5-dihydro-1H-pyrazol-1-yl]pyridine-3-sulfonamide;
6-(4-benzyl-5-oxo-2,5-dihydro-1H-pyrazol-1-yl)-N-[(1R,3S)-3-(hydroxymethyl)cyclopentyl]-N-methylpyridine-3-sulfonamide;
6-(4-benzyl-5-oxo-2,5-dihydro-1H-pyrazol-1-yl)-N-methyl-N-(1-methylpyrrolidin-3-yl)pyridine-3-sulfonamide;
6-(4-benzyl-5-oxo-2,5-dihydro-1H-pyrazol-1-yl)-N-(2-methoxy-2-methylpropyl)pyridine-3-sulfonamide;
2,2-dimethylpropyl 6-(4-benzyl-5-oxo-2,5-dihydro-1H-pyrazol-1-yl)pyridine-3-carboxylate;
6-(4-benzyl-5-oxo-2,5-dihydro-1H-pyrazol-1-yl)-N-cyclopentyl-N-[(2R)-2,3-dihydroxypropyl]pyridine-3-sulfonamide;
6-(4-benzyl-5-oxo-2,5-dihydro-1H-pyrazol-1-yl)-N-(2,3-dihydroxypropyl)-N-phenylpyridine-3-sulfonamide;
N-cyclopentyl-6-{4-[(4-methoxypyridin-3-yl)methyl]-5-oxo-2,5-dihydro-1H-pyrazol-1-yl}-N-methylpyridine-3-sulfonamide;
N-methyl-N-(2-methylbutan-2-yl)-6-[5-oxo-4-(pyridin-3-ylmethyl)-2,5-dihydro-1H-pyrazol-1-yl]pyridine-3-sulfonamide;
3-(2-{5-[cyclopentyl(methyl)sulfamoyl]pyridin-2-yl}-3-oxo-2,3-dihydro-1H-pyrazol-4-yl)-3-phenyl-N-(2,2,2-trifluoroethyl)propanamide;
6-(4-benzyl-5-oxo-2,5-dihydro-1H-pyrazol-1-yl)-N-cyclopentyl-N-[3-hydroxy-2-(hydroxymethyl)propyl]pyridine-3-sulfonamide;
6-(4-benzyl-5-oxo-2,5-dihydro-1H-pyrazol-1-yl)-N-cyclopentyl-N-[(2S)-2,3-dihydroxypropyl]pyridine-3-sulfonamide;
2,2-dimethylpropyl 6-[5-oxo-4-(pyridin-4-ylmethyl)-2,5-dihydro-1H-pyrazol-1-yl]pyridine-3-carboxylate;
6-(4-benzyl-5-oxo-2,5-dihydro-1H-pyrazol-1-yl)-N-[(1S,2S)-2-hydroxycyclopentyl]-pyridine-3-sulfonamide;
N-tert-butyl-6-[5-oxo-4-(pyridin-4-ylmethyl)-2,5-dihydro-1H-pyrazol-1-yl]pyridine-3-sulfonamide;
4-benzyl-2-(5-{[(3R)-3-(dimethylamino)pyrrolidin-1-yl]sulfonyl}pyridin-2-yl)-1,2-dihydro-3H-pyrazol-3-one;
6-(4-benzyl-5-oxo-2,5-dihydro-1H-pyrazol-1-yl)-N-[1-(dimethylamino)-2-methylpropan-2-yl]pyridine-3-sulfonamide;
6-(4-benzyl-5-oxo-2,5-dihydro-1H-pyrazol-1-yl)-N-methyl-N-phenylpyridine-3-sulfonamide;
methyl 3-{2-[5-(tert-butylsulfamoyl)pyridin-2-yl]-3-oxo-2,3-dihydro-1H-pyrazol-4-yl}-3-(pyridin-3-yl)propanoate;
ethyl 3-{2-[5-(tert-butylsulfamoyl)pyridin-2-yl]-3-oxo-2,3-dihydro-1H-pyrazol-4-yl}-3-phenylpropanoate;
6-(4-benzyl-5-oxo-2,5-dihydro-1H-pyrazol-1-yl)-N-tert-butyl-N-(2,3-dihydroxypropyl)pyridine-3-sulfonamide;
6-(4-benzyl-5-oxo-2,5-dihydro-1H-pyrazol-1-yl)-N-(2-hydroxyethyl)pyridine-3-sulfonamide;
N-(2,3-dihydroxypropyl)-6-[5-oxo-4-(pyridin-3-ylmethyl)-2,5-dihydro-1H-pyrazol-1-yl]-N-phenylpyridine-3-sulfonamide hydrochloride;
methyl 3-(2-{5-[cyclopentyl(methyl)sulfamoyl]pyridin-2-yl}-3-oxo-2,3-dihydro-1H-pyrazol-4-yl)-3-(pyridin-3-yl)propanoate hydrochloride;
6-(4-benzyl-5-oxo-2,5-dihydro-1H-pyrazol-1-yl)-N-cyclopentyl-N-[3-(dimethylamino)propyl]pyridine-3-sulfonamide hydrochloride;
6-(4-benzyl-5-oxo-2,5-dihydro-1H-pyrazol-1-yl)-N-cyclopentyl-N-[3-(dimethylamino)propyl]pyridine-3-sulfonamide hydrochloride.

In the text hereinbelow, the term "protecting group" (PG) means a group that can, firstly, protect a reactive function such as an alcohol or an amine during a synthesis. Examples of protecting groups and of protection and deprotection methods are given in "Protective Groups in Organic Synthesis", Green et al., 3rd edition (John Wiley & Sons, Inc., New York).

In the text hereinbelow, the term "leaving group" (LG) means a nucleofugal group that can be readily cleaved from a molecule by breaking a heterolytic bond, with loss of an electron pair. This group may thus be readily replaced with another nucleophilic group during a substitution reaction, for example. Such leaving groups are, for example, halogens or an activated hydroxyl group such as a mesyl, tosyl, triflate, acetyl, etc. group. Examples of leaving groups and of references for preparing them are given in "Advances in Organic Chemistry", J. March, 3rd edition, Wiley Interscience, pp. 310-316.

In accordance with the invention, the compounds of general formula (I) may be prepared according to the processes hereinbelow.

Scheme 1 describes the synthesis of the compounds of formula (I) for which R may be a group —SO$_2$—NR3R4, a hydrogen atom, a halogen atom, a group -halo(C1-C5)alkyl, a group —CO$_2$R5 or a group —SO$_2$—R4; R1 may be a heterocycloalkyl group not containing a nitrogen atom, a group —W—(C3-C6)cycloalkyl, a group —W-aryl, a group —W-heteroaryl, a group —W-heterocycloalkyl, a group —W—COOR5 or a group —W—CONR5R6, with R3, R4 and R5 as defined above; W may be a group (C1-C5)alkylene, and n may be 0, 1 or 2.

These compounds are referred to hereinbelow as compounds of formula (Ia).

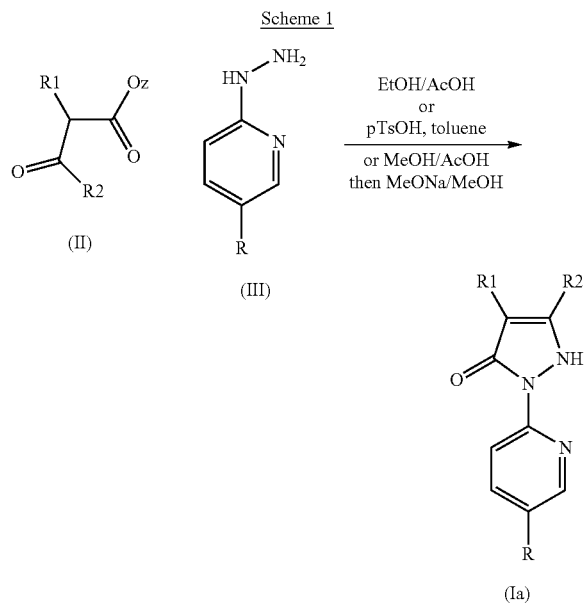

In Scheme 1, compounds of formula (II), for which R1 and R2 are as defined for the compounds of formula (Ia) and z represents an alkyl group such as a methyl or ethyl group, react with the compounds of formula (III) to give the compounds of formula (Ia), preferably in a protic solvent such as an ethanol/acetic acid mixture at a temperature of 80° C. or in an aprotic solvent such as toluene, at a temperature of between 80 and 110° C., in the presence of catalytic amounts of an organic acid such as para-toluenesulfonic acid. Alternatively, they may be obtained sequentially by reaction in a methanol/acetic acid mixture to obtain the intermediate hydrazone, followed by a cyclization reaction in methanol in the presence of sodium methoxide, preferably at a temperature of 40° C.

The compounds (I) obtained are optionally converted with an acid or a base into the corresponding salts thereof.

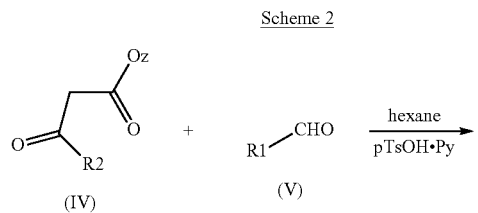

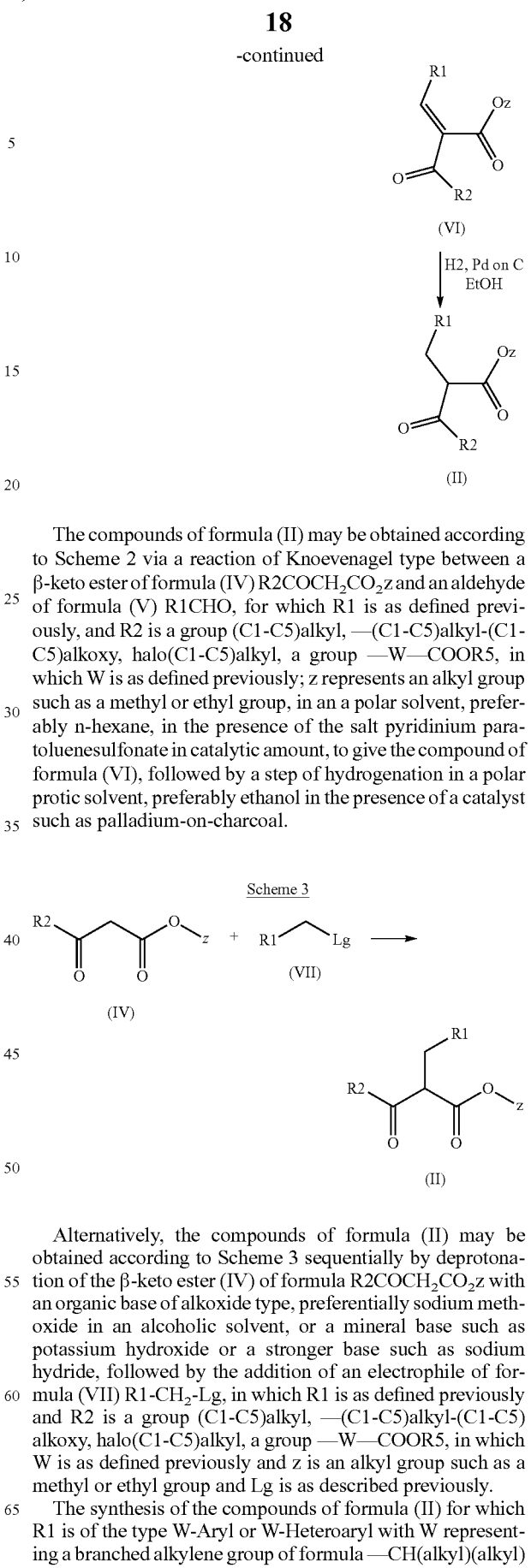

The compounds of formula (II) may be obtained according to Scheme 2 via a reaction of Knoevenagel type between a β-keto ester of formula (IV) R2COCH$_2$CO$_2$z and an aldehyde of formula (V) R1CHO, for which R1 is as defined previously, and R2 is a group (C1-C5)alkyl, —(C1-C5)alkyl-(C1-C5)alkoxy, halo(C1-C5)alkyl, a group —W—COOR5, in which W is as defined previously; z represents an alkyl group such as a methyl or ethyl group, in an a polar solvent, preferably n-hexane, in the presence of the salt pyridinium para-toluenesulfonate in catalytic amount, to give the compound of formula (VI), followed by a step of hydrogenation in a polar protic solvent, preferably ethanol in the presence of a catalyst such as palladium-on-charcoal.

Alternatively, the compounds of formula (II) may be obtained according to Scheme 3 sequentially by deprotonation of the β-keto ester (IV) of formula R2COCH$_2$CO$_2$z with an organic base of alkoxide type, preferentially sodium methoxide in an alcoholic solvent, or a mineral base such as potassium hydroxide or a stronger base such as sodium hydride, followed by the addition of an electrophile of formula (VII) R1-CH$_2$-Lg, in which R1 is as defined previously and R2 is a group (C1-C5)alkyl, —(C1-C5)alkyl-(C1-C5)alkoxy, halo(C1-C5)alkyl, a group —W—COOR5, in which W is as defined previously and z is an alkyl group such as a methyl or ethyl group and Lg is as described previously.

The synthesis of the compounds of formula (II) for which R1 is of the type W-Aryl or W-Heteroaryl with W representing a branched alkylene group of formula —CH(alkyl)(alkyl)

is described in Scheme 4. These compounds are referred to hereinbelow as compounds of formula (IIa).

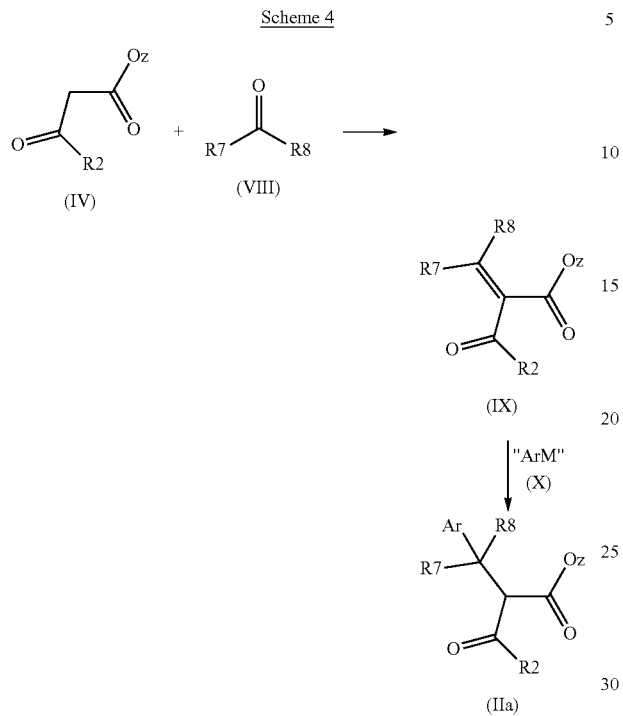

The compounds of formula (IX) are obtained by condensation of a ketone of formula (VIII) R7COR8, with R7 and R8 and possibly being, independently or together, a C1 to C4 alkyl group, with a β-keto ester of formula (IV) R2-CH$_2$—CO$_2$z in which R2 is as defined previously and z is an alkyl group such as a methyl or ethyl group, in the presence of a Lewis acid, preferably zinc chloride, in a solvent such as acetic anhydride, at a temperature of between 40° C. and 80° C. The compounds of formula (IIa) are then obtained via 1,4 addition of an organometallic compound of formula (X) Aryl-Metal ("ArM"), preferably an organomagnesium compound of the type Aryl-MgX, with X representing a halogen atom such as a bromine or chlorine atom, in the presence of a catalytic amount of copper iodide, with the compound of formula (IX) in an anhydrous solvent, preferably ethyl ether.

The synthesis of the compounds of formula (II) for which R2 is a hydrogen is described in Scheme 5. These compounds are referred to hereinbelow as compounds of formula (IIb).

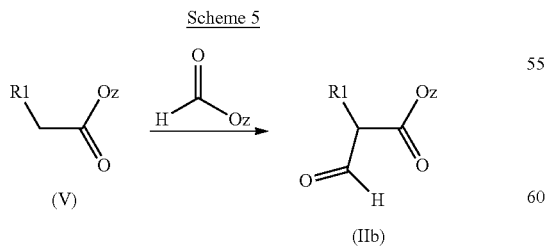

The compounds of formula (IIb) are obtained by formylation of the ester (V) of formula R1-CH$_2$—CO$_2$z in which R1 is as defined previously and z is an alkyl group such as a methyl or ethyl group. The formylation step consists in preferentially reacting methyl or ethyl formate with the ester (V) in the presence either of sodium metal in an anhydrous aprotic solvent such as ethyl ether, at a temperature of between 0° C. and 30° C., or in the presence of a Lewis acid such as titanium tetrachloride and an organic base such as tributylamine in the presence of catalytic amounts of trimethylsilyl trifluoromethanesulfonate, in an aprotic solvent such as toluene, at a temperature of between 50° C. and 60° C.

When they are not commercially available, the synthesis of the compounds of formula (III), for which R represents a haloalkyl group or —CO$_2$R5 with R5 as described previously, is described in Scheme 6. These compounds are referred to hereinbelow as compounds of formula (IIIa).

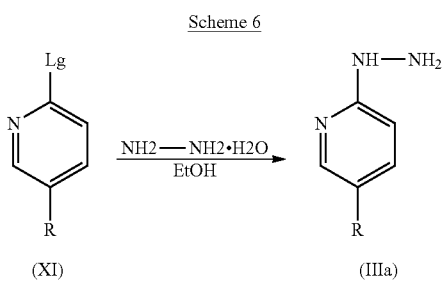

The compounds of formula (IIIa) are obtained from compound XI, with Lg and R as defined previously, by addition of hydrazine hydrate, preferably in a protic solvent such as EtOH at a temperature of between 60 and 80° C.

The synthesis of the compounds of formula (III), for which R represents a group —SO$_2$NR3R4 and R3 and R4 are as described previously, is described in Scheme 7. These compounds are referred to hereinbelow as compounds of formula (IIIb).

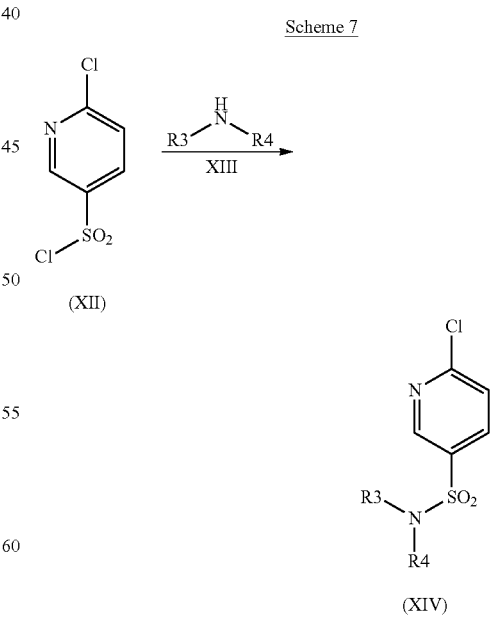

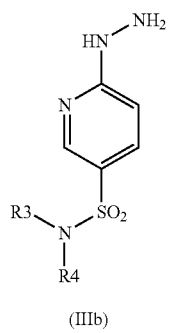

(IIIb)

The compounds of formula (IIIb) are obtained from 2-chloro-5-sulfonylpyridine chloride of formula (XII), by reaction on an amine of formula (XIII) R3NHR4 with R3 and R4 as defined previously, in the presence of an organic base, preferably triethylamine, in a polar solvent, preferably dichloromethane. The compound obtained of formula (XIV) is then treated with hydrazine hydrate in a protic solvent such as ethanol at 70° C., to give the desired compounds.

The synthesis of the compounds of formula (III) for which R is an alkyl or alkoxy group is described in Scheme 8. These compounds are referred to hereinbelow as compounds of formula (IIIc). The compounds of formula (IIIc) are obtained from the compound of formula (XV), with Lg and R as defined previously. The hydrazine function is introduced via a coupling reaction between the benzophenone hydrazone of formula (XVI) and the compound of formula (XV) in the presence of a catalytic amount of palladium, to give the intermediate of formula (XVII), the hydrazine function of which is released by acid treatment, such as hydrochloric acid, in a binary mixture of immiscible solvents such as toluene and water, at a temperature of 100° C.

Scheme 8

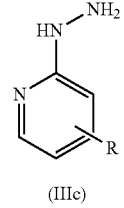

(IIIc)

Scheme 9 describes the synthesis of the compounds (I) for which R1 is a group —W-aryl or —W-heteroaryl, the said groups being substituted with one or more groups —NR5R6 and in which W is a group (C1-C5)alkylene. These compounds are referred to hereinbelow as compounds of formula (Ib).

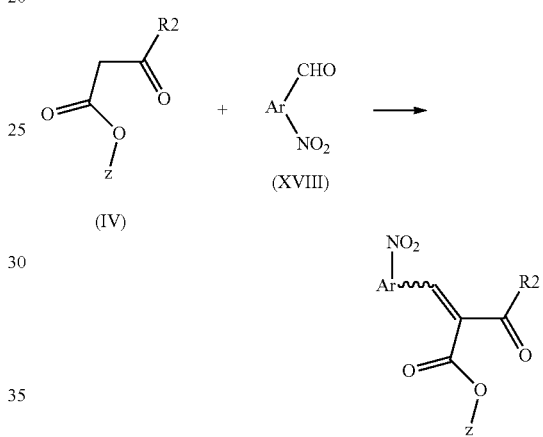

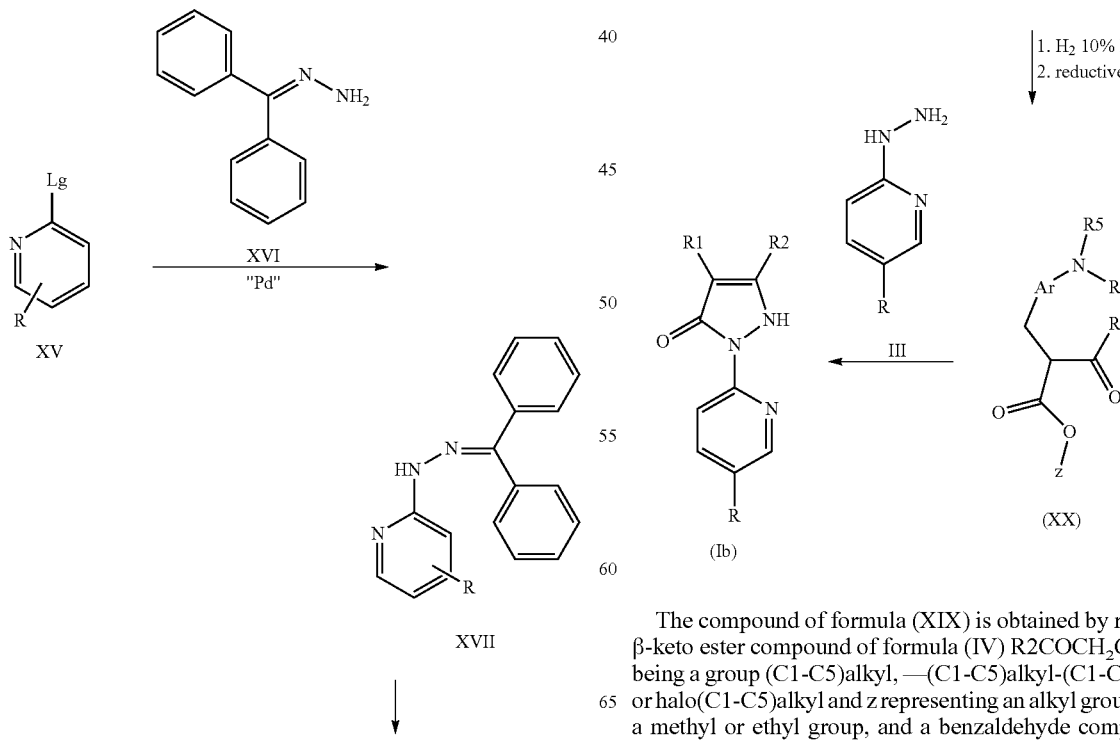

The compound of formula (XIX) is obtained by reacting a β-keto ester compound of formula (IV) R2COCH$_2$CO$_2$z, R2 being a group (C1-C5)alkyl, —(C1-C5)alkyl-(C1-C5)alkoxy or halo(C1-C5)alkyl and z representing an alkyl group such as a methyl or ethyl group, and a benzaldehyde compound of formula (XVIII) substituted with one or more nitro groups.

The compound of formula (XX) is then obtained by total hydrogenation in the presence of a catalyst such as palladium-on-charcoal in a protic solvent such as ethanol, preferentially followed by a reductive amination, under conditions such as, when R5 and R6 are a methyl group, formic acid in the presence of a reducing agent such as sodium triacetoxyborohydride in a protic solvent such as acetic acid. Compound (XX) is then reacted as described in Scheme 1 with the compound of formula (III) to give the desired compounds of formula (Ib).

Scheme 10 describes the synthesis of the compounds (I) for which R1 is a group —W-aryl, with W being a group (C1-C5)alkylene; the said aryl group being substituted with one or more groups —O(C1-C5)alkyl-O—(C1-C5)alkyl-(C1-C5)alkoxy or —O—(C1-C5)alkyl-NR5R6. These compounds are referred to hereinbelow as compounds of formula (Ic).

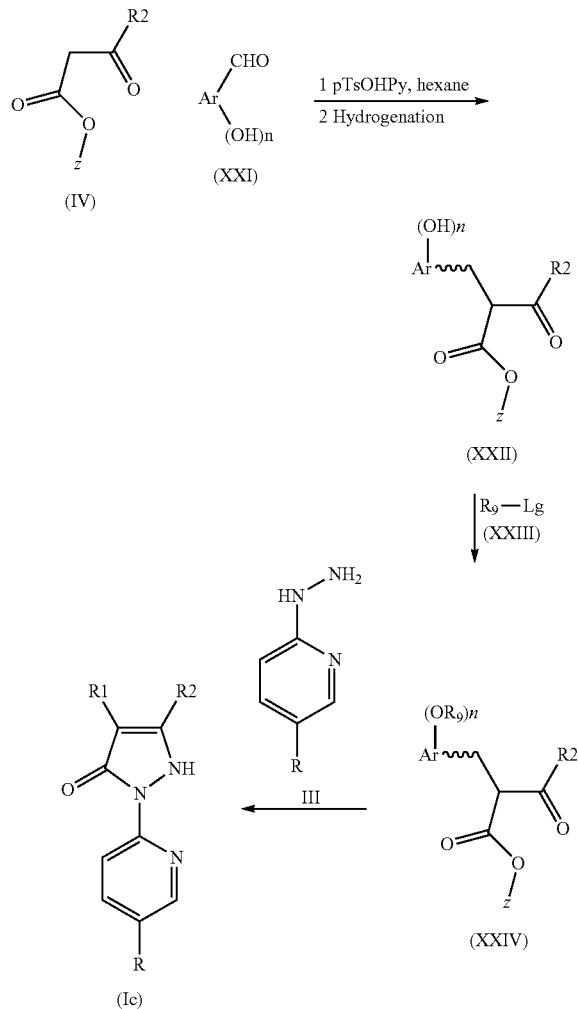

Scheme 10

The compound of formula (XXII) is obtained by reacting a β-keto ester compound of formula (IV) R2COCH$_2$CO$_2$z, with R2 being as described previously and z representing an alkyl group such as a methyl or ethyl group, and a benzaldehyde compound of formula (XXI), followed by a step of total hydrogenation in the presence of palladium-on-charcoal, preferably in a solvent such as ethanol. The compound of formula (XXIV) is then obtained by alkylation with a compound of formula (XXIII) R$_9$-Lg, with R$_9$ representing a group (C1-C5)alkylene, —(C1-C5)alkyl-(C1-C5)alkoxy or —(C1-C5)alkyl-NR5R$_6$ and Lg being as defined previously, in the presence of a base, preferentially a mineral base such as potassium carbonate, and in a polar solvent such as DMF; it is then reacted as described in Scheme 1 with the compound of formula (III) to give the desired compounds of formula (Ic).

In the examples that follow, the starting compounds, the intermediates and the reagents, when their mode of preparation is not described, are commercially available or are described in the literature, or else may be prepared according to methods that are known to those skilled in the art.

The examples that follow illustrate the preparation of certain compounds in accordance with the invention. The numbers of the compounds given as examples referred to those in the table given later, which illustrates the chemical structures and physical properties of a few compounds according to the invention.

The following abbreviations and formulae are used:

| | |
|---|---|
| EtOAc | Ethyl acetate |
| DCM | Dichloromethane |
| DMF | Dimethylformamide |
| DMSO | Dimethyl sulfoxide |
| DME | 1,2-Dimethoxyethane |
| EtOH | Ethanol |
| tBuOH | tert-Butanol |
| Et$_2$O | Diethyl ether |
| MeOH | Methanol |
| iPrOH | Isopropanol |
| AcOH | Acetic acid |
| CH$_3$CN | Acetonitrile |
| Et$_2$O | Diethyl ether |
| THF | Tetrahydrofuran |
| h | Hour(s) |
| HCl | Hydrochloric acid |
| H$_2$SO$_4$ | Sulfuric acid |
| K$_2$CO$_3$ | Potassium carbonate |
| KOH | Potassium hydroxide |
| NH$_4$Cl | Ammonium chloride |
| NaHCO$_3$ | Sodium hydrogen carbonate |
| Na$_2$SO$_4$ | Sodium sulfate |
| Cs$_2$CO$_3$ | Caesium carbonate |
| TEA | Triethylamine |
| TFA | Trifluoroacetic acid |
| THF | Tetrahydrofuran |
| RT | Room temperature |
| ZnCl$_2$ | Zinc chloride |
| PPTS | Pyridinium para-toluenesulfonate |
| anh. | Anhydrous |
| Pd-C | Palladium-on-charcoal |
| CuI | Copper iodide |
| MeCN | Acetonitrile |
| NaI | Sodium iodide |
| DIEA | Diisopropylethylamine |
| TBTU | O-(Benzotriazol-1-yl)-N,N,N',N'-tetramethyluronium tetrafluoroborate |
| DCC | N, N-Dicyclohexylacarbodiimide |
| NMM | 4-Methylmorpholine |
| NMO | 4-methylmorpholine N-oxide |
| OsO$_4$ | Osmium tetroxide |
| Pd(OAc)$_2$ | Palladium acetate |
| P(OTol)$_3$ | Tri(o-tolyl)phosphine |
| pTsOH | para-Toluenesulfonic acid |
| Tr | Retention time |
| T | Time |
| T ° C. | Temperature in ° C. |
| Min | Minutes |
| m.p. | Melting point |

The proton magnetic resonance (1H NMR) spectra, as described below, are recorded at 400 MHz in DMSO-d6, using the peak of DMSO-d5 as reference. The chemical shifts δ are expressed in parts per million (ppm). The signals observed are expressed as follows: s=singlet; bs=broad singlet; d=doublet; dd=doublet of doublets; dt=doublet of triplets; t=triplet; m=multiplet; H=proton.

The mass spectra are obtained under the following LC/MS coupling conditions:
Method 1: Column: Jsphere 33×2 mm; 4 μM;
Eluents: A=H$_2$O+0.05% TFA; B=CH$_3$CN+0.05% TFA
T0: 98% A; T1.0 to T5.0 min: 95% B;
Method 2: Column: Acquity BEH C18 (50×2.1 mm; 1.7 μM);
Eluents: A=H$_2$O+0.05% TFA; B=CH$_3$CN+0.035% TFA.
T0: 98% A; T1.6 to T2.1 min: 100% B; T2.5 to T3 min: 98% A
flow rate 1.0 mL/min; T° C.=40° C., injection 2 μL
Method 3: Column: Kromasil C18 (50×2.1 mm; 3.5 μm);
Eluents: A=CH$_3$CO$_2$NH$_4$+3% CH$_3$CN; B=CH$_3$CN;
T0: 100% A; T5.5 to 17 min: 100% B; T7.1 to T10 min: 100% B; flow rate 0.8 mL/min ; T°=40° C.–Injection 5 μL.

EXAMPLE 1

N-ethyl-6-[3-methyl-4-(1-methyl-1-phenylethyl)-5-oxo-2,5-dihydro-1H-pyrazol-1-yl]-N-phenylpyridine-3-sulfonamide (Compound 77 of Table I)

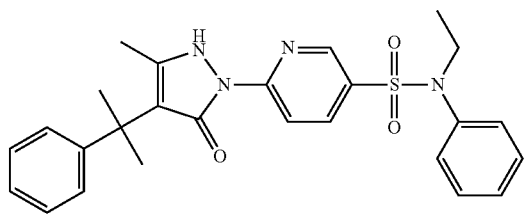 [SMILES: CCN(c1ccccc1)S(=O)(=O)c1ccc(-n2[nH]c(C)c(C(C)(C)c3ccccc3)c2=O)nc1]

1.1. methyl 2-acetyl-3-methylbut-2-enoate

To a mixture of 9.54 g (70 mmol) of anhydrous ZnCl$_2$, 53.9 mL (500 mmol) of methyl acetoacetate and 55 mL (750 mmol) of acetone are added 64 mL of acetic anhydride. The reaction medium is then heated for 3 days at 50° C., and then diluted with 1 L of DCM and washed with water (3×100 mL). The organic phase is dried over Na$_2$SO$_4$, filtered and then concentrated under reduced pressure. The residue obtained is purified by chromatography on a column of silica gel, eluting with a cyclohexane/EtOAc gradient of 0 to 10% EtOAc. After concentrating under reduced pressure, 51.5 g of methyl 2-acetyl-3-methylbut-2-enoate are obtained in the form of a colourless oil.
Yield=70%
$^1$H NMR, CDCl$_3$, 400 MHz, δ (ppm): 3.79 (s, 3H); 2.29 (s, 3H); 2.12 (s, 3H); 1.97 (s, 3H).

1.2. methyl 2-acetyl-3-methyl-3-phenylbutanoate

To a suspension of 146 mg (0.8 mmol) of anhydrous CuI (I) in 5 mL of anhydrous ether are added, at 0° C., under a stream of argon, 3.6 mL (10.9 mmol) of a 3M solution of phenyl magnesium bromide in Et$_2$O. After stirring for 30 minutes at 0° C., 1 g (6.4 mmol) of methyl 2-acetyl-3-methylbut-2-enoate is added in a single portion. The mixture is allowed to warm to room temperature and stirring is continued for 18 hours. The reaction mixture is then treated with 100 mL of saturated NH$_4$Cl solution, the phases are separated by settling, and the organic phase is again treated with 100 mL of saturated NH$_4$Cl solution. The aqueous phases are extracted with 4×100 mL of DCM. The organic phases are combined, dried over anhydrous Na$_2$SO$_4$ and concentrated under reduced pressure. After purification by chromatography on silica gel, eluting with a 95/5 cyclohexane/EtOAc mixture, 1 g of methyl 2-acetyl-3-methyl-3-phenylbutanoate is obtained in the form of a colourless oil.
Yield=67%.
$^1$H NMR, CDCl$_3$, 400 MHz, δ (ppm): 7.4-7.2 (m, 5H); 3.9 (s, 1H); 3.8 (s, 3H); 1.90 (s, 3H); 1.6 (s, 3H), 1.55 (s, 3H).

1.3. N-ethyl-6-[3-methyl-4-(1-methyl-1-phenylethyl)-5-oxo-2,5-dihydro-1H-pyrazol-1-yl]-N-phenylpyridine-3-sulfonamide To a solution of 200 mg (0.85 mmol) of methyl 2-acetyl-3-methyl-3-phenylbutanoate in 2 mL of EtOH/AcOH mixture (1:1) are added 249 mg (0.85 mmol) of N-ethyl-6-hydrazino-N-phenylpyridine-3-sulfonamide and the reaction mixture is then heated for 2 hours at 90° C. After concentrating under reduced pressure, the residue is taken up in 100 mL of DCM, washed with 2×30 mL of saturated NaHCO$_3$ solution, dried over Na$_2$SO$_4$, filtered, concentrated under reduced pressure and then purified by chromatography on a column of silica gel, eluting with a cyclohexane/EtOAc gradient of 0 to 20% EtOAc. After concentrating under reduced pressure, 312 mg of a yellow oil are obtained, and are solidified in 20 mL of pentane. The solid obtained is filtered off, and then dried under vacuum. 178 mg of N-ethyl-6-[3-methyl-4-(1-methyl-1-phenylethyl)-5-oxo-2,5-dihydro-1H-pyrazol-1-yl]-N-phenylpyridine-3-sulfonamide are obtained in the form of a white powder.
Yield=44%
m.p. (° C.)=122
M=C$_{26}$H$_{28}$N$_4$O$_3$S=476; M+H=477; Method 2: Tr=1.54 min
$^1$H NMR, d6-DMSO, 400 MHz, δ (ppm): 12.0 (bs, 1H); 8.55 (bs, 1H); 8.45 (s, 1H); 8.1 (d, 1H); 7.5-7.3 (m, 7H); 7.2 (m, 1H); 7.1 (d, 2H); 3.65 (q, 2H); 1.9 (s, 3H); 1.7 (s, 6H); 1.0 (t, 3H).

EXAMPLE 2

N-ethyl-6-[(3-methyl-5-oxo-4-(pyridin-3-ylmethyl)-2,5-dihydro-1H-pyrazol-1-yl]N-phenylpyridine-3-sulfonamide (Compound 43 of Table I)

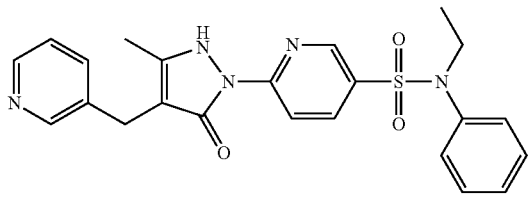 [SMILES: CCN(c1ccccc1)S(=O)(=O)c1ccc(-n2[nH]c(C)c(Cc3cccnc3)c2=O)nc1]

2.1. methyl (2E/Z)-3-oxo-2-(pyridin-3-ylmethylidene)butanoate

A mixture of 10 g (86 mmol) of methyl 3-oxobutanoate, 9.2 g (86 mmol) of pyridine-2-carboxaldehyde and 70 mg (1.1 mmol) of PPTS in 27 mL of hexane is refluxed for 48 hours in Dean-Stark apparatus. The medium is then concentrated under reduced pressure, taken up in 50 mL of EtOAc, washed successively with water (2×100 mL) and brine (100 mL), dried over Na$_2$SO$_4$, filtered and concentrated under reduced pressure. 17.6 g of methyl (2E/Z)-3-oxo-2-(pyridin-3-ylmethylidene)butanoate are obtained in the form of a yellow oil, which is used without further purification for the following step.

Yield=99%.

¹H NMR, CDCl₃, 400 MHz, δ (ppm): 8.7 (s, 1H); 8.5 (d, 1H); 8.00 (d, 1H); 7.6 (s, 1H); 7.35 (dd, 1H); 3.7 (s, 3H); 2.3 (s, 3H).

2.2. methyl 3-oxo-2-(pyridin-3-ylmethyl)butanoate

In Parr apparatus, a mixture of 14 g (68 mmol) of methyl (2E/Z)-3-oxo-2-(pyridin-3-ylmethylidene)butanoate in 200 mL of MeOH and 2.2 g of 10% Pd/C is hydrogenated for 48 hours at 7 bar. The reaction mixture is then filtered through Whatman GF/F paper and concentrated under reduced pressure. 14 g of methyl 3-oxo-2-(pyridin-3-ylmethyl)butanoate are thus obtained in the form of a dark yellow oil, which is used without further purification in the following step.

Yield=99%.

¹H NMR, CDCl₃, 400 MHz, δ (ppm): 8.5 (m, 2H); 7.28 (d, 1H); 7.21 (dd, 1H); 3.78 (t, 1H); 3.71 (s, 3H); 3.16 (dd, 2H); 2.23 (s, 3H).

2.3 N-ethyl-6-[3-methyl-5-oxo-4-(pyridin-3-ylmethyl)-2,5-dihydro-1H-pyrazol-1-yl]-N-phenylpyridine-3-sulfonamide hydrochloride A solution of 300 mg (1.45 mmol) of methyl 3-oxo-2-(pyridin-3-ylmethyl)butanoate and 423 mg (1.45 mmol) of N-ethyl-6-hydrazino-N-phenylpyridine-3-sulfonamide in 4 mL of EtOH/AcOH mixture (1/1) is heated for 4 hours at 85° C. After cooling to room temperature, the precipitate obtained is filtered off and then washed successively with Et₂O (20 mL) and pentane (20 mL). 210 mg of a residue are isolated, and this residue is taken up in 40 mL of water, 2 mL of acetonitrile and 0.48 mL of 0.2N HCl solution and then freeze-dried. 220 mg of N-ethyl-6-[3-methyl-5-oxo-4-(pyridin-3-ylmethyl)-2,5-dihydro-1H-pyrazol-1-yl]-N-phenylpyridine-3-sulfonamide hydrochloride are thus obtained in the form of a white lyophilizate.

Yield=33% m.p. (° C.)=128

M=$C_{23}H_{23}N_5O_3S$=449; M+H=450; Method 2: Tr=0.85 min

¹H NMR, d6-DMSO, 400 MHz, δ (ppm): 12.5 (bs, 1H); 8.90 (s, 1H); 8.8 (d, 1H); 8.6 (d, 1H); 8.5 (d, 1H); 8.4 (s, 1H); 8.2 (dd, 1H); 8.05 (dd, 1H); 7.4 (m, 3H); 7.1 (d, 2H); 3.8 (s, 2H); 3.65 (q, 2H); 2.3 (s, 3H); 1.0 (t, 3H).

EXAMPLE 3

6-(4-{3-[2-(dimethylamino)ethoxy]benzyl}-3-methyl-5-oxo-2,5-dihydro-1H-pyrazol-1-yl)-N-ethyl-N-phenylpyridine-3-sulfonamide hydrochloride (Compound 56 of Table I)

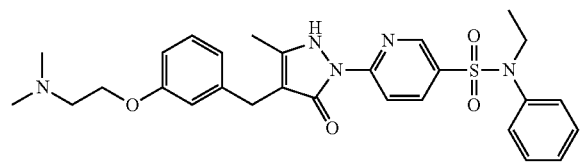 [SMILES: CCN(c1ccccc1)S(=O)(=O)c1ccc(-n2[nH]c(C)c(Cc3cccc(OCCN(C)C)c3)c2=O)nc1]

3.1. methyl (2E/Z)-2-[(3-hydroxyphenyl)methylidene]-3-oxobutanoate

According to the process described in Example 2.1, starting with 5 g of 3-hydroxybenzaldehyde and 4.75 g of methyl 3-oxobutanoate, 2.5 g of methyl (2E/Z)-2-[(3-hydroxyphenyl)methylidene]-3-oxobutanoate are obtained in the form of a pale yellow powder.

Yield=27%

¹H NMR (CDCl₃, 400 MHz, δ (ppm): 7.4 (s, 1H); 7.2 (m, 1H); 6.9-6.8 (m, 2H); 5.1 (s, 1H); 3.8 (s, 3H); 2.4 (s, 3H); 2.4 (s, 3H).

3.2. methyl 2-(3-hydroxybenzyl)-3-oxobutanoate

According to the process described in Example 2.2, starting with 2.5 g of methyl (2E/Z)-2-[(3-hydroxyphenyl)methylidene]-3-oxobutanoate, 2.5 g of methyl 2-(3-hydroxybenzyl)-3-oxobutanoate are obtained in the form of a translucent wax.

Yield=99%

¹H NMR CDCl₃, 400 MHz, δ (ppm): 7.15 (t, 1H); 6.7-6.85 (m, 3H); 5.6 (s, 1H); 3.7 (s, 3H); 3.15 (d, 2H); 2.25 (s, 3H).

3.3. methyl 2-{3-[2-(dimethylamino)ethoxy]benzyl}-3-oxobutanoate

A mixture of 1.5 g (6.75 mmol) of methyl 2-(3-hydroxybenzyl)-3-oxobutanoate, 6.6 g (20.25 mmol) of anhydrous Cs₂CO₃, 0.1 g (0.67 mmol) of NaI and 1 g (7.1 mmol) of 2-dimethylaminoethyl chloride hydrochloride in 20 mL of anhydrous CH₃CN is heated for 4 hours at 90° C., and then stirred overnight at room temperature. The reaction medium is filtered and then concentrated under reduced pressure. The residue obtained is taken up in DCM (100 mL), washed with brine (30 mL), dried over Na₂SO₄, filtered, concentrated under reduced pressure and then purified by chromatography on a column of silica gel, eluting with a DCM/MeOH gradient of 0 to 10% MeOH. After concentrating under reduced pressure, 409 mg of methyl 2-{3-[2-(dimethylamino)ethoxy]benzyl}-3-oxobutanoate are obtained in the form of a brown wax.

Yield=19.5%

¹H NMR (CDCl₃, 400 MHz, δ (ppm): 7.2 (t, 1H); 6.7-6.8 (m, 3H); 4.1 (t, 2H); 3.8 (t, 1H); 3.7 (s, 3H); 3.15 (d, 2H); 2.8 (t, 2H); 2.4 (s, 6H); 2.3 (s, 3H).

3.4. 6-(4-{3-[2-(dimethylamino)ethoxy]benzyl}-3-methyl-5-oxo-2,5-dihydro-1H-pyrazol-1-yl)-N-ethyl-N-phenylpyridine-3-sulfonamide hydrochloride According to the process described in Example 2.3, starting with 195 mg of methyl 2-{3-[2-(dimethylamino)ethoxy]benzyl}-3-oxobutanoate and 194 mg of N-ethyl-6-hydrazino-N-phenylpyridine-3-sulfonamide, 70 mg of 6-(4-{3-[2-(dimethylamino)ethoxy]benzyl}-3-methyl-5-oxo-2,5-dihydro-1H-pyrazol-1-yl)-N-ethyl-N-phenylpyridine-3-sulfonamide hydrochloride are obtained in the form of a white lyophilizate.

Yield=20% m.p. (° C.)=124

M=$C_{28}H_{33}N_5O_4S$=535; M+H=536; Method 2: Tr=0.98 min

¹H NMR, d6-DMSO, 400 MHz, δ (ppm): 12.0 (bs, 1H); 10.0 (bs, 1H); 8.6 (d, 1H); 8.4 (s, 1H); 8.1 (d, 1H); 7.4 (m, 3H);

7.25 (t, 1H); 7.15 (d, 2H); 6.9 (d, 2H); 6.8 (d, 1H); 4.3 (t, 2H); 3.6 (q, 2H); 3.5 (s, 2H); 3.4 (t, 2H); 2.8 (s, 6H); 2.2 (s, 3H); 1.0 (t, 3H).

EXAMPLE 4

6-{4-[3-(dimethylamino)benzyl]-3-methyl-5-oxo-2,5-dihydro-1H-pyrazol-1-yl}-N-ethyl-N-phenylpyridine-3-sulfonamide (Compound 53 of Table I)

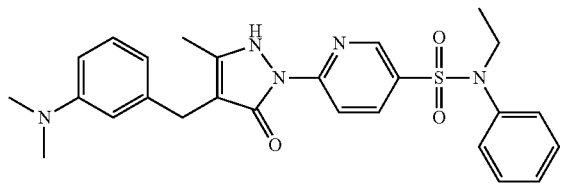 [SMILES: CCN(c1ccccc1)S(=O)(=O)c1ccc(-n2[nH]c(C)c(Cc3cccc(N(C)C)c3)c2=O)nc1]

4.1. methyl (2Z/E)-2-[(4-nitrophenyl)methylidene]-3-oxobutanoate

According to the process described in Example 2.1, starting with 6.18 g of 4-nitrobenzaldehyde and 4.75 g of methyl 3-oxobutanoate, 4.2 g of methyl (2Z/E)-2-[(4-nitrophenyl)methylidene]-3-oxobutanoate are obtained in the form of an oil.
Yield=41%
$^{1}$H NMR, CDCl$_{3}$, 400 MHz, δ (ppm): 8.4 (s, 1H); 8.3 (d, 1H); 7.8 (d, 1H); 7.6 (m, 2H); 3.9 (s, 3H); 2.5 (s, 3H).

4.2. methyl 2-(4-aminobenzyl)-3-oxobutanoate

According to the process described in Example 2.2, starting with 4.2 g of methyl (2Z/E)-2-[(4-nitrophenyl)methylidene]-3-oxobutanoate, 2 g of methyl 2-(4-aminobenzyl)-3-oxobutanoate are obtained in the form of an oil.
$^{1}$H NMR, CDCl$_{3}$, 400 MHz, δ (ppm): 7.1 (t, 1H); 6.6-6.5 (m, 3H); 3.9 (t, 1H); 3.8 (s, 3H); 3.7 (bs, 2H); 3.1 (d, 2H); 2.2 (s, 3H).
Yield=54%

4.3. methyl 2-[4-(dimethylamino)benzyl]-3-oxobutanoate

To a mixture of 1.5 g (6.78 mmol) of methyl 2-(4-aminobenzyl)-3-oxobutanoate, 40 μl (0.04 mmol) of AcOH and 5.1 mL (67.8 mmol) of an aqueous 37% solution of formaldehyde in 13 mL of CH$_{3}$CN are added portionwise at 0° C. 4.3 g (20.34 mmol) of sodium triacetoxyborohydride. The reaction medium is then allowed to warm slowly to room temperature, and stirring is continued for 12 hours. The reaction mixture is poured into 50 mL of saturated NaHCO$_{3}$ solution and 30 g of ice, extracted with EtOAc (2×100 mL), dried over Na$_{2}$SO$_{4}$, filtered and concentrated under reduced pressure, and then purified by chromatography on a column of silica gel, eluting with a cyclohexane/EtOAc gradient of 0 to 50% EtOAc. 344 mg of methyl 2-[4-(dimethylamino)benzyl]-3-oxobutanoate are obtained in the form of a yellow oil.
Yield: 20%
$^{1}$H NMR, CDCl$_{3}$, 400 MHz, δ (ppm): 7.1 (t, 1H); 6.65 (d, 1H); 6.55 (m, 2H); 3.9 (t, 1H); 3.8 (s, 3H); 3.2 (d, 2H); 3.0 (s, 6H); 2.2 (s, 3H).

4.4. 6-{4-[3-(dimethylamino)benzyl]-3-methyl-5-oxo-2,5-dihydro-1H-pyrazol-1-yl}-N-ethyl-N-phenylpyridine-3-sulfonamide According to the process described in Example 1.3, starting with 172 mg of methyl 2-[4-(dimethylamino)benzyl]-3-oxobutanoate and 202 mg of N-ethyl-6-hydrazino-N-phenylpyridine-3-sulfonamide, 138 mg of 6-{4-[3-(dimethylamino)benzyl]-3-methyl-5-oxo-2,5-dihydro-1H-pyrazol-1-yl}-N-ethyl-N-phenylpyridine-3-sulfonamide are obtained in the form of a white solid.
Yield=41%
m.p. (° C.)=122
M=C$_{26}$H$_{29}$N$_{5}$O$_{3}$S=491; M+H=492; Method 2: Tr=0.96
$^{1}$H NMR, d6-DMSO, 400 MHz, δ (ppm): 12.0 (bs, 1H); 8.7 (bs, 1H); 8.45 (s, 1H); 8.1 (d, 1H); 7.4 (m, 3H); 7.2 (d, 2H); 7.1 (t, 1H); 6.7 (s, 1H); 6.5 (d, 2H); 3.7 (q, 2H); 3.5 (s, 2H); 2.9 (s, 6H); 2.15 (s, 3H); 1.0 (t, 3H).

EXAMPLE 5

N,N-dimethyl-6-[3-methyl-5-oxo-4-(pyridin-3-ylmethyl)-2,5-dihydro-1H-pyrazol-1-yl]pyridine-3-sulfonamide (Compound 66 of Table I)

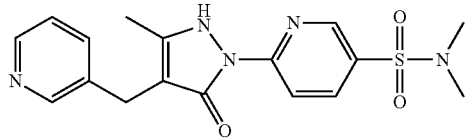 [SMILES: Cc1[nH]n(-c2ccc(S(=O)(=O)N(C)C)cn2)c(=O)c1Cc1cccnc1]

5.1. 6-chloro-N,N-dimethylpyridine-3-sulfonamide

To a mixture of 4.7 mL (9.43 mmol) of dimethylamine (2N in THF) and 2.6 mL (18.86 mmol) of TEA in 20 mL of THF is added dropwise, at 0° C., a solution of 2 g (9.43 mmol) of 6-chloropyridine-3-sulfonyl chloride (prepared according to patent WO 9840332) in 5 mL of THF. After stirring for 40 minutes at 0° C., the reaction medium is taken up in 40 mL of EtOAc, washed with water (2×40 mL) and brine (40 mL), dried over Na$_{2}$SO$_{4}$, filtered and concentrated under reduced pressure. 1.93 g of 6-chloro-N,N-dimethylpyridine-3-sulfonamide are obtained in the form of a brown solid, which is used without further purification in the following step.
Yield=93%
$^{1}$H NMR, CDCl$_{3}$, 400 MHz, δ (ppm): 8.8 (s, 1H); 8.0 (d, 1H); 7.4 (d, 1H); 2.7 (s, 6H).

5.2. 6-hydrazino-N,N-dimethylpyridine-3-sulfonamide

A mixture of 1.9 g (8.8 mmol) of 6-chloro-N,N-dimethylpyridine-3-sulfonamide and 4.6 mL (91.5 mmol) of hydrazine monohydrate in 10 mL of EtOH is heated for 2 hours at 80° C. The precipitate obtained, after cooling to room temperature, is filtered off and then washed with 10 mL of EtOH and dried under vacuum. 1.62 g of 6-hydrazino-N,N-dimethylpyridine-3-sulfonamide are obtained in the form of a white powder.
$^{1}$H NMR, d6-DMSO, 400 MHz, δ (ppm): 8.5 (bs, 1H); 8.3 (s, 1H); 7.7 (d, 1H); 6.85 (d, 1H); 4.4 (s, 2H); 2.6 (s, 6H).

5.3. N,N-dimethyl-6-[3-methyl-5-oxo-4-(pyridin-3-ylmethyl)-2,5-dihydro-1H-pyrazol-1-yl]pyridine-3-sulfonamide A mixture of 400 mg (1.85 mmol) of 6-hydrazino-N,N-dimethylpyridine-3-sulfonamide and 383 mg (1.85 mmol) of methyl 3-oxo-2-(pyridin-3-ylmethyl)butanoate in 4 mL of EtOH/AcOH mixture (1:1) is heated for 4 hours at 80° C. and then concentrated under reduced pressure. The residue obtained is taken up in 20 mL of EtOAc, washed successively with water (2×20 mL), saturated NaHCO$_3$ solution (20 mL) and brine (20 mL), dried over Na$_2$SO$_4$, filtered and concentrated under reduced pressure. The residue is then solidified in 20 mL of an Et$_2$O/pentane mixture (1/1), filtered and recrystallized from a cyclohexane/EtOH mixture. 188 mg of N,N-dimethyl-6-[3-methyl-5-oxo-4-(pyridin-3-ylmethyl)-2,5-dihydro-1H-pyrazol-1-yl]pyridine-3-sulfonamide are obtained in the form of white crystals.

Yield=28%
m.p. (° C.)=212
M=C$_{17}$H$_{19}$N$_5$O$_3$S=373; M+H=374; Method 2: Tr=0.58 min
$^1$H NMR, d6-DMSO, 400 MHz, δ (ppm): 12 (bs, 1H); 8.7 (s, 1H); 8.65 (d, 1H); 8.5 (s, 1H); 8.4 (d, 1H); 8.35 (d, 1H); 7.7 (d, 1H); 7.3 (dd, 1H); 3.6 (s, 2H); 2.7 (s, 6H); 2.2 (s, 3H).

EXAMPLE 6

N-ethyl-6-{4-[3-(methoxymethyl)benzyl]-3-methyl-5-oxo-2,5-dihydro-1H-pyrazol-1-yl}-N-phenylpyridine-3-sulfonamide (Compound 34 of Table I)

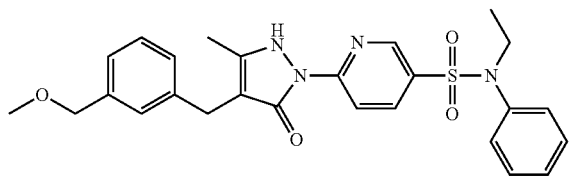 [SMILES: CCN(c1ccccc1)S(=O)(=O)c1ccc(-n2[nH]c(C)c(Cc3cccc(COC)c3)c2=O)nc1]

6.1. methyl 3-(methoxymethyl)benzoate

To a solution of 15 g (65.5 mmol) of methyl 3-(bromomethyl)benzoate in 20 mL of anhydrous MeOH is added dropwise, at room temperature, a solution of sodium methoxide in MeOH, prepared beforehand from 2.25 g (98.2 mmol) of sodium in 65 mL of MeOH. The reaction medium is then heated for 4 hours at 65° C. and then concentrated under reduced pressure, taken up in 500 mL of DCM, washed with water (100 mL) and brine (100 mL), dried over Na$_2$SO$_4$, filtered and concentrated under reduced pressure. 7.8 g of methyl 3-(methoxymethyl)benzoate are obtained in the form of an oil, which is used without further purification in the following step.

Yield=66%
$^1$H NMR, CDCl$_3$, 400 MHz, δ (ppm): 8.1 (s, 1H); 8.0 (d, 1H); 7.5 (d, 1H); 7.4 (t, 1H); 4.5 (s, 2H); 4.0 (s, 3H); 3.4 (s, 3H).

6.2. 2-[3-(methoxymethyl)phenyl]methanol

To a solution of 7.8 g (43.3 mmol) of methyl 3-(methoxymethyl)benzoate in 60 mL of a THF/dioxane mixture (1/1) is added 0.94 g (43.3 mmol) of lithium borohydride. The reaction medium is then heated for 3 hours at 80° C. and stirred overnight at room temperature. The reaction medium is taken up in 500 mL of EtOAc, washed with water (2×100 mL), dried over Na$_2$SO$_4$, filtered and concentrated under reduced pressure. 5.9 g of 2 [3-(methoxymethyl)phenyl]methanol are obtained in the form of a yellow liquid, which is used without further purification in the following step.

Yield=90%
$^1$H NMR, CDCl$_3$, 400 MHz, δ (ppm): 7.4-7.2 (m, 4H); 4.7 (s, 2H); 4.5 (s, 2H); 3.4 (s, 3H); 2.4 (bs, 1H).

6.3. 1-(bromomethyl)-3-(methoxymethyl)benzene

To a solution of 5.91 g (38.8 mmol) of 2 [3-(methoxymethyl)phenyl]methanol in 75 mL of Et$_2$O are added dropwise, at 0° C., 9.1 mL (97.1 mmol) of phosphorus tribromide. The reaction mixture is allowed to warm slowly to room temperature and stirring is continued for 4 hours. The crude reaction mixture is then poured cautiously into a mixture of 100 g of ice and 100 mL of MeOH. After evaporating off the MeOH under reduced pressure, the aqueous phase is extracted with DCM (2×200 mL). The organic phases are combined, dried over Na$_2$SO$_4$, filtered and then concentrated under reduced pressure. The residue obtained is purified by chromatography on a column of silica gel, eluting with a cyclohexane/EtOAc gradient of 0 to 20% EtOAc. 3.25 g of 1-(bromomethyl)-3-(methoxymethyl)benzene are thus obtained in the form of an oil.

Yield=39%
$^1$H NMR CDCl$_3$, 400 MHz, δ (ppm): 7.4-7.1 (m, 4H); 4.45 (s, 2H); 4.35 (s, 2H); 3.3 (s, 3H).

6.4. methyl 2-[3-(methoxymethyl)benzyl]-3-oxobutanoate

To a solution of 0.34 g (15.1 mmol) of sodium in 8 mL of anhydrous MeOH are added dropwise, at room temperature and under argon, 1.6 mL (15.1 mmol) of methyl acetoacetate. After stirring for 30 minutes, 3.25 g (15.11 mmol) of 1-(bromomethyl)-3-(methoxymethyl)benzene are rapidly added dropwise and the reaction medium is then heated for 2 hours 30 minutes at 70° C. The reaction medium is then concentrated under reduced pressure, and the residue obtained is purified by chromatography on a column of silica gel, eluting with a cyclohexane/EtOAc gradient of 0 to 20% EtOAc. 3.2 g of methyl 2-[3-(methoxymethyl)benzyl]-3-oxobutanoate are obtained in the form of an oil.

Yield=85%
$^1$H NMR, CDCl$_3$, 400 MHz, δ (ppm): 7.4-7.1 (m, 4H); 4.45 (s, 2H); 3.8 (t, 1H); 3.7 (t, 3H); 3.4 (t, 3H); 3.2 (d, 2H); 2.2 (s, 3H).

6.5. N-ethyl-6-{4-[3-(methoxymethyl)benzyl]-3-methyl-5-oxo-2,5-dihydro-1H-pyrazol-1-yl}-N-phenylpyridine-3-sulfonamide According to the process described in Example 1.3, starting with 300 mg of methyl 2-[3-(methoxymethyl)benzyl]-3-oxobutanoate and 350 mg of N-ethyl-6-hydrazino-N-phenylpyridine-3-sulfonamide, 341 mg of N-ethyl-6-{4-[3-(methoxymethyl)benzyl]-3-methyl-5-oxo-2,5-dihydro-1H-pyrazol-1-yl}-N-phenylpyridine-3-sulfonamide are obtained in the form of a white powder.

Yield=58%
m.p. (° C.)=144
M=C$_{26}$H$_{28}$N$_4$O$_4$S=492; M+H=493; Method 2: Tr=1.29 min.
$^1$H NMR, d6-DMSO, 400 MHz, δ (ppm): 12.0 (bs, 1H); 8.7 (bs, 1H); 8.45 (s, 1H); 8.1 (d, 1H); 7.4 (m, 3H); 7.3-7.1 (m, 6H); 4.35 (s, 2H); 3.6 (q, 2H); 3.5 (s, 2H); 3.3 (s, 3H); 2.15 (s, 3H); 1.0 (t, 3H).

EXAMPLE 7

N-ethyl-6-[3-methyl-5-oxo-4-(2-phenylethyl)-2,5-dihydro-1H-pyrazol-1-yl]-N-phenylpyridine-3-sulfonamide (Compound 74 of Table I)

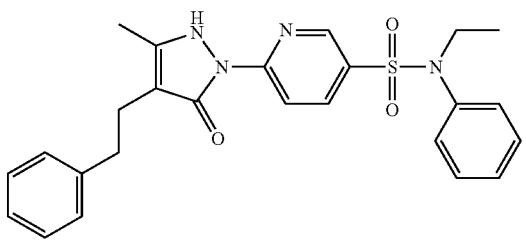 [SMILES: CCN(c1ccccc1)S(=O)(=O)c1ccc(-n2[nH]c(C)c(CCc3ccccc3)c2=O)nc1]

7.1. methyl 3-oxo-2-(2-phenylethyl)butanoate

According to the process described in Example 6.4, starting with 5.16 g of (2-bromoethyl)benzene and 3.2 g of methyl acetoacetate, 1.9 g of methyl 3-oxo-2-(2-phenylethyl)butanoate are obtained in the form of a translucent oil.
Yield=31%.
$^1$H NMR, CDCl$_3$, 400 MHz, δ (ppm): 7.2-7.35 (m, 5H); 3.75 (s, 3H); 3.5 (t, 1H); 2.5-2.7 (m, 2H); 2.2 (s, 3H); 2.15-2.3 (m, 2H).

7.2. N-ethyl-6-[3-methyl-5-oxo-4-(2-phenylethyl)-2,5-dihydro-1H-pyrazol-1-yl]-N-phenylpyridine-3-sulfonamide According to the process described in Example 1.3, starting with 264 mg of methyl 3-oxo-2-(2-phenylethyl)butanoate and 351 mg of N-ethyl-6-hydrazino-N-phenylpyridine-3-sulfonamide, 291 mg of N-ethyl-6-[3-methyl-5-oxo-4-(2-phenylethyl)-2,5-dihydro-1H-pyrazol-1-yl]-N-phenylpyridine-3-sulfonamide are obtained in the form of a white powder.
Yield=53%
m.p. (° C.)=158
M=C$_{25}$H$_{26}$N$_4$O$_3$S=462; M+H=463; Method 2=1.35 min
$^1$H NMR, d6-DMSO, 400 MHz, δ (ppm): 11.8 (bs, 1H); 8.6 (bs, 1H); 8.45 (s, 1H); 8.1 (d, 1H); 7.4 (m, 3H); 7.3 (m, 2H); 7.2 (d, 3H); 7.1 (d, 2H); 3.6 (q, 2H); 2.8 (t, 2H); 2.5 (t, 2H); 1.9 (s, 3H); 1.0 (t, 3H).

EXAMPLE 8

6-(4-benzyl-5-oxo-3-propyl-2,5-dihydro-1H-pyrazol-1-yl)-N-ethyl-N-phenylpyridine-3-sulfonamide (Compound 68 of Table I)

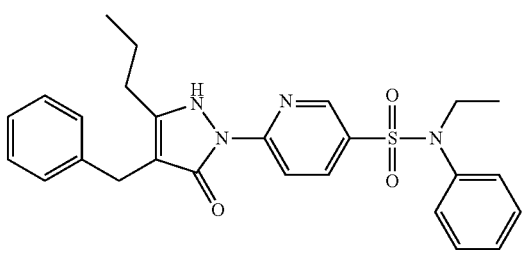 [SMILES: CCCc1[nH]n(-c2ccc(S(=O)(=O)N(CC)c3ccccc3)cn2)c(=O)c1Cc1ccccc1]

8.1. ethyl 2-benzyl-3-oxohexanoate

According to the process described in Example 6.4, starting with 2.2 g of benzyl bromide and 4 g of ethyl butyrylacetate, 2.5 g of ethyl 2-benzyl-3-oxohexanoate are obtained in the form of a translucent oil.
Yield=40%
$^1$H NMR, CDCl$_3$, 400 MHz, δ (ppm): 7.15-7.30 (m, 5H); 4.2 (q, 2H); 3.8 (t, 1H); 3.2 (dd, 2H); 2.5-2.3 (m, 2H); 1.55 (m, 2H); 1.2 (t, 3H); 0.86 (t, 3H).

8.2. 6-(4-benzyl-5-oxo-3-propyl-2,5-dihydro-1H-pyrazol-1-yl)-N-ethyl-N-phenylpyridine-3-sulfonamide According to the process described in Example 1.3, starting with 300 mg of ethyl 2-benzyl-3-oxohexanoate and 353 mg of N-ethyl-6-hydrazino-N-phenylpyridine-3-sulfonamide, 400 mg of 6-(4-benzyl-5-oxo-3-propyl-2,5-dihydro-1H-pyrazol-1-yl)-N-ethyl-N-phenylpyridine-3-sulfonamide are obtained in the form of a white powder.
Yield=69%
m.p. (° C.)=180
M=C$_{26}$H$_{28}$N$_4$O$_3$S=476; M+H=477; Method 2: Tr=1.45 min.
$^1$H NMR, d6-DMSO, 400 MHz, δ (ppm): 12.0 (bs, 1H); 8.6 (bs, 1H); 8.45 (s, 1H); 8.1 (d, 1H); 7.45-7.1 (m, 10H); 3.65 (q, 2H); 3.6 (s, 2H); 2.5 (t, 2H); 1.5 (m, 2H); 1.0 (t, 3H); 0.9 (t, 3H).

EXAMPLE 9

N-ethyl-6-{4-[3-(2-methoxyethoxy)benzyl]-3-methyl-5-oxo-2,5-dihydro-1H-pyrazol-1-yl}-N-phenylpyridine-3-sulfonamide (Compound 38 of Table I)

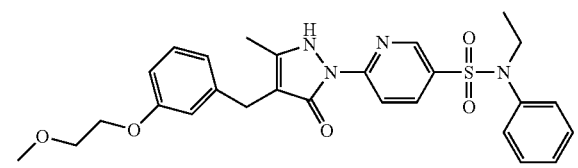 [SMILES: CCN(c1ccccc1)S(=O)(=O)c1ccc(-n2[nH]c(C)c(Cc3cccc(OCCOC)c3)c2=O)nc1]

9.1. [3-(2-methoxyethoxy)phenyl]methanol

A mixture of 10 g (80.6 mmol) of 3-(hydroxymethyl)phenol, 78.4 g (241.7 mmol) of Cs$_2$CO$_3$ and 8.4 mL (88.6 mmol) of bromoethyl methyl ether in 150 mL of CH$_3$CN is heated for 12 hours at 110° C. After cooling to room temperature, the medium is filtered, concentrated under reduced pressure, taken up in 500 mL of DCM, washed with brine (2×100 mL) dried over Na$_2$SO$_4$, filtered and then concentrated under reduced pressure. 10.9 g of 3-(2-methoxyethoxy)phenyl]methanol are obtained in the form of a yellow oil.
Yield=75%
$^1$H NMR, CDCl$_3$, 400 MHz, δ (ppm): 7.3 (t, 1H); 6.95 (m, 2H); 6.85 (d, 1H); 4.6 (s, 2H); 4.1 (t, 2H); 3.8 (t, 2H); 3.4 (s, 3H); 2.1 (bs, 1H)

9.2. 1-(bromomethyl)-3-(2-methoxyethoxy)benzene

According to the process described in Example 6.3, starting with 10 g of [3-(2-methoxyethoxy)phenyl]methanol, 11.8 g of 1-(bromomethyl)-3-(2-methoxyethoxy)benzene are obtained in the form of an oil.

Yield=87%

¹H NMR, CDCl₃, 400 MHz, δ (ppm): 7.3 (m, 1H); 7.0 (m, 2H); 6.9 (d, 1H); 4.45 (s, 2H); 4.15 (t, 2H); 3.75 (t, 2H); 3.4 (s, 3H)

9.3. methyl 2-[3-(2-methoxyethoxy)benzyl]-3-oxobutanoate

According to the process described in Example 6.4, starting with 5.6 g of 1-(bromomethyl)-3-(2-methoxyethoxy)benzene and 2.52 g of methyl acetoacetate, 3.44 g of methyl 2-[3-(2-methoxyethoxy)benzyl]-3-oxobutanoate are obtained in the form of a yellow oil.

¹H NMR CDCl₃, 400 MHz, δ (ppm): 7.2 (t, 1H); 6.75 (m, 3H); 4.15 (d, 2H); 3.8 (t, 1H); 3.75 (s, 3H); 3.45 (s, 3H); 3.15 (d, 2H); 2.2 (s, 3H).

9.4. N-ethyl-6-{4-[3-(2-methoxyethoxy)benzyl]-3-methyl-5-oxo-2,5-dihydro-1H-pyrazol-1-yl}-N-phenylpyridine-3-sulfonamide According to the process described in Example 1.3, starting with 336 mg of methyl 2-[3-(2-methoxyethoxy)benzyl]-3-oxobutanoate and 351 mg of N-ethyl-6-hydrazino-N-phenylpyridine-3-sulfonamide, 441 mg of N-ethyl-6-{4-[3-(2-methoxyethoxy)benzyl]-3-methyl-5-oxo-2,5-dihydro-1H-pyrazol-1-yl}-N-phenylpyridine-3-sulfonamide are obtained in the form of a white powder.

Yield=70% m.p. (° C.)=126

M=C₂₇H₃₀N₄O₅S=522; M+H=523; Method 2: Tr=1.27 min.

¹H NMR, d6-DMSO, 400 MHz, δ (ppm): 12.0 (bs, 1H); 8.6 (bs, 1H); 8.45 (s, 1H); 8.1 (d, 1H); 7.4 (m, 3H); 7.3-7.1 (m, 3H); 6.8 (d, 2H); 7.1 (d, 1H); 4.1 (d, 2H); 3.6 (m, 4H); 3.5 (s, 2H); 3.3 (s, 3H); 2.1 (s, 3H); 1.0 (t, 3H).

EXAMPLE 10

N-ethyl-6-[4-(4-methoxybenzyl)-3-methyl-5-oxo-2,5-dihydro-1H-pyrazol-1-yl]-N-phenylpyridine-3-sulfonamide (Compound 54 of Table I)

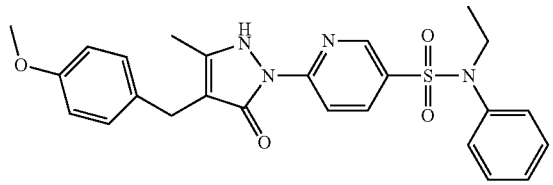 [SMILES: CCN(c1ccccc1)S(=O)(=O)c1ccc(-n2[nH]c(C)c(Cc3ccc(OC)cc3)c2=O)nc1]

10.1. methyl 2-(4-methoxybenzyl)-3-oxobutanoate

A mixture of 1.34 g (8.6 mmol) of 1-(chloromethyl)-4-methoxybenzene, 0.93 mL (8.6 mmol) of methyl acetoacetate, 0.24 g (0.86 mmol) of tetrabutylammonium chloride and 6.9 g of a mixture by mass of K₂CO₃/KOH (4/1) in 5 mL of toluene is heated for 5 minutes at 110° C. in a microwave reactor. The reaction medium is taken up in 80 mL of EtOAc, washed successively with water (2×20 mL), saturated NaHCO₃ solution (20 mL) and brine (20 mL), dried over Na₂SO₄ and then concentrated under reduced pressure. The residue obtained is purified by chromatography on a column of silica gel, eluting with a cyclohexane/EtOAc gradient of 0 to 30% EtOAc.

0.93 g of methyl 2-(4-methoxybenzyl)-3-oxobutanoate is thus obtained in the form of a yellow oil.

Yield=48%

¹H NMR, CDCl₃, 400 MHz, δ (ppm): 7.2 (d, 1H); 7.1 (d, 1H); 6.8 (m, 2H); 3.8 (s, 3H); 3.75 (t, 1H); 3.7 (s, 3H); 3.2 (m, 2H); 2.2 (s, 3H).

10.2. N-ethyl-6-[4-(4-methoxybenzyl)-3-methyl-5-oxo-2,5-dihydro-1H-pyrazol-1-yl]-N-phenylpyridine-3-sulfonamide According to the process described in Example 1.3, starting with 300 mg of methyl 2-(4-methoxybenzyl)-3-oxobutanoate and 371 mg of N-ethyl-6-hydrazino-N-phenylpyridine-3-sulfonamide, 338 mg of N-ethyl-6-[4-(4-methoxybenzyl)-3-methyl-5-oxo-2,5-dihydro-1H-pyrazol-1-yl]-N-phenylpyridine-3-sulfonamide are obtained in the form of a white powder.

Yield=56% m.p. (° C.)=188

M=C₂₅H₂₆N₄O₄S=478; M+H=479; Method 2: Tr=1.29 min.

¹H NMR, d6-DMSO, 400 MHz, δ (ppm): 11.8 (bs, 1H); 8.6 (bs, 1H); 8.45 (s, 1H); 8.1 (d, 1H); 7.4 (m, 3H); 7.3-7.1 (m, 4H); 6.8 (d, 2H); 3.75 (s, 3H); 3.6 (s, 2H); 3.5 (s, 2H); 2.1 (s, 3H); 1.0 (t, 3H).

EXAMPLE 11

6-[4-(2-chloro-6-fluorobenzyl)-3-methyl-5-oxo-2,5-dihydro-1H-pyrazol-1-yl]-N-ethyl-N-phenylpyridine-3-sulfonamide (Compound 20 of Table I)

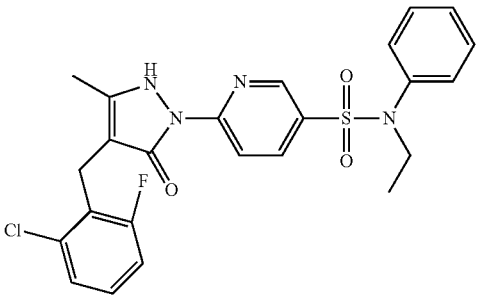 [SMILES: CCN(c1ccccc1)S(=O)(=O)c1ccc(-n2[nH]c(C)c(Cc3c(F)cccc3Cl)c2=O)nc1]

A mixture of 52 mg (0.2 mmol) of methyl 2-(2-chloro-6-fluorobenzyl)-3-oxobutanoate, 73 mg (0.25 mmol) of N-ethyl-6-hydrazino-N-phenylpyridine-3-sulfonamide and 5 mg of pTsOH in 2 mL of toluene is heated for 12 hours at 110° C. and then concentrated under reduced pressure. The residue is taken up in 2 mL of DMF and filtered, and the filtrate is chromatographed on an RP18 reverse-phase column, eluting with an H₂O (containing 2% TFA)/CH₃CN gradient of 0 to 100% CH₃CN.

86 mg of 6-[4-(2-chloro-6-fluorobenzyl)-3-methyl-5-oxo-2,5-dihydro-1H-pyrazol-1-yl]-N-ethyl-N-phenylpyridine-3-sulfonamide are obtained in the form of a white powder;

Yield=99% m.p. (° C.)=206

M=C₂₄H₂₂ClFN₄O₃S=501. M+H=502; Method 1

$^1$H NMR, d6-DMSO, 400 MHz, δ (ppm): 11.9 (bs, 1H); 8.6 (bs, 1H); 8.4 (s, 1H); 8.0 (d, 1H); 7.5-7.3 (m, 5H); 7.2-7.0 (m, 3H); 3.7 (s, 2H); 3.6 (q, 2H); 2.1 (s, 3H); 1.0 (t, 3H).

EXAMPLE 12

N-ethyl-6-[3-methyl-5-oxo-4-(1-phenylcyclopropyl)-2,5-dihydro-1H-pyrazol-1-yl]-N-phenylpyridine-3-sulfonamide (Compound 80 of Table I)

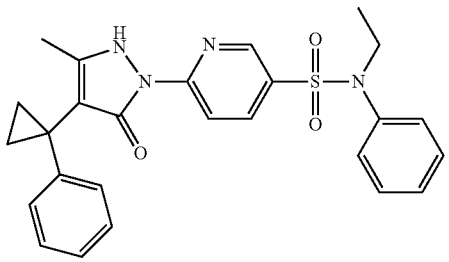 [SMILES: CCN(c1ccccc1)S(=O)(=O)c1ccc(-n2[nH]c(C)c(C3(c4ccccc4)CC3)c2=O)nc1]

12.1. methyl 2-acetyl-3-phenylbut-3-enoate

A suspension of 3.2 g (27.5 mmol) of methyl 3-oxobutanoate, 5.6 g (55.0 mmol) of phenylacetylene and 700 mg (0.8 mmol) of *[ReBr(CO)$_3$(THF)]$_2$ in 55 mL of anhydrous toluene is stirred for 18 hours at 50° C. After cooling to room temperature, the medium is concentrated under reduced pressure. The residue obtained is taken up in 100 mL of DCM, washed successively with water (100 mL) and brine (100 mL), dried over Na$_2$SO$_4$ and then concentrated under reduced pressure and purified by chromatography on a column of silica gel, eluting with a 99/1 DCM/MeOH mixture. 5 g of methyl 2-acetyl-3-phenylbut-3-enoate are obtained in the form of a yellow oil.

Yield=84%
$^1$H NMR, CDCl$_3$, 400 MHz, δ (ppm): 12.6 (s, 1H); 7.3-7.2 (m, 5H); 5.7 (s, 1H); 5.1 (s, 1H); 3.55 (s, 3H); 1.9 (s, 3H).

*[ReBr(CO)$_3$(THF)]$_2$ is freshly prepared from 2 g (4.9 mmol) of ReBr(CO)$_5$ stirred at reflux in 60 mL of anhydrous THF for 16 hours. After concentrating under reduced pressure and recrystallizing from 5 mL of n-hexane/THF (1/1), 700 mg of [ReBr(CO)$_3$(THF)]$_2$ are obtained in the form of a white powder.

Yield=35%.

12.2. methyl 3-oxo-2(1-phenylclopropyl)butanoate

To a solution of 1 g (4.6 mmol) of methyl 2-acetyl-3-phenylbut-3-enoate in 16 mL of DCM are successively added dropwise 20.8 mL (22.9 mmol) of a 1.1M solution of diethylzinc in toluene and 3.7 mL (45.8 mmol) of diiodomethane. The reaction medium is refluxed for 18 hours. After cooling to room temperature, the reaction mixture is treated with 100 mL of water and then extracted with DCM (3×100 mL). The organic phases are combined, washed successively with water (4×100 mL) and brine (100 mL), dried over Na$_2$SO$_4$, filtered and then concentrated under reduced pressure. The residue obtained is purified by chromatography on a column of silica gel, eluting with a 95/5 cyclohexane/EtOAc mixture. 280 mg of methyl 3-oxo-2(1-phenylcyclopropyl)butanoate are obtained in the form of a yellow oil.

Yield=26%.
$^1$H NMR, CDCl$_3$, 400 MHz, δ (ppm): 7.3-6.9 (m, 5H); 3.7 (s, 1H); 3.6 (s, 3H); 2.0 (s, 3H); 1.4 (s, 2H); 1.25 (s, 2H)

12.3. N-ethyl-6-[3-methyl-5-oxo-4-(1-phenylcyclopropyl)-2,5-dihydro-1H-pyrazol-1-yl]-N-phenylpyridine-3-sulfonamide According to the process described in Example 1.3, starting with 280 mg of methyl 3-oxo-2-(1-phenylcyclopropyl) butanoate and 352 mg of N-ethyl-6-hydrazino-N-phenylpyridine-3-sulfonamide, 110 mg of N-ethyl-6-[3-methyl-5-oxo-4-(1-phenylcyclopropyl)-2,5-dihydro-1H-pyrazol-1-yl]-N-phenylpyridine-3-sulfonamide are obtained in the form of a white powder.

m.p. (° C.)=146
M=C$_{26}$H$_{26}$N$_4$O$_3$S=474, M+H=475; Method 2: Tr=1.44 min.
$^1$H NMR, d6-DMSO, 400 MHz, δ (ppm): 12.0 (bs, 1H); 8.6 (bs, 1H); 8.4 (s, 1H); 8.1 (d, 1H); 7.4-7.1 (m, 10H); 3.6 (q, 2H); 2.2 (s, 3H); 1.15 (dd, 4H); 1.0 (t, 3H).

EXAMPLE 14

N-tert-butyl-6-[5-oxo-4-(pyridin-3-ylmethyl)-2,5-dihydro-1H-pyrazol-1-yl]pyridine-3-sulfonamide hydrochloride (Compound 98B of Table I)

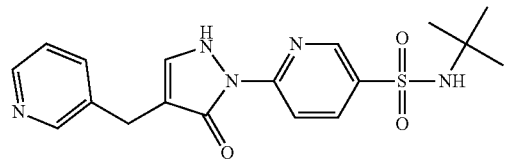 [SMILES: CC(C)(C)NS(=O)(=O)c1ccc(-n2[nH]cc(Cc3cccnc3)c2=O)nc1]

14.1. N-tert-butyl-6-chloropyridine-3-sulfonamide

To a mixture of 17.3 mL (165 mmol) of tert-butylamine and 69 mL (495 mmol) of TEA in 330 mL of DCM are added portionwise, at 0° C., 35 g (165 mmol) of 6-chloropyridine-3-sulfonyl chloride. After stirring for 2 hours at 0° C., the reaction medium is taken up in 600 mL of DCM, washed with water (1 L), saturated NaHCO$_3$ solution (1 L) and brine (1 L), dried over Na$_2$SO$_4$, filtered and concentrated under reduced pressure. 32.4 g of N-tertbutyl-6-chloropyridine-3-sulfonamide are obtained in the form of a white solid.

Yield=79%
$^1$H NMR CDCl$_3$, 400 MHz, δ (ppm): 8.8 (s, 1H); 8.0 (d, 1H); 7.4 (d, 1H); 4.5 (bs, 1H); 1.2 (s, 9H).

14.2. methyl 2-formyl-3-(pyridin-3-yl)propanoate

To a suspension of 2.1 g (90.8 mmol) of sodium in 55 mL of anhydrous Et$_2$O is added dropwise, at 0° C. under argon, a mixture of 15 g (90.8 mmol) of methyl 3-(pyridin-3-yl)propanoate and 7.3 mL (57.41 mmol) of ethyl formate. The medium is then stirred for 12 hours at room temperature, taken up in 200 mL of water and extracted with 100 mL of Et$_2$O. The aqueous phase is acidified to pH 5 and then extracted with 2×300 mL of EtOAc. The organic phase is then dried over Na$_2$SO$_4$, filtered and concentrated under reduced pressure. The residue obtained is purified by chromatography on a column of silica gel, eluting with a DCM/MeOH gradient of 0 to 10% MeOH. 4.8 g of methyl 2-formyl-3-(pyridin-3-yl)propanoate are obtained in the form of a white solid.

Yield=28%

$^1$H NMR, d6-DMSO, 400 MHz, δ (ppm): 11.0 (bs, 1H); 8.45 (s, 1H); 8.4 (d, 1H); 7.7 (d, 1H); 7.5 (d, 1H); 7.2 (dd, 1H); 3.6 (s, 2H); 3.5 (s, 3H)

14.3 N-tert-butyl-6-hydrazinylpyridine-3-sulfonamide

According to the process described in Example 5.2, starting with 32.4 g of N-tert-butyl-6-chloropyridine-3-sulfonamide and 12.9 mL of hydrazine monohydrate, 22.6 g of N-tertbutyl-6-hydrazinylpyridine-3-sulfonamide are obtained in the form of a white solid.

Yield: 71%

$^1$H NMR, d6-DMSO, 400 MHz, δ (ppm): 8.3 (d, 2H); 7.8 (d, 1H); 7.2 (s, 1H); 7.0 (bs, 1H); 4.3 (bs, 2H); 1.2 (s, 9H).

14.4. N-tert-butyl-6-[5-oxo-4-(pyridin-3-ylmethyl)-2,5-dihydro-1H-pyrazol-1-yl]pyridine-3-sulfonamide (Compound 98A of Table I)

According to the process described in Example 1.3, starting with 12 g of N-tert-butyl-6-hydrazinylpyridine-3-sulfonamide and 9.1 g of methyl 2-formyl-3-(pyridin-3-yl)propanoate, 9.92 g of N-tert-butyl-6-[5-oxo-4-(pyridin-3-ylmethyl)-2,5-dihydro-1H-pyrazol-1-yl]pyridine-3-sulfonamide are obtained in the form of a white solid $^1$H NMR, d6-DMSO, 400 MHz, δ (ppm): 8.9 (bs, 1H); 8.5 (bs, 2H); 8.4 (s, 1H); 8.3 (d, 1H); 7.9 (s, 1H); 7.8 (s, 1H); 7.7 (d, 1H); 7.3 (dd, 1H); 3.6 (s, 2H); 1.2 (s, 9H)

Yield=64% m.p. (° C.)=160

M=$C_{18}H_{21}N_5O_3S$=387; M+H=388; Method 2: Tr=0.58 min.

$^1$H NMR, d6-DMSO, 400 MHz, δ (ppm): 8.8 (s, 1H); 8.3 (bs, 3H); 8.4 (s, 1H); 8.3 (d, 1H); 7.9 (s, 1H); 7.7 (d, 1H); 7.4 (t, 1H); 3.6 (s, 2H); 3.4 (bs, 1H); 1.1 (s, 9H)

14.5. N-tert-butyl-6-[5-oxo-4-(pyridin-3-ylmethyl)-2,5-dihydro-1H-pyrazol-1-yl]pyridine-3-sulfonamide hydrochloride To 912 mg of N-tert-butyl-6-[5-oxo-4-(pyridin-3-ylmethyl)-2,5-dihydro-1H-pyrazol-1-yl]pyridine-3-sulfonamide in 20 mL of DCM is added 1 eq. of HCl (4N in dioxane) and the medium is then concentrated under vacuum. 1 g of N-tert-butyl-6-[5-oxo-4-(pyridin-3-ylmethyl)-2,5-dihydro-1H-pyrazol-1-yl]pyridine-3-sulfonamide hydrochloride is obtained in the form of a white powder.

Yield=100% m.p. (° C.)=140° C.

M=$C_{18}H_{21}N_5O_3S$=387; M+H=388; Method 2: Tr=0.58 min.

$^1$H NMR, d6-DMSO, 400 MHz, δ (ppm): 12.0 (bs, 1H); 8.9 (bs, 1H); 8.8 (s, 1H); 8.7 (d, 1H); 8.5 (d, 2H); 8.3 (d, 1H); 8.0 (t, 1H); 7.9 (s, 1H); 7.8 (s, 1H); 3.8 (s, 2H); 1.2 (s, 9H)

EXAMPLE 15

(2-{5-[ethyl(phenyl)sulfamoyl]pyridin-2-yl}-3-oxo-2,3-dihydro-1H-pyrazol-4-yl)acetic acid (Compound 104 of Table I)

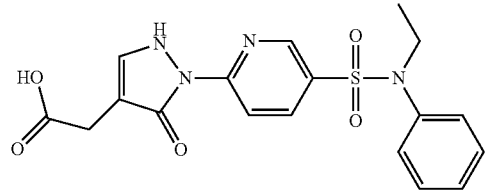 [SMILES: CCN(c1ccccc1)S(=O)(=O)c1ccc(-n2[nH]cc(CC(=O)O)c2=O)nc1]

15.1. ethyl 2-formylbutanedioate

To a suspension of 1.32 g (57.41 mmol) of sodium in 35 mL of anhydrous Et$_2$O is added dropwise, at 0° C., under argon, a mixture of 10 g (57.41 mmol) of ethyl butanedioate and 4.62 mL (57.41 mmol) of ethyl formate. The medium is then stirred for 12 hours at room temperature, taken up in 100 mL of water and extracted with 100 mL of Et$_2$O. The aqueous phase is acidified to pH 5 and then extracted with 100 mL of Et$_2$O. The organic phase is then dried over Na$_2$SO$_4$, filtered and then concentrated under reduced pressure. The residue obtained is purified by chromatography on a column of silica gel, eluting with a 7/3 cyclohexane/EtOAc mixture. 4.3 g of ethyl 2-formylbutanediaote are obtained in the form of a colourless oil.

Yield: 37%

$^1$H NMR, $^1$H NMR, CDCl$_3$, 400 MHz, δ (ppm): 10.0 (s, 1H); 7.1 (d, 1H); 4.4-4.2 (m, 5H); 2.9 (dd, 2H); 1.3 (m, 6H);

15.2 (2-{5-[ethyl(phenyl)sulfamoyl]pyridin-2-yl}-3-oxo-2,3-dihydro-1H-pyrazol-4-yl)acetic acid A mixture of 2.17 g (7.42 mmol) of N-ethyl-6-hydrazino-N-phenylpyridine-3-sulfonamide and 1.5 g (7.42 mmol) of ethyl 2-formylbutanedioate in 15 mL of EtOH is heated for 5 hours at 80° C. The medium is then concentrated under reduced pressure. The precipitate obtained is triturated in Et$_2$O and then filtered and dried with a vane pump. The 4.1 g of beige-coloured powder obtained are added to a solution of 212 mg (9.23 mmol) of sodium dissolved in 17 mL of anhydrous MeOH at room temperature and stirring is continued for 2 hours. The medium is concentrated under reduced pressure and then dissolved in 10 mL of water and 4 mL of 1N sodium hydroxide and stirred for 12 hours at room temperature. The medium is then acidified to pH 5 with 1N HCl and then extracted with DCM (2×100 mL). The combined organic phases are dried over Na$_2$SO$_4$, filtered and then concentrated under reduced pressure. The residue obtained is solidified in pentane, filtered off and dried under vacuum 2.1 g of (2-{5-[ethyl(phenyl)sulfamoyl]pyridin-2-yl}-3-oxo-2,3-dihydro-1H-pyrazol-4-yl)acetic acid are obtained in the form of a white powder.

Yield=58% m.p. (° C.)=174° C.

M=$C_{18}H_{18}N_4O_5S$=402; M+H=403; Method Tr=1.02 min.

$^1$H NMR, d6-DMSO, 400 MHz, δ (ppm): 12.0 (bs, 2H); 8.6 (bs, 1H); 8.5 (bs, 1H); 8.2 (d, 1H); 7.9 (bs, 1H); 7.4 (m, 3H); 7.2 (d, 2H); 3.7 (q, 2H); 3.4 (s, 2H); 1.0 (t, 3H).

EXAMPLE 16 methyl (2-{5-[ethyl(phenyl)sulfamoyl]pyridin-2-yl}-3-oxo-2,3-dihydro-1H-pyrazol-4-yl)acetate (Compound 107 of Table I)

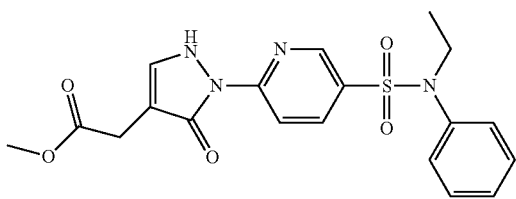 [SMILES: CCN(c1ccccc1)S(=O)(=O)c1ccc(-n2[nH]cc(CC(=O)OC)c2=O)nc1]

16.1 methyl (2-{5-[ethyl(phenyl)sulfamoyl]pyridin-2-yl}-3-oxo-2,3-dihydro-1H-pyrazol-4-yl)acetate A mixture of 0.5 g (1.24 mmol) of (2-{5-[ethyl(phenyl)sulfamoyl]pyridin-2-yl}-3-oxo-2,3-dihydro-1H-pyrazol-4-yl)acetic acid and 0.256 g (1.24 mmol) of DCC is stirred for 3 hours at room temperature. The precipitate formed is filtered off and the filtrate is concentrated under reduced pressure. The residue obtained is purified by chromatography on a column of silica gel, eluting with a 9/1 DCM/MeOH mixture. 0.5 g of methyl 2-[(5-[ethyl(phenyl)sulfamoyl]pyridin-2-yl]-3-oxo-2,3-dihydro-1H-pyrazol-4-yl)acetate is obtained in the form of a brown powder.

Yield=96%
m.p. (° C.)=140° C.
M=$C_{19}H_{20}N_4O_5S$=416; M+H=417; Method 2; Tr=1.44 min
$^1$H NMR, d6-DMSO, 400 MHz, δ (ppm): 12.0 (bs, 1H); 8.6 (s, 1H); 8.4 (s, 1H); 8.2 (d, 1H); 7.9 (s, 1H); 7.4 (m, 3H); 7.2 (d, 2H); 5.6 (d, 0.5H); 3.75 (q, 2H); 3.7 (s, 3H); 3.3 (d, 1.5H); 1.0 (t, 3H)

EXAMPLE 17

2-(2-{5-[ethyl(phenyl)sulfamoyl]pyridin-2-yl}-3-oxo-2,3-dihydro-1H-pyrazol-4-yl)-N-methylacetamide (Compound 108 of Table I)

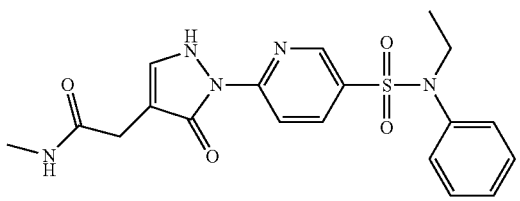 [SMILES: CCN(c1ccccc1)S(=O)(=O)c1ccc(-n2[nH]cc(CC(=O)NC)c2=O)nc1]

To a mixture of 0.28 g (0.7 mmol) of (2-{5-[ethyl(phenyl)sulfamoyl]pyridin-2-yl}-3-oxo-2,3-dihydro-1H-pyrazol-4-yl)acetic acid, 0.61 mL (3.48 mmol) of DIEA and 0.8 mL (1.4 mmol) of methylamine (2N solution in THF) in 2 mL of DCM is added at 0° C. 0.33 g (1.04 mmol) of TBTU. After stirring for 3 hours at room temperature, the medium is taken up in 500 mL of DCM, washed successively with 0.1N HCl (2×40 mL), saturated NaHCO$_3$ solution (2×40 mL) and brine (30 mL), dried over Na$_2$SO$_4$ and then concentrated under reduced pressure and purified by chromatography on a column of silica gel, eluting with a 95/5 DCM/MeOH mixture. 18 mg of 2-(2-{5-[ethyl(phenyl)sulfamoyl]pyridin-2-yl}-3-oxo-2,3-dihydro-1H-pyrazol-4-yl)-N-methylacetamide are obtained in the form of a brown powder.

Yield=6%
m.p. (° C.)=194° C.
M=$C_{19}H_{21}N_5O_5S$=415; M+H=416; Method 2 Tr=0.98
$^1$H NMR, d6-DMSO, 400 MHz, δ (ppm): 12.0 (bs, 1H); 8.6 (bs, 1H); 8.5 (s, 1H); 8.2 (d, 1H); 7.8 (s, 2H); 7.5 (m, 3H); 7.2 (d, 2H); 3.6 (q, 2H); 3.1 (s, 2H); 2.6 (s, 3H); 1.0 (t, 3H)

EXAMPLE 18 ethyl (4-benzyl-1-{5-[ethyl(phenyl)sulfamoyl]pyridin-2-yl}-5-oxo-2,5-dihydro-1H-pyrazol-3-yl)acetate (Compound 106 of Table I)

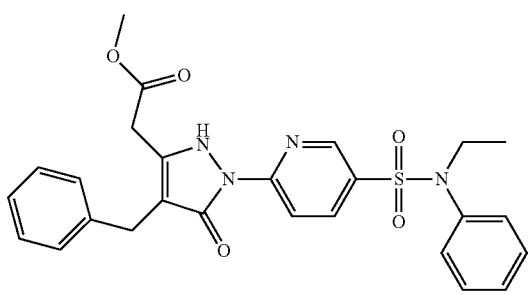 [SMILES: CCN(c1ccccc1)S(=O)(=O)c1ccc(-n2[nH]c(CC(=O)OC)c(Cc3ccccc3)c2=O)nc1]

18.1 ethyl 2-benzyl-3-oxopentanedioate

Under argon, and at room temperature, 1.7 g (74.18 mmol) of sodium are dissolved in 75 mL of anhydrous EtOH. 13.5 mL (74.2 mmol) of diethyl 3-oxopentanedioate and then 8.8 mL (74.2 mmol) of benzyl bromide are then added dropwise, at room temperature. The medium is then refluxed for 3 hours, concentrated under reduced pressure and purified by chromatography on a column of silica gel, eluting with a cyclohexane/EtOAc gradient of 0 to 20% EtOAc. 8.29 g of diethyl 2-benzyl-3-oxopentanedioate are obtained in the form of a translucent oil.

Yield=38%
$^1$H NMR, $^1$H NMR, CDCl$_3$, 400 MHz, δ (ppm): 7.4-7.2 (m, 5H); 4.2 (m, 4H); 4.1 (t, 1H); 3.2 (d, 2H); 1.2 (m, 6H);

18.2. ethyl 4-benzyl-1-{5-[ethyl(phenyl)sulfamoyl]pyridin-2-yl}-5-oxo-2,5-dihydro-1H-pyrazol-3-yl)acetate According to the process described in Example 1.3, starting with 5 g (17.1 mmol) of diethyl 2-benzyl-3-oxopentanedioate and 5 g (17.1 mmol) of N-ethyl-6-hydrazino-N-phenylpyridine-3-sulfonamide, 3 g of ethyl 4-benzyl-1-{5-[ethyl(phenyl)sulfamoyl]pyridin-2-yl}-5-oxo-2,5-dihydro-1H-pyrazol-3-yl)acetate are obtained in the form of a white powder.

Yield=34%
m.p. (° C.)=156
M=$C_{27}H_{28}N_4O_5S$=520; M+H=521 Method 2: Tr=1.52, ¹H NMR, d6-DMSO, 400 MHz, δ (ppm): 12.0 (bs, 1H); 8.5 (bs, 2H); 8.15 (d, 1H); 7.4-7.1 (m, 10H); 4.1 (q, 2H); 3.8-3.6 (m, 6H); 1.2 (t, 3H); 1.0 (t, 3H).

EXAMPLE 19

6-{4-[(5-cyanopyridin-3-yl)methyl]-3-methyl-5-oxo-2,5-dihydro-1H-pyrazol-1-yl}-N-ethyl-N-phenylpyridine-3-sulfonamide (Compound 97 of Table I)

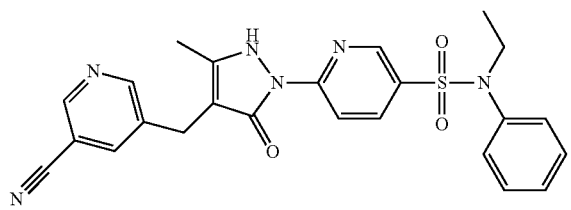 [SMILES: CCN(c1ccccc1)S(=O)(=O)c1ccc(-n2[nH]c(C)c(Cc3cncc(C#N)c3)c2=O)nc1]

19.1 (5-bromopyridin-3-yl)methanol

To a solution of 12 g (59.4 mmol) of 5-bromopyridine-3-carboxylic acid in 300 mL of anhydrous THF, under argon, are added, at −10° C., 6.6 mL of NMM and then 5.7 mL (59.4 mmol) of ethyl chloroformate. After stirring for 20 minutes at −10° C., 6.8 g (179.8 mmol) of sodium borohydride are added portionwise. The medium is then cooled to −70° C. and 400 mL of MeOH are added over 1 hour 30 minutes. The temperature is then allowed to rise to room temperature and stirring is continued for 12 hours. The medium is then concentrated under reduced pressure and then purified by chromatography on a column of silica gel, eluting with a 98/2 DCM/MeOH mixture. 8.4 g of (5-bromopyridin-3-yl)methanol are obtained in the form of a yellow oil.
Yield=75%
¹H NMR, CDCl₃, 400 MHz, δ (ppm): 8.5 (s, 1H); 8.4 (s, 1H); 7.9 (s, 1H); 4.6 (s, 2H); 2.8 (bs, 1H)

19.2 5-(hydroxymethyl)pyridine-3-carbonitrile

A mixture of 4.2 g (22.34 mmol) of (5-bromopyridin-3-yl)methanol and 5 g (55.84 mmol) of copper cyanide in 22 mL of pyridine is heated for 20 hours in a sealed tube at 160° C. After cooling to room temperature, the medium is taken up in 10 mL of concentrated aqueous ammonia and 30 mL of saturated NH₄Cl solution and then stirred for 2 hours. The medium is then extracted with 200 mL of a DCM/iPrOH mixture (85/15), dried over Na₂SO₄ and then concentrated under reduced pressure and purified by chromatography on a column of silica gel, eluting with a 98/2 DCM/MeOH mixture. 2.13 g of 5-(hydroxymethyl)pyridine-3-carbonitrile are obtained in the form of a white solid.
Yield=51%
¹H NMR, CDCl₃, 400 MHz, δ (ppm): 8.9 (d, 2H); 8.0 (s, 1H); 4.9 (s, 2H); 2.3 (bs, 1H)

19.3 5-(chloromethyl)pyridine-3-carbonitrile

To 0.2 g (1.49 mmol) of 5-(hydroxymethyl)pyridine-3-carbonitrile in 2 mL of DCM is added 1 mL (4 mmol) of HCl 4N in dioxane. The mixture is concentrated under reduced pressure and then added to 0.65 mL (8.95 mmol) of thionyl chloride followed by heating for 3 hours at 60° C. After cooling to room temperature, the medium is taken up in 20 mL of toluene, and the precipitate formed is filtered off and then treated with 30 mL of DCM and 30 mL of saturated NaHCO₃ solution. The organic phase is separated out and dried over Na₂SO₄ and then concentrated under reduced pressure. 161 mg of 5-(chloromethyl)pyridine-3-carbonitrile are obtained in the form of an oil.
Yield=73%
¹H NMR, ¹H NMR, CDCl₃, 400 MHz, δ (ppm): 8.9 (d, 2H); 8.0 (s, 1H); 3.5 (s, 2H)

19.4. methyl 2-[(5-cyanopyridin-3-yl)methyl]-3-oxobutanoate

To a suspension of 84 mg (2.11 mmol) of sodium hydride (60% in oil) in 3 mL of anhydrous DME is added, under argon at 0° C., 0.23 ml (2.11 mmol) of methyl acetoacetate. The reaction medium is stirred for 30 minutes at 0° C. and for 30 minutes at room temperature, followed by addition of 161 mg (1.06 mmol) of 5-(chloromethyl)pyridine-3-carbonitrile diluted in 1 mL of DME and 29 mg (0.11 mmol) of tetrabutylammonium iodide. The medium is then heated at 65° C. for 4 hours. After cooling to room temperature, the medium is taken up in 10 mL or water, neutralized by adding 0.1N HCl, and then extracted with EtOAc (2×40 mL), dried over Na₂SO₄, concentrated under reduced pressure and purified by chromatography on a column of silica gel, eluting with a cyclohexane/EtOAc mixture (8/2). 140 mg of methyl 2-[(5-cyanopyridin-3-yl)methyl]-3-oxobutanoate are obtained in the form of a colourless oil.
Yield=57%
¹H NMR, ¹H NMR, CDCl₃, 400 MHz, δ (ppm): 8.8 (s, 1H); 8.6 (s, 1H); 7.8 (s, 1H); 3.7 (t, 1H); 3.65 (s, 3H); 3.2 (dd, 2H); 2.2 (s, 3H)

19.5 6-{4-[(5-cyanopyridin-3-yl)methyl]-3-methyl-5-oxo-2,5-dihydro-1H-pyrazol-1-yl}-N-ethyl-N-phenylpyridine-3-sulfonamide According to the process described in Example 1.3, starting with 125 mg (0.43 mmol) of methyl 2-[(5-cyanopyridin-3-yl)methyl]-3-oxobutanoate and 99 mg (0.43 mmol) of N-ethyl-6-hydrazino-N-phenylpyridine-3-sulfonamide, 103 mg of 6-{4-[(5-cyanopyridin-3-yl)methyl]-3-methyl-5-oxo-2,5-dihydro-1H-pyrazol-1-yl}-N-ethyl-N-phenylpyridine-3-sulfonamide are obtained in the form of a yellow powder.
Yield=51%
m.p. (° C.)=164
M=C₂₄H₂₂N₆O₃S=474; M+H=475; Method 2: Tr=1.24 min.
¹H NMR, d6-DMSO, 400 MHz, δ (ppm): 12.0 (bs, 1H); 8.9 (s, 1H); 8.8 (s, 1H); 8.6 (bs, 1H); 8.4 (s, 1H); 8.2 (s, 1H); 8.15 (d, 1H); 7.4 (m, 3H); 7.1 (d, 2H); 3.7 (s, 4H); 2.2 (s, 3H); 1.0 (t, 3H).

EXAMPLE 20

5-methyl-2-[5-(phenylsulfonyl)pyridin-2-yl]-4-(pyridin-3-ylmethyl)-1,2-dihydro-3H-pyrazol-3-one (Compound 197 of Table II)

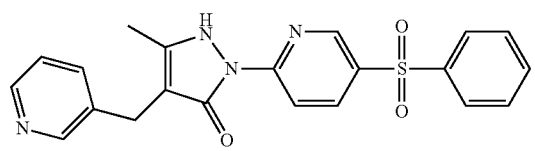 [SMILES: Cc1[nH]n(-c2ccc(S(=O)(=O)c3ccccc3)cn2)c(=O)c1Cc1cccnc1]

20.1 2-chloro-5-(phenylsulfanyl)pyridine

A mixture of 3.4 g (14.3 mmol) of 2-chloro-5 iodopyridine, 1.9 g (17.2 mmol) of thiophenol, 0.93 g (17.2 mmol) of sodium methoxide and 0.36 g (5.7 mmol) of copper in 18 mL of MeOH is heated for 12 hours at 80° C. After cooling to room temperature, the medium is taken up in 100 mL of 1N NaOH and the MeOH is evaporated off under reduced pressure. The reaction medium is extracted with EtOAc (2×100 mL), the organic phase is washed with 0.1N NaOH (2×30 mL), and then dried over $Na_2SO_4$, concentrated under reduced pressure and purified by chromatography on a column of silica gel, eluting with a cyclohexane/EtOAc mixture (8/2). 1.90 g of 2-chloro-5-(phenylsulfanyl)pyridine are obtained in the form of a white powder.

Yield=60%

$^1$H NMR, $CDCl_3$, 400 MHz, δ (ppm): 8.5 (d, 1H); 8.3 (s, 1H); 7.9 (s, 1H); 7.5-7.4 (m, 5H)

20.2 2-chloro-5-(phenylsulfonyl)pyridine

To a solution of 1.9 g (8.57 mmol) of 2-chloro-5-(phenylsulfanyl)pyridine in 40 mL of DCM is added, at room temperature over 15 minutes, a suspension of 4.8 g (21.42 mmol) of 3-chloroperbenzoic acid at 77% in 20 mL of DCM. After stirring for 1 hour, the precipitate formed is filtered off, and the filtrate is taken up in 200 mL of DCM, washed successively with 100 mL of 0.2N sodium hydroxide and then 100 mL of saturated sodium thiosulfate solution, dried over $Na_2SO_4$, concentrated under reduced pressure and purified by chromatography on a column of silica gel, eluting with a cyclohexane/EtOAc mixture (8/2). 0.67 g of 2-chloro-5-(phenylsulfonyl)pyridine is obtained in the form of a white powder.

Yield=31%

$^1$H NMR, $CDCl_3$, 400 MHz, δ (ppm): 8.9 (s, 1H); 8.1-7.9 (m, 3H); 7.6-7.4 (m, 3H); 7.3 (m, 1H)

20.3 2-hydrazinyl-5-(phenylsulfonyl)pyridine

According to the process described in Example 5.2, starting with 0.67 g (2.64 mmol) of 2-chloro-5-(phenylsulfonyl)pyridine, 340 mg of 2-hydrazinyl-5-(phenylsulfonyl)pyridine are obtained in the form of a white powder.

Yield=51%

$^1$H NMR, d6-DMSO, 400 MHz, δ (ppm): 9.0 (s, 1H); 8.6 (d, 1H); 8.5 (s, 1H); 8.4 (m, 2H); 8.0 (d, 1H); 7.8-7.5 (m, 3H); 7.3 (m, 1H); 3.3 (bs, 1H);

20.4 5-methyl-2-[5-(phenylsulfonyl)pyridin-2-yl]-4-(pyridin-3-ylmethyl)-1,2-dihydro-3H-pyrazol-3-one According to the process described in Example 1.3, starting with 340 mg (1.36 mmol) of 2-hydrazinyl-5-(phenylsulfonyl)pyridine and 283 mg (1.36 mmol) of methyl 3-oxo-2-(pyridin-3-ylmethyl)butanoate, 130 mg of 5-methyl-2-[5-(phenylsulfonyl)pyridin-2-yl]-4-(pyridin-3-ylmethyl)-1,2-dihydro-3H-pyrazol-3-one are obtained in the form of a white powder.

Yield=23% m.p. (° C.)=176

M=$C_{21}H_{18}N_4O_3S$=406; M+H=407; Method 2: Tr=0.78 min.

$^1$H NMR, d6-DMSO, 400 MHz, δ (ppm) 12.0 (bs, 1H); 9.0 (s, 1H); 8.6 (d, 1H); 8.5 (s, 1H); 8.4 (m, 2H); 8.0 (d, 2H); 7.8-7.6 (m, 4H); 7.3 (m, 1H); 3.6 (s, 2H); 2.2 (s, 3H)

EXAMPLE 21

N-ethyl-6-{4-[(5-methoxypyridin-3-yl)methyl]-5-oxo-2,5-dihydro-1H-pyrazol-1-yl}-N-phenylpyridine-3-sulfonamide hydrochloride (Compound 101 of Table I)

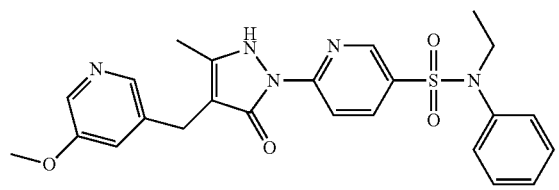 [SMILES: CCN(c1ccccc1)S(=O)(=O)c1ccc(-n2[nH]c(C)c(Cc3cncc(OC)c3)c2=O)nc1]

21.1. methyl (2E)-3-(5-methoxypyridin-3-yl)prop-2-enoate

To a suspension of 3.12 g (78.1 mmol) of sodium hydride (60% in oil) in 30 mL of anhydrous THF is added, over 45 minutes, under argon and at 0° C., 16.4 g (78.1 mmol) of methyl (diethoxyphosphoryl)acetate in 10 mL of THF. Stirring is maintained for 30 minutes at 0° C. and 5.1 g (37.2 mmol) of 5-methoxypyridine-3-carbaldehyde in 20 mL of anhydrous THF are then added dropwise at 0° C. After cooling to room temperature, the reaction mixture is treated with 150 mL of water and then extracted with EtOAc (3×100 mL). The organic phases are combined, washed successively with water (2×20 mL), dried over $Na_2SO_4$, filtered and then concentrated under reduced pressure. The residue obtained is purified by chromatography on a column of silica gel, eluting with a cyclohexane/EtOAC gradient of 0 to 40% EtOAc. 1 g of methyl (2E)-3-(5-methoxypyridin-3-yl)prop-2-enoate is obtained in the form of a white powder.

Yield=14%.

$^1$H NMR, $CDCl_3$, 400 MHz, δ (ppm): 8.4 (d, 1H); 7.7 (d, 1H); 7.4 (s, 1H); 6.5 (d, 1H); 3.9 (s, 3H); 3.8 (s, 3H)

21.2. methyl 3-(5-methoxypyridin-3-yl)propanoate

In Parr apparatus, a mixture of 1 g (5.33 mmol) of methyl (2E)-3-(5-methoxypyridin-3-yl)prop-2-enoate in 20 mL of MeOH and 0.1 g of 10% Pd/C is hydrogenated at 7 bar for 5 hours. The reaction mixture is then filtered through Whatman GF/F paper and concentrated under reduced pressure. 1 g of methyl 3-(5-methoxypyridin-3-yl)propanoate is thus obtained in the form of a wax, which is used without further purification in the following step.

Yield=100%

$^1$H NMR, $CDCl_3$, 400 MHz, δ (ppm): 8.3 (s, 1H); 8.2 (s, 1H); 7.1 (s, 1H); 3.85 (s, 3H); 3.6 (s, 3H); 3.0 (t, 2H); 2.7 (t, 3H).

21.3. methyl 2-formyl-3-(5-methoxypyridin-3-yl)-propanoate

According to the process described in Example 14.2, starting with 1.04 g (5.33 mmol) of methyl 3-(5-methoxypyridin-3-yl)propanoate, 600 mg of methyl 2-formyl-3-(5-methoxypyridin-3-yl)propanoate are obtained in the form of a wax, which is used without further purification in the following step.
Yield=51%

21.4. N-ethyl-6-{4-[(5-methoxypyridin-3-yl)methyl]-5-oxo-2,5-dihydro-1H-pyrazol-1-yl}-N-phenylpyridine-3-sulfonamide hydrochloride According to the process described in Example 2.3, starting with 250 mg (1.12 mmol) of methyl 2-formyl-3-(5-methoxypyridin-3-yl)propanoate and 327 mg (1.12 mmol) of N-ethyl-6-hydrazino-N-phenylpyridine-3-sulfonamide, 131 mg of N-ethyl-6-{4-[(5-methoxypyridin-3-yl)methyl]-5-oxo-2,5-dihydro-1H-pyrazol-1-yl}-N-phenylpyridine-3-sulfonamide hydrochloride are obtained in the form of a lyophilizate.
Yield=25%
m.p. (° C.)=136
M=$C_{23}H_{23}N_5O_4S$=465; M+H=466; Method 2: Tr=0.97 min.
$^1$H NMR, d6-DMSO, 400 MHz, δ (ppm): 11.0 (bs, 1H); 8.6 (s, 2H); 8.4 (d, 2H); 8.2 (d, 1H); 8.1 (s, 1H); 7.9 (s, 1H); 7.4 (m, 3H); 7.1 (d, 2H); 4.0 (s, 3H); 3.8 (s, 2H); 3.6 (q, 2H); 1.0 (t, 3H)

EXAMPLE 22 methyl {2-[5-(tert-butylsulfamoyl)pyridin-2-yl]-3-oxo-2,3-dihydro-1H-pyrazol-4-yl}(phenyl)acetate (Compound 113 of Table I)

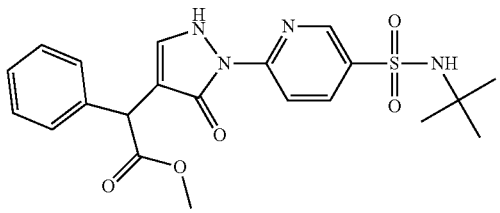 [SMILES: COC(=O)C(c1ccccc1)c1c[nH]n(-c2ccc(S(=O)(=O)NC(C)(C)C)cn2)c1=O]

22.1. ethyl 3-cyano-3-phenylpropanoate

A mixture of 64 g (257.8 mmol) of diethyl benzylidenepropanedioate and 17 g (261 mmol) of potassium cyanide in 750 mL of EtOH and 75 mL of water is heated for 18 hours at 60° C. The medium is then concentrated under reduced pressure and taken up in 500 mL of brine and then extracted with $Et_2O$ (2×500 mL). The organic phases are dried over $Na_2SO_4$, filtered and then concentrated under reduced pressure. 43.5 g of ethyl 3-cyano-3-phenylpropanoate are obtained in the form of a solid, which is used without further purification in the following step.
Yield=83%

22.2. 2-phenylbutanedioic acid

A mixture of 43.5 g (214 mmol) of ethyl 3-cyano-3-phenylpropanoate and 52.2 g (930.4 mmol) of potassium hydroxide in 670 mL of EtOH is refluxed for 4 hours. After cooling to room temperature, the medium is concentrated under vacuum and then treated with 1 L of 1N HCl, and a precipitate then forms, which is filtered off and rinsed with water (2×50 mL). The solid obtained is taken up in a mixture of 200 mL of toluene and 40 mL of EtOH and concentrated under reduced pressure, and then dried with a vane pump. 37 g of 2-phenylbutanedioic acid are obtained in the form of a solid, which is used without further purification in the following step.
Yield=89%

22.3. diethyl 2-phenylbutanedioate

In Dean-Stark apparatus, a mixture of 37 g (190.5 mmol) of 2-phenylbutanedioic acid, 6 mL of conc. $H_2SO_4$, 80 mL of toluene and 80 mL of EtOH is refluxed for 72 hours. After cooling to room temperature, the reaction mixture is concentrated under reduced pressure and then treated with 300 mL of water, and extracted with $Et_2O$ (2×400 mL). The organic phases are combined, dried over $Na_2SO_4$, filtered and then concentrated under reduced pressure. The residue obtained is purified by chromatography on a column of silica gel, eluting with a cyclohexane/EtOAc gradient of 0 to 10% EtOAc. 22 g of diethyl 2-phenylbutanedioate are obtained in the form of an oil.
Yield=46%.
$^1$H NMR, $CDCl_3$, 400 MHz, δ (ppm): 7.5 (m, 5H); 4.2 (m, 5H); 3.0 (dd, 2H); 1.0 (t, 6H)

22.4. diethyl 2-formyl-3-phenylbutanedioate

According to the process described in Example 14.2, starting with 7.0 g (28 mmol) of diethyl 2-phenylbutanedioate, 7.0 g of diethyl 2-formyl-3-phenylbutanedioate are obtained in the form of an oil.
Yield=89%

22.5. ethyl {2-[5-(tert-butylsulfamoyl)pyridin-2-yl]-3-oxo-2,3-dihydro-1H-pyrazol-4-yl}-(phenyl)acetate According to the process described in Example 27.2, starting with 2 g (7.19 mmol) of diethyl 2-formyl-3-phenylbutanedioate and 1.75 g (7.19 mmol) of N-tert-butyl-6-hydrazinylpyridine-3-sulfonamide, 3.1 g of methyl {2-[5-(tert-butylsulfamoyl)pyridin-2-yl]-3-oxo-2,3-dihydro-1H-pyrazol-4-yl}(phenyl)acetate are obtained in the form of a powder.
Yield=93%
$^1$H NMR, d6-DMSO, 400 MHz, δ (ppm): 8.6 (s, 1H); 8.6 (d, 1H); 8.0 (d, 1H); 7.7 (s, 2H); 7.3 (m, 5H); 4.6 (s, 1H); 4.1 (q, 2H); 1.0 (m, 12H);

22.6 1-[5-(tert-butylsulfamoyl)pyridin-2-yl]-4-[carboxy(phenyl)methyl]-1H-pyrazol-5-olate A mixture of 2.8 g (5.8 mmol) of ethyl 2-[5-(tert-butylsulfamoyl)pyridin-2-yl]-3-oxo-2,3-dihydro-1H-pyrazol-4-yl}(phenyl)acetate and 5.8 mL (5.8 mmol) of 1N NaOH, in 12 mL of EtOH is stirred for hours at room temperature. 5.8 mL of 1N HCl are added, and the medium is extracted with DCM (2×100 mL). The organic phases are dried over $Na_2SO_4$, filtered and then concentrated under reduced pressure. 2 g of 1-[(5-(tert-butylsulfamoyl)pyridin-2-yl]-4-[carboxy(phenyl)methyl]-1H-pyrazol-5-olate are obtained in the form of a beige-coloured powder, which is used without further purification in the following step.

22.7. methyl {2-[5-(tert-butylsulfamoyl)pyridin-2-yl]-3-oxo-2,3-dihydro-1H-pyrazol-4-yl}(phenyl)acetate To a mixture of 0.3 g (0.66 mmol) of 1-[5-(tert-butylsulfamoyl)pyridin-2-yl]-4-[carboxy(phenyl)methyl]-1H-pyrazol- 5-olate in 3 mL of anhydrous MeOH is added, at 0° C., 0.11 mL (0.73 mmol) of thionyl chloride. After cooling to room temperature, stirring is continued for 12 hours. The medium is taken up in 40 mL of DCM, washed with 20 mL of saturated NaHCO$_3$ solution, dried over Na$_2$SO$_4$ and then concentrated under reduced pressure. The residue obtained is solidified in a DCM/pentane mixture and then filtered off and dried under vacuum. 0.67 g of methyl 2-[5-(tert-butylsulfamoyl)pyridin-2-yl]-3-oxo-2,3-dihydro-1H-pyrazol-4-yl}(phenyl)acetate is obtained in the form of a beige-coloured powder.
Yield=73%
m.p. (° C.)=66
M=C$_{21}$H$_{24}$N$_4$O$_5$S=444; M+H=445; Method 2: Tr=1.21 min.
$^1$H NMR, d6-DMSO, 400 MHz, δ (ppm): 12.3 (bs, 1H); 8.8 (s, 1H); 8.6 (bs, 1H); 8.3 (d, 1H); 7.7 (d, 2H); 7.4 (m, 5H); 4.9 (s, 1H); 3.7 (s, 3H); 1.0 (t, 9H)

EXAMPLE 23 methyl N-cyclopentyl-N-({6-[5-oxo-4-(pyridin-3-ylmethyl)-2,5-dihydro-1H-pyrazol-1-yl]pyridin-3-yl}sulfonyl)glycinate hydrochloride (Compound 128 of Table I)

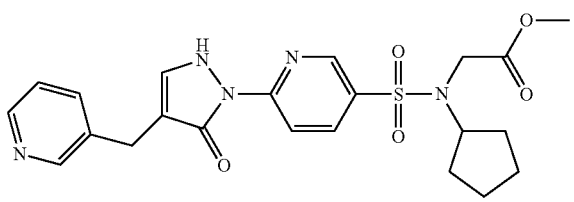 [SMILES: COC(=O)CN(C1CCCC1)S(=O)(=O)c1ccc(-n2[nH]cc(Cc3cccnc3)c2=O)nc1]

23.1. 6-chloro-N-cyclopentylpyridine-3-sulfonamide

According to the process described in Example 14.1, starting with 5 g (23.6 mmol) of 6-chloropyridine-3-sulfonyl chloride and 2 g (23.6 mmol) of cyclopentylamine, 5.1 g of 6-chloro-N-cyclopentylpyridine-3-sulfonamide are obtained in the form of a brown solid.
Yield=84%
$^1$H NMR, CDCl$_3$, 400 MHz, δ (ppm): 8.8 (s, 1H); 8.0 (d, 1H); 7.4 (d, 1H); 4.5 (d, 1H); 3.6 (m, 1H); 1.8 (m, 2H); 1.6 (m, 4H); 1.3 (m, 2H)

23.2. methyl N-[(6-chloropyridin-3-yl)sulfonyl]-N-cyclopentylglycinate

A mixture of 2 g (7.67 mmol) of 6-chloro-N-cyclopentylpyridine-3-sulfonamide, 0.7 mL (7.67 mmol) of methyl bromoacetate and 1.2 g (8.4 mmol) of K$_2$CO$_3$ in 15 mL of CH$_3$CN is heated for 12 hours at 80° C. After cooling to room temperature, the medium is filtered and the filtrate is concentrated. The residue is taken up in 100 mL of DCM, washed successively with 50 mL of saturated NaHCO$_3$ solution and 50 mL of water, and the organic phase is then dried over Na$_2$SO$_4$, concentrated under reduced pressure and purified by chromatography on a column of silica gel, eluting with an 8/2 heptane/EtOAc mixture. 2.4 g of methyl N-[(6-chloropyridin-3-yl)sulfonyl]-N-cyclopentylglycinate are obtained in the form of an oil.
Yield=93%
$^1$H NMR, CDCl$_3$, 400 MHz, δ (ppm) 9.0 (s, 1H); 8.3 (d, 1H); 7.4 (d, 1H); 4.1 (s, 2H); 4.05 (m, 1H); 3.8 (s, 3H); 1.9 (m, 2H); 1.6 (m, 4H); 1.3 (m, 2H)

23.3. methyl N-cyclopentyl-N-[(6-hydrazinylpyridin-3-yl)sulfonyl]glycinate

According to the process described in Example 5.2, starting with 2.4 g (7.2 mmol) of methyl N-[(6-chloropyridin-3-yl)sulfonyl]-N-cyclopentylglycinate, 2 g of methyl N-cyclopentyl-N-[(6-hydrazinylpyridin-3-yl)sulfonyl]glycinate are obtained in the form of a yellow solid.
Yield=85%
$^1$H NMR, CDCl$_3$, 400 MHz, δ (ppm) 8.6 (s, 1H); 8.0 (d, 1H); 6.8 (d, 1H); 6.6 (bs, 1H); 4.05 (m, 1H); 4.0 (s, 2H); 3.6 (s, 3H); 1.8 (m, 2H); 1.6 (m, 4H); 1.2 (m, 2H)

23.4. methyl N-cyclopentyl-N-({6-[5-oxo-4-(pyridin-3-ylmethyl)-2,5-dihydro-1H-pyrazol-1-yl]pyridin-3-yl}sulfonyl)glycinate hydrochloride According to the process described in Example 2.3, starting with 200 mg (0.61 mmol) of methyl N-cyclopentyl-N-[(6-hydrazinylpyridin-3-yl)sulfonyl]glycinate and 117 mg (0.61 mmol) of methyl 3-oxo-2-(pyridin-3-ylmethyl)butanoate, 130 mg of methyl N-cyclopentyl-N-({6-[5-oxo-4-(pyridin-3-ylmethyl)-2,5-dihydro-1H-pyrazol-1-yl]pyridin-3-yl}sulfonyl)glycinate hydrochloride are obtained in the form of a white lyophilizate.
Yield=34%
m.p. (° C.)=100
M=C$_{22}$H$_{25}$N$_5$O$_5$S=471; M+H=472; Method 2: Tr=0.87 min.
$^1$H NMR, d6-DMSO, 400 MHz, δ (ppm) 8.7 (d, 2H); 8.6 (d, 1H); 8.4 (d, 2H); 8.3 (d, 1H); 7.8 (m, 1H); 7.7 (s, 1H); 5.0-4.0 (bs, 2H); 3.9 (m, 1H); 3.8 (s, 2H); 3.6 (s, 2H); 3.4 (s, 3H); 1.4-1.0 (m, 8H).

EXAMPLE 24

2,2-dimethylpropyl 6-[5-oxo-4-(pyridin-3-ylmethyl)-2,5-dihydro-1H-pyrazol-1-yl]pyridine-3-carboxylate (Compound 198 of Table II)

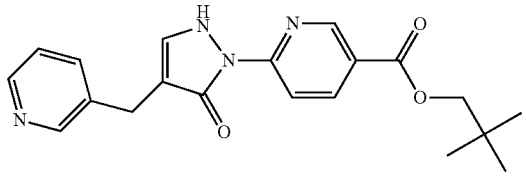 [SMILES: CC(C)(C)COC(=O)c1ccc(-n2[nH]cc(Cc3cccnc3)c2=O)nc1]

24.1. 2,2-dimethylpropyl 6-chloropyridine-3-carboxylate

To a solution of 10 g (56.8 mmol) of 6-chloropyridine-3-carbonyl chloride in 100 mL of anhydrous toluene are added under argon, at room temperature, 15 g (170.4 mmol) of 2,2-dimethylpropanol. The reaction medium is then heated for 6 hours at 80° C. After cooling to room temperature, the medium is concentrated and the residue obtained is taken up in 800 mL of EtOAc, washed successively with water (2×200 mL), saturated NaHCO$_3$ solution (2×200 mL) and brine (100 mL), dried over Na$_2$SO$_4$, and then concentrated under reduced pressure and purified by chromatography on a column of silica gel, eluting with a cyclohexane/EtOAc gradient of 0 to 5% EtOAc. 11.9 g of 2,2-dimethylpropyl 6-chloropyridine-3-carboxylate are obtained in the form of a white powder.
Yield=92%.
$^1$H NMR, CDCl$_3$, 400 MHz, δ (ppm): 7.5 (m, 5H); 4.2 (m, 5H); 3.0 (dd, 2H); 1.0 (t, 6H)

24.2. 2,2-dimethylpropyl 6-hydrazinylpyridine-3-carboxylate

According to the process described in Example 5.2, starting with 11.9 g (52.26 mmol) of 2,2-dimethylpropyl 6-chloropyridine-3-carboxylate, 4.3 g of 2,2-dimethylpropyl 6-hydrazinylpyridine-3-carboxylate are obtained in the form of a white powder.

Yield=37%

$^1$H NMR, d6-DMSO, 400 MHz, δ (ppm): 8.7 (s, 1H); 8.15 (d, 1H); 6.9 (d, 1H); 4.0 (s, 2H); 3.5 (bs, 1H); 1.0 (s, 9H).

24.3. 2,2-dimethylpropyl 6-[5-oxo-4-(pyridin-3-yl)methyl)-2,5-dihydro-1H-pyrazol-1-yl]pyridine-3-carboxylate According to the process described in Example 1.3, starting with 0.3 g (1.34 mmol) of 2,2-dimethylpropyl 6-hydrazinylpyridine-3-carboxylate and 0.26 g (1.34 mmol) of methyl 3-oxo-2-(pyridin-3-ylmethyl)butanoate, 185 mg of 2,2-dimethylpropyl 6-[5-oxo-4-(pyridin-3-ylmethyl)-2,5-dihydro-1H-pyrazol-1-yl]pyridine-3-carboxylate are obtained in the form of a white solid.

Yield=38% m.p. (° C.)=160

M=$C_{20}H_{22}N_4O_3$=366; M+H=367; Method 2: Tr=1.01 min.

$^1$H NMR, d6-DMSO, 400 MHz, δ (ppm): 12.0 (bs, 1H); 8.9 (s, 1H); 8.8 (s, 1H); 8.7 (d, 1H); 8.5 (d, 1H); 8.4 (d, 1H); 8.3 (d, 1H); 8.0 (t, 1H) 7.9 (s, 1H); 3.9 (s, 2H); 3.8 (s, 2H); 1.0 (s, 9H);

EXAMPLE 25 methyl 3-(2-{5-[cyclopentyl(methyl)sulfamoyl]pyridin-2-yl}-3-oxo-2,3-dihydro-1H-pyrazol-4-yl)-3-phenylpropanoate (Compound 121 of Table I)

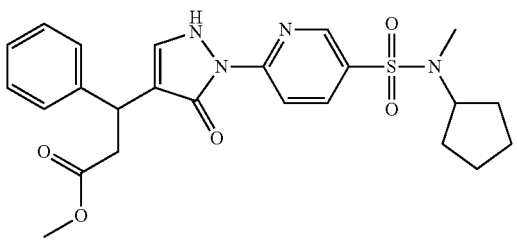 [SMILES: COC(=O)CC(c1ccccc1)c1c[nH]n(-c2ccc(S(=O)(=O)N(C)C3CCCC3)cn2)c1=O]

25.1. diethyl 3-phenylpentanedioate

A mixture of 6 g (28.8 mmol) of 3-phenylpentanedioic acid and 7.9 mL (109.5 mol) of thionyl chloride is heated at 80° C. for 1 hour. The medium is then concentrated and the solid obtained is added portionwise to 8 mL of EtOH at 0° C. The medium is then heated at 80° C. for 30 minutes. After cooling to room temperature, the medium is concentrated and the residue obtained is taken up in 400 mL of DCM, washed successively with saturated NaHCO$_3$ solution (2×100 mL) and brine (100 mL), dried over Na$_2$SO$_4$ and then concentrated under reduced pressure. 6.97 g of diethyl 3-phenylpentanedioate are obtained in the form of a powder, which is used without further purification in the following step.

Yield=91.5%.

25.2. diethyl 2-formyl-3-phenylpentanedioate

According to the process described in Example 14.2, starting with 3 g (11.35 mmol) of diethyl 3-phenylpentanedioate, 0.23 g of diethyl 2-formyl-3-phenylpentanedioate is obtained in the form of a yellow oil.

Yield=7%

$^1$H NMR, d6-DMSO, 400 MHz, δ (ppm) 10.9 (s, 1H); 7.7 (d, 1H); 7.3-7.1 (m, 5H); 4.5 (t, 1H); 4.0 (q, 4H); 3.0 (m, 2H); 1.0 (m, 6H)

25.3. 3-(2-{5-[cyclopentyl(methyl)sulfamoyl]pyridin-2-yl}-3-oxo-2,3-dihydro-1H-pyrazol-4-yl)-3-phenylpropanoate According to processes 22.5 and 22.6, starting with 0.23 g (0.79 mmol) of diethyl 2-formyl-3-phenylpentanedioate and 0.21 g (0.79 mmol) of N-cyclopentyl-6-hydrazinyl-N-methylpyridine-3-sulfonamide, 0.38 g of 3-(1-{5-[cyclopentyl(methyl)sulfamoyl]pyridin-2-yl}-5-oxido-1H-pyrazol-4-yl)-3-phenylpropanoate is obtained in the form of a powder.

Yield=89%

25.4. methyl 3-(2-{5-[cyclopentyl(methyl)sulfamoyl]pyridin-2-yl}-3-oxo-2,3-dihydro-1H-pyrazol-4-yl)-3-phenylpropanoate According to the process described in Example 22.7, starting with 0.38 g (0.78 mmol) of 3-(2-{5-[cyclopentyl(methyl)sulfamoyl]pyridin-2-yl}-3-oxo-2,3-dihydro-1H-pyrazol-4-yl)-3-phenylpropanoate, 0.34 g of methyl 3-(1-{5-[cyclopentyl(methyl)sulfamoyl]pyridin-2-yl}-5-oxido-1H-pyrazol-4-yl)-3-phenylpropanoate is obtained.

m.p. (° C.)=80

M=$C_{24}H_{28}N_4O_5S$=484; M+H=485; Method 3: Tr=4.4 min.

$^1$H NMR, d6-DMSO, 400 MHz, δ (ppm): 8.9 (s, 1H); 8.7 (bs, 1H); 8.5 (d, 1H); 7.9 (s, 1H); 7.4 (d, 1H); 7.3 (t, 3H); 7.2 (t, 2H); 4.4 (t, 1H); 4.3 (t, 1H); 3.6 (s, 3H); 3.2 (dd, 1H); 3.1 (dd, 1H); 2.7 (s, 3H); 1.8-1.4 (m, 8H)

EXAMPLE 26

6-(4-benzyl-5-oxo-2,5-dihydro-1H-pyrazol-1-yl)-N-cyclopentyl-N-[3-(dimethylamino)propyl]pyridine-3-sulfonamide hydrochloride (Compound 123 of Table I)

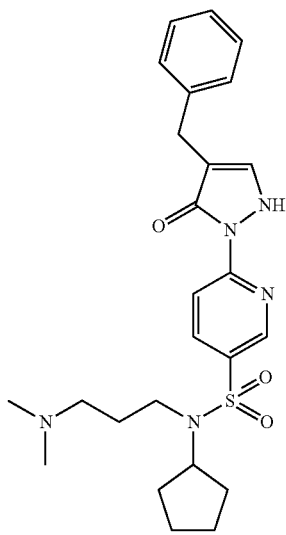 [SMILES: CN(C)CCCN(C1CCCC1)S(=O)(=O)c1ccc(-n2[nH]cc(Cc3ccccc3)c2=O)nc1]

26.1. N-[3-(benzyloxy)propyl]-6-chloro-N-cyclopentylpyridine-3-sulfonamide

A mixture of 1 g (3.84 mmol) of 6-chloro-N-cyclopentylpyridine-3-sulfonamide, 1.32 g (9.59 mmol) of K$_2$CO$_3$ and 0.88 mL (4.99 mmol) of [(3-bromopropoxy)methyl]benzene in 8 mL of anhydrous DMF is heated for 12 hours at 40° C. After cooling to room temperature, the medium is taken up in 300 mL of EtOAc, washed successively with water (2×100 mL), saturated NaHCO$_3$ solution (100 mL) and brine (100 mL), dried over Na$_2$SO$_4$ and then concentrated under reduced pressure and purified by chromatography on a column of silica gel, eluting with a cyclohexane/EtOAc gradient of 0 to 10% EtOAc. 1.65 g of N-[3-(benzyloxy)propyl]-6-chloro-N-cyclopentylpyridine-3-sulfonamide are thus obtained in the form of an oil.

Yield=99%.

$^1$H NMR, CDCl$_3$, 400 MHz, δ (ppm): 8.85 (s, 1H); 8.1 (d, 1H); 7.5 (d, 1H); 7.4-7.3 (m, 5H); 4.5 (s, 2H); 4.2 (m, 1H); 3.6 (t, 2H); 3.2 (dd, 2H); 2.1 (m, 2H); 1.6-1.3 (m, 8H)

26.2. N-[3-(benzyloxy)propyl]-N-cyclopentyl-6-hydrazinylpyridine-3-sulfonamide According to the process described in Example 5.2, starting with 1.55 g (3.79 mmol) of N-[3-(benzyloxy)propyl]-6-chloro-N-cyclopentylpyridine-3-sulfonamide, 1.5 g of N-[3-(benzyloxy)propyl]-N-cyclopentyl-6-hydrazinylpyridine-3-sulfonamide are obtained in the form of a yellow solid.

Yield=90%

$^1$H NMR, CDCl$_3$, 400 MHz, δ (ppm): 8.6 (s, 1H); 8.4 (bs, 1H); 7.95 (d, 1H); 7.85 (d, 1H); 7.5-7.3 (m, 5H); 6.9 (d, 1H); 6.6 (bs, 1H); 4.5 (s, 2H); 4.2 (m, 1H); 3.6 (t, 2H); 3.2 (dd, 2H); 2.1 (m, 2H); 1.6-1.3 (m, 8H)

26.3. 6-(4-benzyl-5-oxo-2,5-dihydro-1H-pyrazol-1-yl)-N-[3-(benzyloxy)propyl]-N-cyclopentylpyridine-3-sulfonamide According to the process described in Example 1.3, starting with 0.19 g of methyl 2-benzyl-3-oxopropanoate and 0.4 g of N-[3-(benzyloxy)propyl]-N-cyclopentyl-6-hydrazinylpyridine-3-sulfonamide, 0.29 g of 6-(4-benzyl-5-oxo-2,5-dihydro-1H-pyrazol-1-yl)-N-[3-(benzyloxy)propyl]-N-cyclopentylpyridine-3-sulfonamide is obtained in the form of a beige-coloured solid.

Yield=55%

$^1$H NMR, d6-DMSO, 400 MHz, δ (ppm): 12.0 (bs, 1H); 8.8 (s, 1H); 8.6 (bs, 1H); 8.4 (d, 1H); 7.7 (s, 1H); 7.4-7.1 (m, 10H); 4.5 (s, 2H); 4.2 (m, 1H); 3.6 (s, 2H); 3.5 (t, 2H); 3.2 (t, 2H); 2.0 (m, 2H); 1.6-1.2 (6H).

26.4. 6-(4-benzyl-5-oxo-2,5-dihydro-1H-pyrazol-1-yl)-N-cyclopentyl-N-(3-hydroxypropyl)pyridine-3-sulfonamide To a solution of 150 mg (0.27 mmol) of 6-(4-benzyl-5-oxo-2,5-dihydro-1H-pyrazol-1-yl)-N-[3-(benzyloxy)propyl]-N-cyclopentylpyridine-3-sulfonamide in 2 mL of DCM is added dropwise, at −78° C. under argon, 0.82 mL (0.82 mmol) of boron tribromide (1M in DCM). Stirring is continued for 1 hour at −78° C., and 2 mL of MeOH are then added at 0° C. The medium is taken up in 40 mL of DCM, washed successively with saturated NaHCO$_3$ solution (30 mL) and brine (30 mL), dried over Na$_2$SO$_4$ and then concentrated under reduced pressure and purified by chromatography on a column of silica gel, eluting with a 9/1 DCM/MeOH mixture. 106 mg of 6-(4-benzyl-5-oxo-2,5-dihydro-1H-pyrazol-1-yl)-N-cyclopentyl-N-(3-hydroxypropyl)pyridine-3-sulfonamide are thus obtained in the form of a powder.

Yield=85%

$^1$H NMR, d6-DMSO, 400 MHz, δ (ppm): 8.8 (s, 1H); 8.6 (bs, 1H); 8.4 (d, 1H); 7.7 (s, 1H); 7.4 (m, 5H); 7.3 (m, 1H); 4.5 (t, 1H); 4.2 (m, 1H); 3.6 (s, 2H); 3.5 (q, 2H); 3.2 (t, 2H); 1.8 (m, 2H); 1.5-1.2 (6H).

26.5. 6-(4-benzyl-5-oxo-2,5-dihydro-1H-pyrazol-1-yl)-N-cyclopentyl-N-[3-(dimethylamino)propyl] pyridine-3-sulfonamide hydrochloride To a solution of 82 mg (0.18 mmol) of 6-(4-benzyl-5-oxo-2,5-dihydro-1H-pyrazol-1-yl)-N-cyclopentyl-N-(3-hydroxypropyl)pyridine-3-sulfonamide and 50 μL (0.36 mmol) of Et$_3$N in 0.5 mL of anhydrous DCM are added, under argon at 0° C., 27 μL (0.36 mmol) of mesyl chloride; the temperature is allowed to return gradually to room temperature, and stirring is continued for 1 hour. The medium is taken up in 20 mL of DCM, washed successively with water (2×10 mL) and brine (20 mL), dried over Na$_2$SO$_4$ and then concentrated under reduced pressure. In a sealed tube, the residue obtained (110 mg of yellow oil) is taken up in 2 mL of DCM and then treated for 1 minute with a stream of dimethylamine which is bubbled through the solution. The medium is then, followed by heating for 11 hours at 60° C. After cooling to room temperature, the medium is concentrated and the residue obtained is triturated in an Et$_2$O/CH$_3$CN mixture. The precipitate formed filtered off, rinsed with pentane, dried under reduced pressure and then freeze-dried after addition of 1 eq. of 1N HCl. 57 mg of 6-(4-benzyl-5-oxo-2,5-dihydro-1H-pyrazol-1-yl)-N-cyclopentyl-N-[3-(dimethylamino)propyl] pyridine-3-sulfonamide hydrochloride are thus obtained in the form of a lyophilizate.

Yield=88% m.p. (° C.)=230

M=C$_{25}$H$_{33}$N$_5$O$_3$S=483; M+H=484; Method 2: Tr=1.1 min $^1$H NMR, d6-DMSO, 400 MHz, δ (ppm): 12.0 (bs, 1H); 10.8 (bs, 1H); 8.9 (s, 1H); 8.8 (s, 1H); 8.5 (d, 1H); 7.8 (s, 1H); 7.4 (m, 5H); 7.3 (m, 1H); 4.5 (m, 1H); 4.2 (m, 1H); 3.6 (s, 2H); 3.3 (t, 2H); 3.2 (q, 2H); 2.7 t (s, 6H); 2.0 (m, 2H); 1.6-1.3 (6H).

EXAMPLE 27

6-(4-benzyl-5-oxo-2,5-dihydro-1H-pyrazol-1-yl)-N-ethyl-N-phenylpyridine-3-sulfonamide (Compound 93 of Table I)

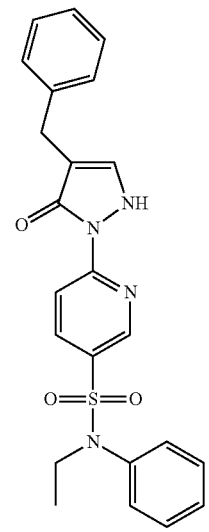 [SMILES: CCN(c1ccccc1)S(=O)(=O)c1ccc(-n2[nH]cc(Cc3ccccc3)c2=O)nc1]

27.1. methyl 2-benzyl-3-oxopropanoate

To a mixture of 3 g (18.3 mmol) of methyl 3-phenylpropanoate and 3.57 mL (54.8 mmol) of methyl formate in 36 mL of toluene, under argon, are added dropwise successively 54.8 mL (54.8 mmol) of a 1 M solution of $TiCl_4$ in toluene, 0.17 mL (0.91 mmol) of trimethylsilyl trifluoromethanesulfonate and 19.6 mL (82.2 mmol) of tributylamine. The medium is then heated for 2 hours 30 minutes at 60° C. and stirred for 12 hours at room temperature.

The reaction medium is hydrolysed with 200 mL of water and extracted with 200 mL of $Et_2O$. The organic phase is dried over $Na_2SO_4$, filtered and concentrated under reduced pressure. 3.12 g of methyl 2-benzyl-3-oxopropanoate are obtained in the form of an oil, which is used without further purification in the following step.

Yield=87%

27.2. 6-(4-benzyl-5-oxo-2,5-dihydro-1H-pyrazol-1-yl)-N-ethyl-N-phenylpyridine-3-sulfonamide A mixture of 0.38 g (1.3 mmol) of N-ethyl-6-hydrazino-N-phenylpyridine-3-sulfonamide and 0.25 g (1.3 mmol) of methyl 2-benzyl-3-oxopropanoate in 2 mL of an AcOH/MeOH mixture (1/1) is heated for 4 hours at 80° C. The medium is then concentrated under reduced pressure, and the residue obtained is solidified in an $Et_2O$/pentane mixture (1/1), and then filtered off and dried under reduced pressure. At room temperature, the 440 mg of solid obtained are then added portionwise to a solution of 22 mg (0.96 mmol) of sodium in 1 mL of MeOH, and stirring is then continued for 3 hours at room temperature. The reaction mixture is then concentrated under reduced pressure, taken up in 10 mL of water and then acidified to pH 3-4 by adding AcOH. The precipitate obtained is then filtered off, washed with pentane and then recrystallized from EtOH and dried. 245 mg of 6-(4-benzyl-5-oxo-2,5-dihydro-1H-pyrazol-1-yl)-N-ethyl-N-phenylpyridine-3-sulfonamide are thus obtained in the form of a white powder.

Yield=59%
m.p. (° C.)=180
$M=C_{23}H_{22}N_4O_3S=434$; M+H=435; Method 2: Tr=1.35 min.

$^1$H NMR, d6-DMSO, 400 MHz, δ (ppm): 12 (bs, 1H); 8.6 (bs, 1H); 8.5 (s, 1H); 8.1 (d, 1H) 7.7 (s, 1H); 7.5-7.1 (m, 10H); 3.7 (q, 2H); 3.6 (s, 2H); 1.0 (t, 3H).

EXAMPLE 28

6-(4-benzyl-5-oxo-3-trifluoromethyl-2,5-dihydro-1H-pyrazol-1-yl)-N-ethyl-N-phenylpyridine-3-sulfonamide (Compound 83 of Table I)

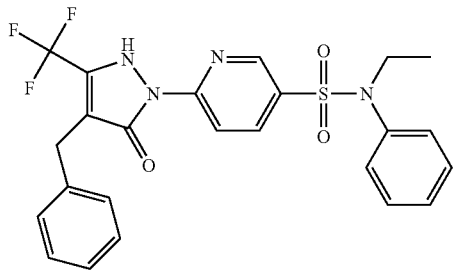 [SMILES: CCN(c1ccccc1)S(=O)(=O)c1ccc(-n2[nH]c(C(F)(F)F)c(Cc3ccccc3)c2=O)nc1]

28.1. methyl 2-benzyl-4,4,4-trifluoro-3,3-dihydroxybutanoate

To a solution of 675 mg (29.4 mmol) of sodium in 15 mL of anhydrous MeOH, under argon, are added dropwise 3.73 mL (29.4 mmol) of methyl 3,3,3-trifluoropropanoate. After stirring for 30 minutes at room temperature, 3.5 mL of benzyl bromide are added and the medium is heated for 12 hours at 70° C. The reaction mixture is then concentrated under reduced pressure. The residue obtained is taken up in 100 mL of EtOAc, washed with 50 mL of brine, dried over $Na_2SO_4$, filtered and concentrated under reduced pressure. After purification by chromatography on a column of silica gel, eluting with a cyclohexane/EtOAc mixture (85/15), 3.4 g of methyl 2-benzyl-4,4,4-trifluoro-3,3-dihydroxybutanoate are obtained in the form of an oil, which is used without further purification in the following step.

Yield=37%.

28.2. 6-(4-benzyl-5-oxo-3-trifluoromethyl-2,5-dihydro-1H-pyrazol-1-yl)-N-ethyl-N-phenylpyridine-3-sulfonamide A mixture of 1 g (3.59 mmol) of methyl 2-benzyl-4,4,4-trifluoro-3,3-dihydroxybutanoate, 1.05 g (3.59 mmol) of N-ethyl-6-hydrazino-N-phenylpyridine-3-sulfonamide and 1 g of 4 Å molecular sieves in 8 mL of MeOH is heated for 12 hours at 90° C. At room temperature, the reaction medium is taken up in 30 mL of toluene, and refluxed for 12 hours in Dean-Stark apparatus. The reaction medium is then filtered and concentrated under reduced pressure, and the residue obtained is then taken up in 50 mL of DCM, washed with 1N HCl solution (2×50 mL), dried over $Na_2SO_4$, filtered and concentrated under reduced pressure. The solid thus obtained is recrystallized from EtOH. 224 mg of 6-(4-benzyl-5-oxo-3-trifluoromethyl-2,5-dihydro-1H-pyrazol-1-yl)-N-ethyl-N-phenylpyridine-3-sulfonamide are obtained in the form of white crystals.

Yield=12%
m.p. (° C.)=186
$M=C_{24}H_{21}F_3N_4O_3S=502$; M+H=503; Method 3: Tr=4.4 min.

$^1$H NMR, d6-DMSO, 400 MHz, δ (ppm): 12 (bs, 1H); 8.7 (s, 1H); 8.25 (d, 1H); 8.0 (d, 1H); 7.5-7.1 (m, 10H); 3.9 (s, 2H); 3.7 (q, 2H); 1.0 (t, 3H).

EXAMPLE 29

6-(4-benzyl-5-oxo-2,5-dihydro-1H-pyrazol-1-yl)-N-[(1R,3S)-3-(hydroxymethyl)cyclopentyl]-N-methylpyridine-3-sulfonamide (Compound 138 of Table I)

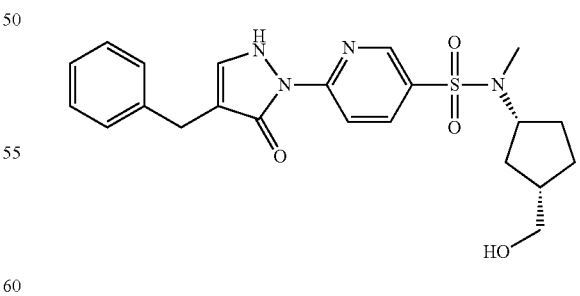

29.1. tert-butyl [(1R,3S)-3-(hydroxymethyl)cyclopentyl]carbamate

To a solution of 2 g (8.7 mmol) of (1S,3R)-3-[(tert-butoxycarbonyl)amino]cyclopentanecarboxylic acid and 1.33 mL (9.6 mmol) of $Et_3N$ in 20 mL of anhydrous THF are added dropwise, at −20° C., 1.2 mL (9.2 mmol) of isobutyl chloroformate. The medium is stirred for 45 minutes at −20° C. and the insoluble material formed is then filtered off. A solution of 1 g (26.2 mmol) of sodium borohydride in a THF/$H_2O$ mixture (16 mL/4 mL) is added dropwise to the filtrate at −10° C. and stirring is then continued, while allowing the temperature to return to room temperature. 100 mL of 0.1N HCl are then added slowly and the reaction medium is then extracted with 2×200 mL of EtOAc, dried over $Na_2SO_4$, filtered and concentrated under reduced pressure. After purification by chromatography on a column of silica gel, eluting with a DCM/MeOH mixture (95/5), 1.4 g of tert-butyl [(1R,3S)-3-(hydroxymethyl)cyclopentyl]carbamate are obtained in the form of an oil.

Yield=77%.

$^1$H NMR, $CDCl_3$, 400 MHz, δ (ppm): 4.5 (bs, 1H); 3.9 (m, 1H); 3.5 (d, 2H); 2.1 (m, 2H); 1.8-1.7 (m, 3H); 1.5 (s, 2H); 1.4 (s, 9H); 1.0 (m, 1H)

29.2. tert-butyl {(1R,3S)-3-[(benzyloxy)methyl]cyclopentyl}carbamate

To a solution of 1.4 g (6.7 mmol) of tert-butyl [(1R,3S)-3-(hydroxymethyl)cyclopentyl]carbamate in 20 mL of anhydrous THF are added portionwise under argon, at room temperature, 0.27 g (6.7 mmol) of sodium hydride at 60% in oil. After stirring for 45 minutes, the medium is cooled to 0° C. and 0.8 mL (6.7 mmol) of benzyl bromide is added. After stirring for 1 hour at room temperature, the medium is hydrolysed with 30 mL of water and extracted with 2×100 mL of EtOAc, dried over $Na_2SO_4$, concentrated under reduced pressure and then purified by chromatography on a column of silica gel, eluting with a 99/1 DCM/MeOH mixture. 1.53 g of tert-butyl {(1R,3S)-3-[(benzyloxy)methyl]cyclopentyl}carbamate are obtained in the form of an oil.

Yield=75%

29.3. (1R,3S)-3-[(benzyloxy)methyl]cyclopentanamine hydrochloride

To a solution of 1.52 g (5 mmol) of tert-butyl {(1R,3S)-3-[(benzyloxy)methyl]-cyclopentyl}carbamate in 20 mL of DCM are added, at 0° C., 5 mL (20 mmol) of a 4N solution of HCl in dioxane. The medium is then stirred for 12 hours at room temperature, and then concentrated under reduced pressure. The residue obtained is solidified in 20 mL of $Et_2O$, filtered and dried under vacuum. 1 g of (1R,3S)-3-[(benzyloxy)methyl]cyclopentanamine hydrochloride is obtained in the form of a powder.

Yield=83%

29.4. N-{(1R,3S)-3-[(benzyloxy)methyl]cyclopentyl}-6-chloropyridine-3-sulfonamide According to the process of 14.1, starting with 1 g of (1R,3S)-3-[(benzyloxy)methyl]-cyclopentanamine hydrochloride and 1 g of 6-chloropyridine-3-sulfonyl chloride, 1.2 g of N-{(1R,3S)-3-[(benzyloxy)methyl]cyclopentyl}-6-chloropyridine-3-sulfonamide are obtained in the form of a pink powder.

Yield=83%

$^1$H NMR, $CDCl_3$, 400 MHz, δ (ppm): 8.6 (s, 1H); 7.8 (dd, 1H); 7.4-7.3 (m, 5H); 7.2 (s, 1H); 5.8 (d, 1H); 4.5 (dd, 2H); 3.7 (m, 1H); 3.3 (m, 2H); 2.2 (m, 1H); 1.9 (m, 1H); 1.6-1.5 (m, 4H); 1.2 (dd, 1H)

29.5. N-{(1R,3S)-3-[(benzyloxy)methyl]cyclopentyl}-6-chloro-N-methylpyridine-3-sulfonamide According to process 23.2, starting with 0.66 g of 4 N-{(1R,3S)-3-[(benzyloxy)methyl]cyclopentyl}-6-chloropyridine-3-sulfonamide and 0.22 mL of methyl iodide, 0.58 g of N-{(1R,3S)-3-[(benzyloxy)methyl]cyclopentyl}-6-chloro-N-methylpyridine-3-sulfonamide is obtained in the form of an oil.

Yield=86%

29.6. N-{(1R,3S)-3-[(benzyloxy)methyl]cyclopentyl}-6-hydrazinyl-N-methylpyridine-3-sulfonamide According to process 5.2, starting with 0.58 g of N-{(1R,3S)-3-[(benzyloxy)methyl]-cyclopentyl}-6-chloro-N-methylpyridine-3-sulfonamide and 0.15 mL of hydrazine hydrate, 0.49 g of N-{(1R,3S)-3-[(benzyloxy)methyl]cyclopentyl}-6-hydrazinyl-N-methylpyridine-3-sulfonamide is obtained.

Yield=86%

29.7. 6-(4-benzyl-5-oxo-2,5-dihydro-1H-pyrazol-1-yl)-N-{(1R,3S)-3-[(benzyloxy)methyl]cyclopentyl}pyridine-3-sulfonamide According to the process described in Example 1.3, starting with 0.495 g of N-{(1R,3S)-3-[(benzyloxy)methyl]cyclopentyl}-6-hydrazinyl-N-methylpyridine-3-sulfonamide and 0.244 g of methyl 2-benzyl-3-oxopropanoate, 301 mg of 6-(4-benzyl-5-oxo-2,5-dihydro-1H-pyrazol-1-yl)-N-{(1R,3S)-3-[(benzyloxy)methyl]cyclopentyl}pyridine-3-sulfonamide are obtained in the form of a powder.

Yield=44%

29.8. 6-(4-benzyl-5-oxo-2,5-dihydro-1H-pyrazol-1-yl)-N-[(1R,3S)-3-(hydroxymethyl)cyclopentyl]-N-methylpyridine-3-sulfonamide To a solution of 0.3 g (0.57 mmol) of 6-(4-benzyl-5-oxo-2,5-dihydro-1H-pyrazol-1-yl)-N-{(1R,3S)-3-[(benzyloxy)methyl]cyclopentyl}pyridine-3-sulfonamide in 2 mL of DCM cooled to −78° C. are added 1.7 mL of boron tribromide. The temperature is then allowed to rise to 0° C. and stirring is continued for 1 hour at 0° C. 10 mL of MeOH are then added at −10° C. and the medium is concentrated under reduced pressure. The medium is taken up in 100 mL of DCM, washed successively with saturated $NaHCO_3$ solution (2×20 mL) and brine (20 mL), dried over $Na_2SO_4$, concentrated under reduced pressure and then purified by chromatography on a column of silica gel, eluting with a 90/10 DCM/MeOH mixture. 126 mg of 6-(4-benzyl-5-oxo-2,5-dihydro-1H-pyrazol-1-yl)-N-[(1R,3S)-3-(hydroxymethyl)cyclopentyl]-N-methylpyridine-3-sulfonamide are obtained in the form of a powder.

Yield=50%

$\alpha^{20}_D$: −12° (c=0.1; MeOH)

m.p. (° C.)=108

M=$C_{22}H_{26}N_4O_4S$=442; M+H=443; Method 2: Tr=1.09 min.

$^1$H NMR, d6-DMSO, 400 MHz, δ (ppm): 8.8 (s, 1H); 8.7 (bs, 1H); 8.4 (d, 1H); 7.8 (bs, 1H); 7.4-7.3 (m, 5H); 7.1 (m, 1H); 4.5 (bs, 1H); 4.4 (m, 1H); 3.6 (bs, 2H); 3.4 (m, 2H); 2.8 (s, 3H); 1.9 (m, 1H); 1.6-1.1 (m, 6H)

EXAMPLE 30

6-(4-benzyl-5-oxo-2,5-dihydro-1H-pyrazol-1-yl)-N-cyclopentyl-N-[3-hydroxy-2-(hydroxymethyl)propyl]pyridine-3-sulfonamide (Compound 147 of Table I)

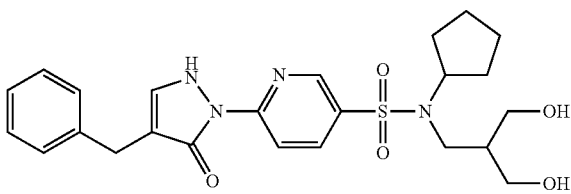 [SMILES: O=c1c(Cc2ccccc2)c[nH]n1-c1ccc(S(=O)(=O)N(CC(CO)CO)C2CCCC2)cn1]

30.1. (2,2-dimethyl-1,3-dioxan-5-yl)methyl 4-methylbenzenesulfonate

To a solution of 1.5 g (10.26 mmol) of (2,2-dimethyl-1,3-dioxan-5-yl)methanol and 1.71 mL of $Et_3N$ in 15 mL of DCM, cooled to 0° C., are added 2.15 g (11.3 mmol) of tosyl chloride. The medium is allowed to warm to room temperature, and stirring is continued for 1 hour. The medium is taken up in 100 mL of DCM, washed successively with 0.1N HCl (2×20 mL) and brine (20 mL), dried over $Na_2SO_4$, concentrated under reduced pressure and then purified by chromatography on a column of silica gel, eluting with a 99/1 DCM/MeOH mixture. 3 g of (2,2-dimethyl-1,3-dioxan-5-yl)methyl 4-methylbenzenesulfonate are obtained in the form of a colourless oil.

Yield=97%

$^1$H NMR, $CDCl_3$, 400 MHz, δ (ppm): 7.8 (d, 2H); 7.3 (d, 2H); 4.1 (d, 2H); 3.9 (dd, 2H); 3.6 (dd, 2H); 2.4 (s, 3H); 1.9 (m, 1H); 1.4 (s, 3H); 1.2 (s, 3H)

30.2. N-[(2,2-dimethyl-1,3-dioxan-5-yl)methyl]cyclopentanamine

A mixture of 1.5 g (5 mmol) of (2,2-dimethyl-1,3-dioxan-5-yl)methyl 4-methylbenzenesulfonate and 10 mL (101 mmol) of cyclopentylamine is heated for 12 hours at 80° C. The medium is concentrated under reduced pressure and then taken up in 200 mL of $Et_2O$, washed with water (2×50 mL) and then dried over $Na_2SO_4$ and concentrated under reduced pressure. 1 g of N-[(2,2-dimethyl-1,3-dioxan-5-yl)methyl]cyclopentanamine is obtained in the form of an oil, which is used without further purification in the following step.

Yield=100%

30.3 N-cyclopentyl-N-[(2,2-dimethyl-1,3-dioxan-5-yl)methyl]-6-hydrazinylpyridine-3-sulfonamide The compound is prepared according to processes 14.1 and 14.3, starting with N-[(2,2-dimethyl-1,3-dioxan-5-yl)methyl]cyclopentanamine, 6-chloropyridine-3-sulfonyl chloride and hydrazine hydrate.

Yield: 70%

$^1$H NMR, d6-DMSO, 400 MHz, δ (ppm): 8.5 (s, 1H); 8.25 (s, 1H); 8.0 (s, 1H); 7.8 (d, 1H); 7.7 (s, 1H); 7.2 (d, 1H); 6.8 (d, 1H); 4.4 (s, 1H); 4.2 (m, 1H); 3.9 (dd, 2H); 3.6 (dd, 2H); 3.0 (dd, 2H); 2.0 (m, 1H); 1.9 (d, 2H); 1.6-1.4 (m, 4H); 1.3 (s, 3H); 1.2 (s, 3H)

30.4. 6-(4-benzyl-5-oxo-2,5-dihydro-1H-pyrazol-1-yl)-N-cyclopentyl-N-[3-hydroxy-2-(hydroxymethyl)propyl]pyridine-3-sulfonamide According to the process described in Example 11, starting with 0.485 g of N-cyclopentyl-N-[(2,2-dimethyl-1,3-dioxan-5-yl)methyl]-6-hydrazinylpyridine-3-sulfonamide and 0.242 g of methyl 2-benzyl-3-oxopropanoate, 79 mg of 6-(4-benzyl-5-oxo-2,5-dihydro-1H-pyrazol-1-yl)-N-cyclopentyl-N-[3-hydroxy-2-(hydroxymethyl)propyl]pyridine-3-sulfonamide are obtained in the form of a powder.

Yield=14% m.p. (° C.)>260

$M=C_{24}H_{30}N_4O_5S=486$; M+H=487; Method 2: Tr=2.09 min.

$^1$H NMR, d6-DMSO, 400 MHz, δ (ppm): 12 (bs, 1H); 8.8 (s, 1H); 8.6 (t, 2H); 8.25 (d, 1H); 7.7 (s, 1H); 7.4-7.2 (m, 5H); 4.3 (q, 2H); 3.9 (m, 2H); 3.0 (m, 1H); 2.8 (m, 1H); 2.7 (s, 3H); 1.6-1.3 (m, 8H)

EXAMPLE 31

6-(4-benzyl-5-oxo-2,5-dihydro-1H-pyrazol-1-yl)-N-cyclopentyl-N-[(2R)-2,3-dihydroxypropyl]pyridine-3-sulfonamide (Compound 142 of Table I)

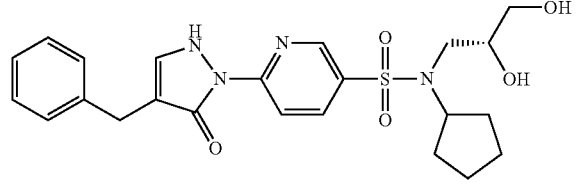

According to the processes described in Example 30, the compound is obtained from [(4R)-2,2-dimethyl-1,3-dioxolan-4-yl]methanol, cyclopentylamine, 6-chloropyridine-3-sulfonyl chloride and methyl 2-benzyl-3-oxopropanoate.

m.p. (° C.)=184

$α^{20}_D$: −24° (c=0.1; DMSO)

$M=C_{23}H_{28}N_4O_5S=472$; M+H=473; Method 2: Tr=1.39 min.

$^1$H NMR, d6-DMSO, 400 MHz, δ (ppm): 12 (bs, 1H); 8.8 (s, 1H); 8.6 (bs, 1H); 8.4 (d, 1H); 7.8 (s, 1H); 7.3-7.1 (m, 5H); 4.8 (s, 1H); 4.6 (s, 1H); 4.2 (m, 1H); 3.8 (s, 1H); 3.6 (s, 2H); 3.3 (m, 2H); 2.9 (m, 1H); 1.6-1.3 (m, 9H)

EXAMPLE 32

6-(4-benzyl-5-oxo-2,5-dihydro-1H-pyrazol-1-yl)-N-cyclopentyl-N-[(2S)-2,3-dihydroxypropyl]pyridine-3-sulfonamide (Compound 148 of Table I)

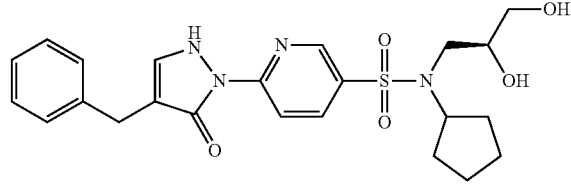

According to the processes described in Example 30, the compound is obtained from [(4S)-2,2-dimethyl-1,3-dioxolan-4-yl]methanol, cyclopentylamine, 6-chloropyridine-3-sulfonyl chloride and methyl 2-benzyl-3-oxopropanoate.

m.p. (° C.)=184

α²⁰_D=: −+33° (c=0.15; DMSO)

M=C₂₃H₂₈N₄O₅S=472; M+H=473; Method 2: Tr=1.39 min.

¹H NMR, d6-DMSO, 400 MHz, δ (ppm): 12 (bs, 1H); 8.8 (s, 1H); 8.6 (bs, 1H); 8.4 (d, 1H); 7.8 (s, 1H); 7.3-7.1 (m, 5H); 4.8 (s, 1H); 4.6 (s, 1H); 4.2 (m, 1H); 3.8 (s, 1H); 3.6 (s, 2H); 3.3 (m, 2H); 2.9 (m, 1H); 1.6-1.3 (m, 9H)

EXAMPLE 33

6-(4-benzyl-5-oxo-2,5-dihydro-1H-pyrazol-1-yl)-N-(2,3-dihydroxypropyl)-N-phenylpyridine-3-sulfonamide (Compound 143 of Table I)

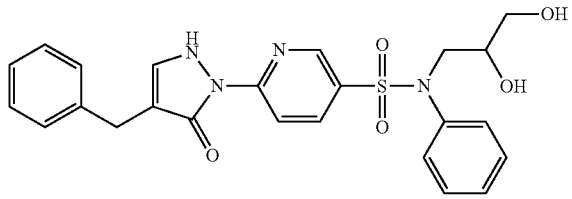 [SMILES: O=c1c(Cc2ccccc2)c[nH]n1-c1ccc(S(=O)(=O)N(CC(O)CO)c2ccccc2)cn1]

32.1. 6-chloro-N-phenylpyridine-3-sulfonamide

According to process 14.1, starting with 1 g of 6-chloropyridine-3-sulfonyl chloride and 0.86 mL of aniline, 1.15 g of 6-chloro-N-phenylpyridine-3-sulfonamide are obtained in the form of a yellow solid.

Yield=91%

¹H NMR, d6-DMSO, 400 MHz, δ (ppm): 10.5 (bs, 1H); 8.7 (s, 1H); 8.1 (dd, 1H); 7.75 (dd, 1H); 7.3 (m, 2H); 7.2 (m, 3H)

32.2. 6-chloro-N-phenyl-N-(prop-2-en-1-yl)pyridine-3-sulfonamide

According to process 23.2, starting with 1.15 g of 6-chloro-N-phenylpyridine-3-sulfonamide and 0.37 mL of allyl bromide, 1.29 g of 6-chloro-N-phenyl-N-(prop-2-en-1-yl)pyridine-3-sulfonamide are obtained in the form of a yellow solid.

Yield=97%

¹H NMR, d6-DMSO, 400 MHz, δ (ppm): 8.6 (s, 1H); 8.0 (dd, 1H); 7.9 (dd, 1H); 7.4 (m, 3H); 7.2 (m, 2H); 5.7 (m, 1H); 5.2 (dd, 1H); 5.1 (dd, 1H); 4.3 (d, 2H)

32.3. 6-chloro-N-(2,3-dihydroxypropyl)-N-phenylpyridine-3-sulfonamide

To a solution of 1.3 g (4.2 mmol) of 6-chloro-N-phenyl-N-(prop-2-en-1-yl)pyridine-3-sulfonamide in 17 mL of a mixture (1/1) of tBuOH and water are added, at room temperature, 1.37 g (11.7 mmol) of NMO and 0.52 mL (0.04 mmol) of 2.5% OsO₄ in tBuOH. Stirring is continued for 12 hours. The medium is then diluted with 200 mL of water and extracted with Et₂O (2×100 mL), dried over Na₂SO₄, filtered and concentrated under reduced pressure. 1.14 g of 6-chloro-N-(2,3-dihydroxypropyl)-N-phenylpyridine-3-sulfonamide are obtained in the form of an oil, which is used without further purification in the following step.

Yield=80%.

¹H NMR, CDCl₃, 400 MHz, δ (ppm): 8.5 (s, 1H); 7.8 (d, 1H); 7.4-7.3 (m, 4H); 7.1 (d, 2H); 3.7-3.5 (m, 3H); 2.5 (bs, 1H); 2.0 (bs, 1H); (m, 2H)

32.4. 6-chloro-N-[(2,2-dimethyl-1,3-dioxolan-4-yl) methyl]-N-phenylpyridine-3-sulfonamide A mixture of 0.67 g (1.96 mmol) of 6-chloro-N-(2,3-dihydroxypropyl)-N-phenylpyridine-3-sulfonamide, 0.53 mL (4.3 mmol) of 2,2-dimethoxypropane and 37 mg of pTsOH in 4 mL of DMF is stirred for 3 hours at room temperature. The medium is taken up in 100 mL of EtOAc, washed with 50 mL of saturated NaHCO₃ solution and 50 mL of water and then dried over Na₂SO₄, filtered and concentrated under reduced pressure. 0.54 g 6-chloro-N-[(2,2-dimethyl-1,3-dioxolan-4-yl)methyl]-N-phenylpyridine-3-sulfonamide is obtained in the form of a brown solid, which is used without further purification in the following step.

Yield=73%.

¹H NMR, CDCl₃, 400 MHz, δ (ppm): 8.5 (s, 1H); 7.7 (d, 1H); 7.4 (d, 1H); 7.3 (m, 3H); 7.0 (d, 2H); 4.1 (m, 1H); 3.9 (m, 1H), 3.8 (dd, 2H); 3.5 (m, 1H); 1.3 (s, 3H); 1.2 (s, 3H)

32.5. N-[(2,2-dimethyl-1,3-dioxolan-4-yl)methyl]-6-hydrazinyl-N-phenylpyridine-3-sulfonamide According to process 5.2, starting with 0.54 g of 6-chloro-N-[(2,2-dimethyl-1,3-dioxolan-4-yl)methyl]-N-phenylpyridine-3-sulfonamide and 30 μL of hydrazine hydrate, 0.53 g of N-[(2,2-dimethyl-1,3-dioxolan-4-yl)methyl]-6-hydrazinyl-N-phenylpyridine-3-sulfonamide is obtained in the form of a white solid.

Yield=99%

¹H NMR, d6-DMSO, 400 MHz, δ (ppm): 8.6 (s, 1H); 8.1 (s, 1H); 7.5 (d, 1H); 7.4 (m, 3H); 7.2 (d, 2H); 6.8 (bs, 1H); 1.3 (s, 3H); 1.2 (s, 3H)

32.6 6-(4-benzyl-5-oxo-2,5-dihydro-1H-pyrazol-1-yl)-N-(2,3-dihydroxypropyl)-N-phenylpyridine-3-sulfonamide According to process 1.3, starting with 0.2 g (0.53 mmol) of N-[(2,2-dimethyl-1,3-dioxolan-4-yl)methyl]-6-hydrazinyl-N-phenylpyridine-3-sulfonamide and 0.1 g of methyl 2-benzyl-3-oxopropanoate, 127 mg of 6-(4-benzyl-5-oxo-2,5-dihydro-1H-pyrazol-1-yl)-N-(2,3-dihydroxypropyl)-N-phenylpyridine-3-sulfonamide are obtained in the form of a white solid.

Yield=50% m.p. (° C.)=174

M=C₂₄H₂₄N₄O₅S=480; M+H=481; Method 2: Tr=1.39 min.

¹H NMR, d6-DMSO, 400 MHz, δ (ppm): 12 (bs, 1H); 8.5 (bs, 1H); 8.4 (s, 1H); 8.1 (d, 2H); 7.8 (s, 1H); 7.4-7.2 (m, 7H); 7.2-7.1 (m, 3H); 4.7 (d, 1H); 4.5 (t, 1H); 3.6 (dd, 2H); 3.4 (m, 4H)

EXAMPLE 33

3-(2-{5-[cyclopentyl(methyl)sulfamoyl]pyridin-2-yl}-3-oxo-2,3-dihydro-1H-pyrazol-4-yl)-3-phenyl-N-(2,2,2-trifluoroethyl)propanamide (Compound 146 of Table I)

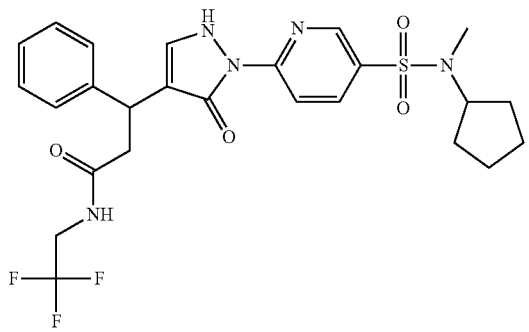 [SMILES: CN(C1CCCC1)S(=O)(=O)c1ccc(-n2[nH]cc(C(CC(=O)NCC(F)(F)F)c3ccccc3)c2=O)nc1]

33.1 3-(2-{5-[cyclopentyl(methyl)sulfamoyl]pyridin-2-yl}-3-oxo-2,3-dihydro-1H-pyrazol-4-yl)-3-phenyl-N-(2,2,2-trifluoroethyl)propanamide To a solution of 200 mg (0.43 mmol) of 3-(2-{5-[cyclopentyl(methyl)sulfamoyl]pyridin-2-yl}-3-oxo-2,3-dihydro-1H-pyrazol-4-yl)-3-phenylpropanoate, 0.3 mL (1.7 mmol) of DIEA and 30 µL (0.43 mmol) of 2,2,2-trifluoroethylamine in 1 mL of DCM are added, at 0° C., 207 mg (0.64 mmol) of TBTU. The medium is stirred for 12 hours at room temperature. A further 0.3 mL of 2,2,2-trifluoroethylamine is then added and the medium is heated at 40° C. for 6 hours. The medium is taken up in 20 mL of DCM, washed successively with water (2×10 mL) and brine (20 mL), dried over $Na_2SO_4$ and concentrated under reduced pressure, and then purified by chromatography on a column of silica gel, eluting with a cyclohexane/EtOAc gradient of 0 to 10% EtOAc. 32 mg of 3-(2-{5-[cyclopentyl(methyl)sulfamoyl]pyridin-2-yl}-3-oxo-2,3-dihydro-1H-pyrazol-4-yl)-3-phenyl-N-(2,2,2-trifluoroethyl)propanamide are thus obtained in the form of a powder.

Yield=14%
m.p. (° C.)=80
M=$C_{25}H_{28}F_3N_5O_4S$=551; M+H=552; Method 2: Tr=1.21 min.
$^1$H NMR, d6-DMSO, 400 MHz, δ (ppm): 12 (bs, 1H); 8.8 (s, 1H); 8.6 (t, 2H); 8.25 (d, 1H); 7.7 (s, 1H); 7.4-7.2 (m, 5H); 4.3 (q, 2H); 3.9 (m, 2H); 3.0 (m, 1H); 2.8 (m, 1H); 2.7 (s, 3H); 1.6-1.3 (m, 8H)

EXAMPLE 34

6-(4-benzyl-5-oxo-2,5-dihydro-1H-pyrazol-1-yl)-N-cyclopentyl-N-[3-hydroxy-2-(hydroxymethyl)propyl]pyridine-3-sulfonamide (Compound 147 of Table I)

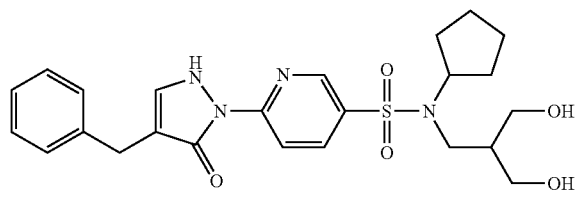 [SMILES: O=c1c(Cc2ccccc2)c[nH]n1-c1ccc(S(=O)(=O)N(CC(CO)CO)C2CCCC2)cn1]

34.1. (2,2-dimethyl-1,3-dioxan-5-yl) methyl 4-methylbenzenesulfonate

To a solution of 1.5 g (10.26 mmol) of (2,2-dimethyl-1,3-dioxan-5-yl)methanol and 1.71 mL of $Et_3N$ in 15 mL of DCM, cooled to 0° C., are added 2.15 g (11.3 mmol) of tosyl chloride. The medium is allowed to warm to room temperature, and stirring is continued for 1 hour. The medium is taken up in 100 mL of DCM, washed successively with 0.11N HCl (2×20 mL) and brine (20 mL), dried over $Na_2SO_4$, concentrated under reduced pressure and then purified by chromatography on a column of silica gel, eluting with a 99/1 DCM/MeOH mixture. 3 g of (2,2-dimethyl-1,3-dioxan-5-yl)methyl 4-methylbenzenesulfonate are obtained in the form of a colourless oil.

Yield=97%
$^1$H NMR, CDCl$_3$, 400 MHz, δ (ppm): 7.8 (d, 2H); 7.3 (d, 2H); 4.1 (d, 2H); 3.9 (dd, 2H); 3.6 (dd, 2H); 2.4 (s, 3H); 1.9 (m, 1H); 1.4 (s, 3H); 1.2 (s, 3H)

34.2. N-[(2,2-dimethyl-1,3-dioxan-5-yl)methyl]cyclopentanamine

A mixture of 1.5 g (5 mmol) of (2,2-dimethyl-1,3-dioxan-5-yl)methyl 4-methylbenzenesulfonate and 10 mL (101 mmol) of cyclopentylamine is heated for 12 hours at 80° C. The medium is concentrated under reduced pressure and then taken up in 200 mL of $Et_2O$, washed with water (2×50 mL), dried over $Na_2SO_4$ and concentrated under reduced pressure. 1 g of N-[(2,2-dimethyl-1,3-dioxan-5-yl)methyl]cyclopentanamine is obtained in the form of an oil, which is used in the following step without further purification.

Yield=100%

34.3. N-cyclopentyl-N-[(2,2-dimethyl-1,3-dioxan-5-yl)methyl]-6-hydrazinylpyridine-3-sulfonamide The compound is prepared according to processes 14.1 and 5.2, starting with N-[(2,2-dimethyl-1,3-dioxan-5-yl)methyl]cyclopentanamine, 6-chloropyridine-3-sulfonyl chloride and hydrazine hydrate.

Yield: 70%
$^1$H NMR, d6-DMSO, 400 MHz, δ (ppm): 8.5 (s, 1H); 8.25 (s, 1H); 8.0 (s, 1H); 7.8 (d, 1H); 7.7 (s, 1H); 7.2 (d, 1H); 6.8 (d, 1H); 4.4 (s, 1H); 4.2 (m, 1H); 3.9 (dd, 2H); 3.6 (dd, 2H); 3.0 (dd, 2H); 2.0 (m, 1H); 1.9 (d, 2H); 1.6-1.4 (m, 4H); 1.3 (s, 3H); 1.2 (s, 3H)

34.4. 6-(4-benzyl-5-oxo-2,5-dihydro-1H-pyrazol-1-yl)-N-cyclopentyl-N-[3-hydroxy-2-(hydroxymethyl)propyl]pyridine-3-sulfonamide According to the process described in Example 11, starting with 0.485 g of N-cyclopentyl-N-[(2,2-dimethyl-1,3-dioxan-5-yl)methyl]-6-hydrazinylpyridine-3-sulfonamide and 0.242 g of methyl 2-benzyl-3-oxopropanoate, 79 mg of 6-(4-benzyl-5-oxo-2,5-dihydro-1H-pyrazol-1-yl)-N-cyclopentyl-N-[3-hydroxy-2-(hydroxymethyl)propyl]pyridine-3-sulfonamide are obtained in the form of a powder.

Yield=14%
m.p. (° C.)>260
M=$C_{24}H_{30}N_4O_5S$=486; M+H=487; Method 2: Tr=2.09 min.
$^1$H NMR, d6-DMSO, 400 MHz, δ (ppm): 12 (bs, 1H); 8.8 (s, 1H); 8.6 (t, 2H); 8.25 (d, 1H); 7.7 (s, 1H); 7.4-7.2 (m, 5H); 4.3 (q, 2H); 3.9 (m, 2H); 3.0 (m, 1H); 2.8 (m, 1H); 2.7 (s, 3H); 1.6-1.3 (m, 8H)

EXAMPLE 35 methyl 3-(2-[5-(tert-butylsulfamoyl)pyridin-2-yl]-3-oxo-2,3-dihydro-1H-pyrazol-4-yl)-3-(pyridin-3-yl) propanoate (Compound 154 of Table I)

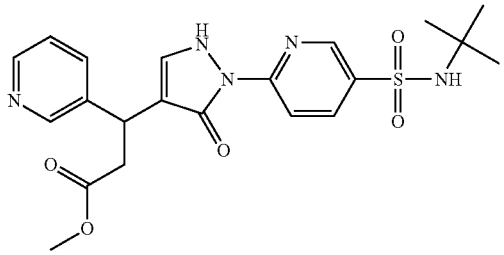 [SMILES: COC(=O)CC(c1cccnc1)c1c[nH]n(-c2ccc(S(=O)(=O)NC(C)(C)C)cn2)c1=O]

35.1. diethyl (2Z)-3-(pyridin-3-yl)pent-2-enedioate

To a solution of 15 mL (85.6 mmol) of diethyl (2E)-pent-2-enedioate in 5 mL of anhydrous DMF are added, under a stream of argon, 0.62 g (2.8 mmol) of Pd(OAc)$_2$, 1.7 g (5.56 mmol) of P(OTol)$_3$ and 5.5 mL (39.7 mmol) of Et$_3$N, the medium is then heated to 40° C. and 4 mL (39.75 mmol) of 3-bromopyridine are added. The medium is then heated for 24 hours at 90° C., and then taken up in 100 mL of EtOAc, washed with 100 mL of water, dried over Na$_2$SO$_4$, concentrated under reduced pressure and purified by chromatography on a column of silica gel, eluting with a cyclohexane/EtOAc gradient of 0 to 10% EtOAc. 9.12 g of diethyl (2Z)-3-(pyridin-3-yl)pent-2-enedioate are obtained in the form of a yellow wax.

Yield=87%

$^1$H NMR, CDCl$_3$, 400 MHz, δ (ppm) 8.8 (s, 1H); 8.6 (d, 1H); 7.8 (dd, 1H); 7.4 (dd, 1H); 6.3 (s, 1H); 4.2 (q, 2H); 4.15 (s, 2H); 4.1 (q, 2H); 1.3 (t, 3H); 1.2 (t, 3H)

35.2. diethyl 2-formyl-3-(pyridin-3-yl)pentanedioate

The compound is prepared according to processes 21.2 and 14.2, starting with diethyl (2Z)-3-(pyridin-3-yl)pent-2-enedioate.

Yield: 18%

35.3. methyl 3-{2-[5-(tert-butylsulfamoyl)pyridin-2-yl]-3-oxo-2,3-dihydro-1H-pyrazol-4-yl}-3-(pyridin-3-yl)propanoate According to processes 22.5 to 22.7, starting with 88 mg of diethyl 2-formyl-3-(pyridin-3-yl)pentanedioate and 74 mg of N-tert-butyl-6-hydrazinylpyridine-3-sulfonamide, followed by free-drying of the compound obtained in the presence of 1 eq. of 0.1N HCl, 17 mg of methyl 3-{2-[5-(tert-butylsulfamoyl)pyridin-2-yl]-3-oxo-2,3-dihydro-1H-pyrazol-4-yl}-3-(pyridin-3-yl)propanoate hydrochloride are obtained in the form of a green lyophilizate.

Yield=17% m.p. (° C.)=146.

M=C$_{21}$H$_{25}$N$_5$O$_5$S=459; M+H=460; Method 2: Tr=1.19 min.

$^1$H NMR, d6-DMSO, 400 MHz, δ (ppm): 12.5 (bs, 1H); 8.8 (s, 1H); 8.7 (bs, 1H); 8.6 (d, 1H); 8.4 (bs, 1H); 8.3 (d, 1H); 8.2 (d, 1H); 7.9 (s, 1H); 7.8 (t, 1H); 7.6 (s, 1H); 4.3 (t, 1H); 3.5 (s, 3H); 3.2 (m, 2H); 1.0 (s, 9H)

Tables I and II below illustrate the chemical structures and the physical properties of a few examples of compounds according to the invention.

Table I illustrates compounds of formula (I) according to the invention in which R represents —SO$_2$—NR3R4. These compounds are referred to hereinbelow as compounds of formula (I').

Table II illustrates compounds of formula (I) according to the invention in which R is as defined in the said table. These compounds are referred to hereinbelow as compounds of formula (I'').

Tables I and II below illustrate the chemical structures and the physical properties of a few examples of compounds according to the invention.

In these tables:

in the "salt" column, "-" represents a compound in free base form, whereas

"CF$_3$COOH", "HCl" and "Na" represent, respectively, a compound in the form of the trifluoroacetic acid salt, in the form of the hydrochloride salt and in the form of the sodium salt;

in the other columns, "-" means that the substituent under consideration is not present on the molecule;

Me, Et, n-Pr, i-Pr, n-Bu and i-Bu represent, respectively, the methyl, ethyl, n-propyl, isopropyl, n-butyl and isobutyl groups;

Ph and Bn represent, respectively, the phenyl and benzyl groups;

the "m.p." column indicates the melting point, in ° C., of the compound under consideration;

the peak MW identified by mass spectrometry, and the high-performance liquid chromatography analytical methods used and detailed previously, are indicated, respectively, in the "LC/MS" column and the "Method" column.

TABLE I (I')

| No. | R1 | R2 | R3 | R4 | Salt | m.p. | LC-MS MH+ | method |
|-----|----|----|----|----|------|------|-----------|--------|
| 1 | 2-chlorobenzyl | Me | piperidinyl (cyclic NR3R4) | | CF$_3$CO$_2$H | 202 | 463 | 1 |

TABLE I-continued (I')

| No. | R1 | R2 | R3 | R4 | Salt | m.p. | LC-MS MH+ | method |
|---|---|---|---|---|---|---|---|---|
| 2 | 2-Cl-benzyl | Me | (2,6-dimethylcyclohexyl) | | — | 170 | 476 | 1 |
| 3 | 2-Cl-benzyl | Me | Et | Et | — | 58 | 436 | 1 |
| 4 | 2-Cl-benzyl | Me | Et | phenyl | — | 260 | 484 | 1 |
| 5 | 2-Cl-benzyl | Me | iPr | iPr | — | 212 | 464 | 1 |
| 6 | 2-Cl-benzyl | Me | (cyclohexyl) | | — | 190 | 448 | 1 |
| 7 | 2-F-benzyl | Me | Et | Et | — | 158 | 420 | 1 |

TABLE I-continued (I')

| No. | R1 | R2 | R3 | R4 | Salt | m.p. | LC-MS MH+ | method |
|---|---|---|---|---|---|---|---|---|
| 8 | 2-F-benzyl | Me | \-N-methylpiperidin-4-yl (R3,R4 cyclic) | | CF$_3$CO$_2$H | 210 | 447 | 1 |
| 9 | 2-F-benzyl | Me | 3,5-dimethylpiperidinyl (R3,R4 cyclic) | | — | 230 | 460 | 1 |
| 10 | 2-F-benzyl | Me | Et | phenyl | — | 215 | 468 | 1 |
| 11 | 2-F-benzyl | Me | piperidinyl (R3,R4 cyclic) | | — | 198 | 432 | 1 |
| 12 | 2,4-diCl-benzyl | Me | N-methylpiperidin-4-yl (R3,R4 cyclic) | | CF$_3$CO$_2$H | 176 | 496 | 1 |
| 13 | 2,4-diCl-benzyl | Me | 3,5-dimethylpiperidinyl (R3,R4 cyclic) | | — | 212 | 509 | 1 |

TABLE I-continued (I')

| No. | R1 | R2 | R3 | R4 | Salt | m.p. | LC-MS MH+ | method |
|---|---|---|---|---|---|---|---|---|
| 14 | 2,4-dichlorobenzyl | Me | Et | phenyl | — | 178 | 517 | 1 |
| 15 | 2,4-dichlorobenzyl | Me | iPr | iPr | — | 226 | 497 | 1 |
| 16 | 2,4-dichlorobenzyl | Me | cyclohexyl (R3+R4) | | — | 212 | 481 | 1 |
| 17 | 2-chloro-6-fluorobenzyl | Me | N-methylpiperidinyl (R3+R4) | | CF$_3$CO$_2$H | 172 | 481 | 1 |
| 18 | 2-chloro-6-fluorobenzyl | Me | cis-3,5-dimethylcyclohexyl (R3+R4) | | — | 240 | 494 | 1 |
| 19 | 2-chloro-6-fluorobenzyl | Me | Et | Et | — | 170 | 454 | 1 |

TABLE I-continued (I')

| No. | R1 | R2 | R3 | R4 | Salt | m.p. | LC-MS MH+ | method |
|---|---|---|---|---|---|---|---|---|
| 20 | 2-Cl-6-F-benzyl | Me | phenyl | Et | — | 206 | 502 | 1 |
| 21 | 2-Cl-6-F-benzyl | Me | iPr | iPr | — | 80 | 482 | 1 |
| 22 | 2-Cl-6-F-benzyl | Me | cyclohexyl | | — | 60 | 466 | 1 |
| 23 | 4-Cl-benzyl | Me | N-methylpiperidin-4-yl | | CF$_3$CO$_2$H | 158 | 463 | 1 |
| 24 | 4-Cl-benzyl | Me | 2,6-dimethylcyclohexyl | | — | 252 | 476 | 1 |
| 25 | 4-Cl-benzyl | Me | Et | Et | — | 196 | 436 | 1 |

TABLE I-continued
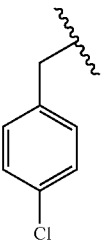 [SMILES: *Cc1ccc(Cl)cc1]
(I')
| No. | R1 | R2 | R3 | R4 | Salt | m.p. | LC-MS MH+ | method |
|---|---|---|---|---|---|---|---|---|
| 26 | 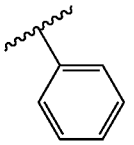 [SMILES: *c1ccccc1] | Me | Et | 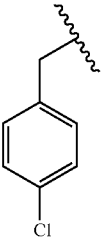 [SMILES: *Cc1ccc(Cl)cc1] | — | 202 | 484 | 1 |
| 27 | 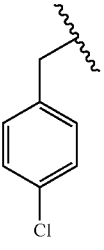 [SMILES: *Cc1ccc(Cl)cc1] | Me | iPr | iPr | — | 220 | 464 | 1 |
| 28 | 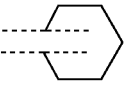 | Me | 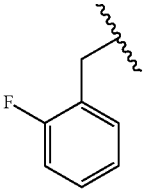 [SMILES: *Cc1ccccc1F] | | — | 228 | 448 | 1 |
| 29 | 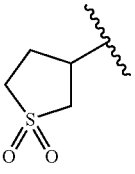 [SMILES: *C1CCS(=O)(=O)C1] | Me | iPr | iPr | — | 82 | 448 | 1 |
| 30 | 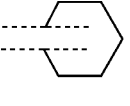 | Me | 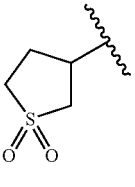 [SMILES: *C1CCS(=O)(=O)C1] | | — | 250 | 442 | 1 |
| 31 | 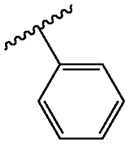 [SMILES: *c1ccccc1] | Me | Et | 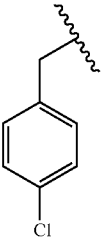 [SMILES: *Cc1ccc(Cl)cc1] | — | 264 | 478 | 1 |

TABLE I-continued (I')

| No. | R1 | R2 | R3 | R4 | Salt | m.p. | LC-MS MH+ | method |
|---|---|---|---|---|---|---|---|---|
| 32 | (tetrahydrothiophene 1,1-dioxide-3-yl) | Me | iPr | iPr | — | 200 | 458 | 1 |
| 33 | 4-(methoxymethyl)benzyl | Me | Et | phenyl | — | 177 | 494 | 2 |
| 34 | 3-(methoxymethyl)benzyl | Me | Et | phenyl | — | 144 | 494 | 2 |
| 35 | 3-cyanobenzyl | Me | Et | phenyl | — | 198 | 475 | 2 |
| 36 | 4-cyanobenzyl | Me | Et | phenyl | — | 218 | 475 | 2 |

TABLE I-continued (I')

| No. | R1 | R2 | R3 | R4 | Salt | m.p. | LC-MS MH+ | method |
|---|---|---|---|---|---|---|---|---|
| 37 | 2-CN-benzyl | Me | Et | phenyl | — | 112 | 475 | 2 |
| 38 | 3-(2-methoxyethoxy)-benzyl | Me | Et | phenyl | — | 126 | 523 | 2 |
| 39 | 4-(SO2Me)-benzyl | Me | Et | phenyl | — | 224 | 527 | 2 |
| 40 | 4-pyridylmethyl | Me | Et | phenyl | HCl | 192 | 451 | 2 |
| 41 | 2-pyridylmethyl | Me | Et | phenyl | HCl— | 150 | 451 | 2 |

TABLE I-continued (I')

| No. | R1 | R2 | R3 | R4 | Salt | m.p. | LC-MS MH+ | method |
|---|---|---|---|---|---|---|---|---|
| 42 | benzyl | Me | Et | phenyl | — | 212 | 449 | 2 |
| 43 | (pyridin-3-yl)methyl | Me | Et | phenyl | HCl | 128 | 451 | 2 |
| 44 | (2,5-dimethoxyphenyl)methyl | Me | Et | phenyl | — | 140 | 509 | 2 |
| 45 | (4-trifluoromethylphenyl)methyl | Me | Et | phenyl | — | 222 | 518 | 2 |
| 46 | (3-trifluoromethylphenyl)methyl | Me | Et | phenyl | — | 178 | 518 | 2 |
| 47 | (3,5-dimethoxyphenyl)methyl | Me | Et | phenyl | — | 162 | 509 | 2 |

TABLE I-continued (I')

| No. | R1 | R2 | R3 | R4 | Salt | m.p. | LC-MS MH+ | method |
|---|---|---|---|---|---|---|---|---|
| 48 | 4-hydroxybenzyl | Me | Et | phenyl | — | 208 | 465 | 2 |
| 49 | 4-(2-dimethylaminoethoxy)benzyl | Me | Et | phenyl | — | 178 | 536 | 2 |
| 50 | 4-dimethylaminobenzyl | Me | Et | phenyl | — | 182 | 492 | 2 |
| 51 | 2-trifluoromethylbenzyl | Me | Et | phenyl | — | 172 | 480 | 2 |
| 52 | benzyl | Me | H | —(CH$_2$)$_2$CH(CH$_3$)$_2$ | HCl | 100 | 416 | 2 |

TABLE I-continued (I')

| No. | R1 | R2 | R3 | R4 | Salt | m.p. | LC-MS MH+ | method |
|---|---|---|---|---|---|---|---|---|
| 53 | 3-(dimethylamino)benzyl | Me | Et | phenyl | — | 122 | 491 | 2 |
| 54 | 4-methoxybenzyl | Me | Et | phenyl | — | 188 | 479 | 2 |
| 55 | 3-methoxybenzyl | Me | Et | phenyl | — | 146 | 479 | 2 |
| 56 | 3-(2-(dimethylamino)ethoxy)benzyl | Me | Et | phenyl | HCl | 124 | 537 | 2 |
| 57 | 2-methoxybenzyl | Me | Et | phenyl | — | 108 | 479 | 2 |
| 58 | benzyl | Me | morpholino (R3+R4) | | — | 196 | 416 | |

TABLE I-continued (I')

| No. | R1 | R2 | R3 | R4 | Salt | m.p. | LC-MS MH+ | method |
|---|---|---|---|---|---|---|---|---|
| 59 | 3-hydroxybenzyl | Me | Et | phenyl | — | 202 | 466 | 2 |
| 60 | benzyl | Et | Et | phenyl | — | 194 | 464 | 2 |
| 61 | 4-(2-methoxyethoxy)benzyl | Me | Et | phenyl | — | 176 | 523 | 2 |
| 62 | benzyl | Me | cyclohexyl (R3,R4 joined) | | HCl | 195 | 400 | 2 |
| 63 | benzyl | Me | cycloheptyl (R3,R4 joined) | | HCl | 182 | 428 | 2 |
| 64 | 3-pyridylmethyl | Me | Et | Et | — | 166 | 403 | 2 |

TABLE I-continued
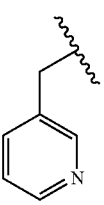 [SMILES: *Cc1cccnc1]
(I')
| No. | R1 | R2 | R3 | R4 | Salt | m.p. | LC-MS MH+ | method |
|---|---|---|---|---|---|---|---|---|
| 65 | 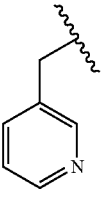 [SMILES: *Cc1cccnc1] | Me | Et | Et | HCl | 154 | 403 | 2 |
| 66 | 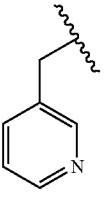 [SMILES: *Cc1cccnc1] | Me | Me | Me | — | 212 | 375 | 2 |
| 67 | 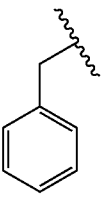 [SMILES: *Cc1ccccc1] | Me | Me | Me | HCl | 170 | 375 | 2 |
| 68 | 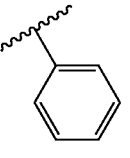 | nPr | Et | 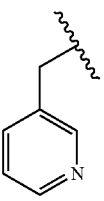 [SMILES: *Cc1cccnc1] | — | 180 | 477 | 2 |
| 69 | 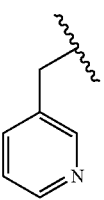 [SMILES: *Cc1cccnc1] | Me | H | iPr | HCl | 228 | 389 | 2 |
| 70 |  | Me | | | HCl | 180 | 401 | 2 |

TABLE I-continued (I')

| No. | R1 | R2 | R3 | R4 | Salt | m.p. | LC-MS MH+ | method |
|-----|----|----|----|----|------|------|-----------|--------|
| 71 | 3-pyridylmethyl | Me | H | t-Bu | HCl | 230 | 403 | 2 |
| 72 | 3-pyridylmethyl | Me | H | cyclopropyl | HCl | 206 | 387 | 2 |
| 73 | 3-pyridylmethyl | Me | H | cyclopentyl | HCl | 242 | 415 | 2 |
| 74 | 2-phenylethyl | Me | Et | phenyl | — | 158 | 463 | 2 |
| 75 | 3-pyridylmethyl | Me | Me | 2-pyridyl | HCl | 106 | 438 | 2 |
| 76 | 3-pyridylmethyl | Me | | 4-benzylcyclohexyl | HCl | 160 | 505 | 2 |

TABLE I-continued

| No. | R1 | R2 | R3 | R4 | Salt | m.p. | LC-MS MH+ | method |
|---|---|---|---|---|---|---|---|---|
| 77 | (2-phenylpropan-2-yl) | Me | Et | phenyl | — | 122 | 477 | 2 |
| 78 | ((6-methoxypyridin-2-yl)methyl) | Me | Et | phenyl | — | 174 | 480 | 2 |
| 79 | (pyridin-3-ylmethyl) | Me | H | (pyridin-2-yl) | HCl | 174 | 424 | 2 |
| 80 | (1-phenylcyclopropyl) | Me | Et | phenyl | — | 146 | 475 | 2 |
| 81 | ((3-methoxypyridin-2-yl)methyl) | Me | Et | phenyl | — | 130 | 480 | 2 |
| 82 | (benzyl) | —CH₂—OMe | Et | phenyl | — | 158 | 479 | 2 |
| 83 | (benzyl) | —CF₃ | Et | phenyl | — | 186 | 503 | 3 |

TABLE I-continued (I')

![Structure: pyrazolone-pyridine-sulfonamide with R1, R2, R3, R4 substituents]

| No. | R1 | R2 | R3 | R4 | Salt | m.p. | LC-MS MH+ | method |
|---|---|---|---|---|---|---|---|---|
| 85 | pyridin-2-ylmethyl (CH2-2-pyridyl) | Me | Et | phenyl | — | 188 | 464 | 2 |
| 86 | (5-methoxypyridin-3-yl)methyl | Me | Et | phenyl | — | 138 | 480 | 2 |
| 87 | pyridin-3-ylmethyl | Me | Me | —(CH$_2$)$_2$—OMe | — | 136 | 418 | 2 |
| 88 | benzyl | i-Bu | Et | phenyl | — | 138 | 491 | 2 |
| 89 | pyridin-3-ylmethyl | Me | H | Et | HCl | 196 | 374 | 2 |
| 90 | pyridin-3-ylmethyl | Me | H | phenyl | HCl | 154 | 422 | 2 |
| 92 | 3-phenylpropyl | Me | Et | phenyl | — | 158 | 477 | 2 |

TABLE I-continued (I')

R2, R1 on pyrazolone ring linked to pyridine-sulfonamide with R3, R4 substituents.

| No. | R1 | R2 | R3 | R4 | Salt | m.p. | LC-MS MH+ | method |
|---|---|---|---|---|---|---|---|---|
| 93 | benzyl | H | Et | phenyl | HCl | 180 | 435 | 2 |
| 94 | (1-methylpiperidin-4-yl)methyl | Me | Et | phenyl | HCl | 150 | 470 | 2 |
| 95 | (pyridin-3-yl)methyl | Me | Me | cyclopropyl | HCl | 138 | 400 | 2 |
| 96 | (5-methoxypyridin-3-yl)methyl | Me | H | tBu | HCl | 150 | 432 | 2 |
| 97 | (5-cyanopyridin-3-yl)methyl | Me | Et | phenyl | — | 164 | 475 | 2 |
| 98A | (pyridin-3-yl)methyl | H | H | tBu | — | 220 | 388 | 2 |
| 98B | (pyridin-3-yl)methyl | H | H | tBu | HCl | 140 | 388 | 2 |

TABLE I-continued
(I')
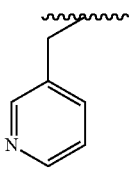 [SMILES: *Cc1cccnc1]
| No. | R1 | R2 | R3 | R4 | Salt | m.p. | LC-MS MH+ | method |
|---|---|---|---|---|---|---|---|---|
| 99 | 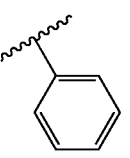 [SMILES: *c1ccccc1] | H | Et | 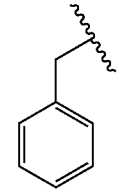 | HCl | 142 | 436 | 2 |
| 100 | 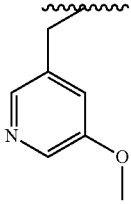 | H | Me | tBu | — | 186 | 401 | 2 |
| 101 | 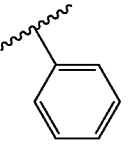 [SMILES: *c1ccccc1] | H | Et | 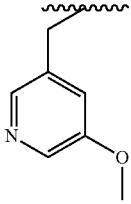 [SMILES: *Cc1cncc(OC)c1] | HCl | 136 | 466 | 2 |
| 102 | 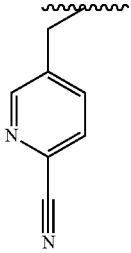 [SMILES: *Cc1ccc(C#N)nc1] | Me | Me | tBu | — | 84 | 446 | 2 |
| 103 | 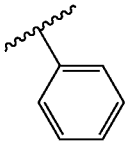 [SMILES: *c1ccccc1] | Me | Et | 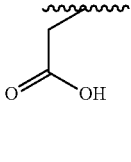 | — | 120 | 475 | 2 |
| 104 | 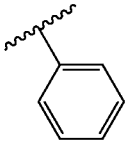 [SMILES: *c1ccccc1] | H | Et | 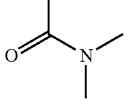 | — | 174 | 403 | 2 |
| 105 | 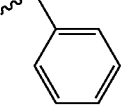 | H | Et |  | — | 168 | 430 | 2 |

TABLE I-continued (I')

| No. | R1 | R2 | R3 | R4 | Salt | m.p. | LC-MS MH+ | method |
|---|---|---|---|---|---|---|---|---|
| 106 | benzyl | -CH2C(O)OEt | Et | phenyl | — | 156 | 521 | 2 |
| 107 | -CH2C(O)OMe | H | Et | phenyl | — | 140 | 417 | 2 |
| 108 | -CH2C(O)NHMe | H | Et | phenyl | — | 194 | 416 | 2 |
| 109 | benzyl | -CH2C(O)N(Me)2 | Et | phenyl | — | 163 | 520 | 2 |
| 110 | -CH2CH2C(O)OH | H | Et | phenyl | — | 214 | 417 | 2 |
| 111 | 3-(methoxycarbonyl)benzyl | Me | Et | phenyl | — | 172 | 507 | 2 |
| 112 | -CH2CH2C(O)OMe | H | Et | phenyl | — | 128 | 431 | 2 |

TABLE I-continued
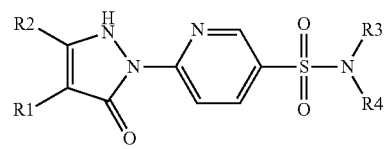
(I')
| No. | R1 | R2 | R3 | R4 | Salt | m.p. | LC-MS MH+ | method |
|---|---|---|---|---|---|---|---|---|
| 113 | methyl 2-phenylacetate-α-yl | H | H | tBu | — | 66 | 445 | 2 |
| 114 | methyl 3-phenylpropanoate-3-yl | H | Me | cyclopentyl | — | 80 | 485 | 3 |
| 115 | pyridin-3-ylmethyl | H | Et | cyclopentyl | HCl | 110 | 428 | 2 |
| 116 | 2-(methoxycarbonyl)benzyl | Me | Et | phenyl | — | 146 | 507 | 2 |
| 117 | pyridin-3-ylmethyl | H | Me | cyclopentyl | HCl | 124 | 414 | 2 |
| 118 | 2-carboxylatobenzyl | Me | Et | phenyl | 2 Na | >260 | 491 | 2 |
| 119 | pyridin-4-ylmethyl | H | Et | cyclopentyl | HCl | 115 | 428 | 2 |

TABLE I-continued (I')

R2-pyrazolone-pyridine-sulfonamide structure with R1, R3, R4 substituents

| No. | R1 | R2 | R3 | R4 | Salt | m.p. | LC-MS MH+ | method |
|---|---|---|---|---|---|---|---|---|
| 120 | 4-pyridyl-CH2- | H | Me | cyclopentyl | HCl | 130 | 414 | 2 |
| 122 | 3-pyridyl-CH2- | H | Me | —CH2_t-Bu | — | 175 | 416 | 2 |
| 123 | benzyl | H | —(CH2)3—N(Me)2 | cyclopentyl | HCl | 230 | 484 | 2 |
| 124 | benzyl | H | —(CH2)2—OH | cyclopentyl | — | 152 | 443 | 2 |
| 125 | benzyl | H | —(CH2)3—OH | cyclopentyl | — | 138 | 457 | 2 |
| 126 | benzyl | H | —(CH2)3—O—CH2—Ph | cyclopentyl | — | 116 | 547 | 2 |
| 127 | benzyl | H | —(CH2)2—O—CH2—Ph | cyclopentyl | — | 100 | 533 | 2 |

TABLE I-continued (I')

| No. | R1 | R2 | R3 | R4 | Salt | m.p. | LC-MS MH+ | method |
|-----|----|----|----|----|----|------|-----------|--------|
| 128 | 3-pyridylmethyl | H | —CH₂CO₂Me | cyclopentyl | HCl | 110 | 472 | 2 |
| 129 | 3-pyridylmethyl | H | cycloheptyl (spiro, R3+R4) | | — | 190 | 414 | 2 |
| 131 | 3-pyridylmethyl | H | Me | cis-2-(methoxycarbonyl)cyclopentyl | HCl | 156 | 472 | 2 |
| 132 | benzyl | H | —CH₂—CH₂—NMe₂ | cyclopentyl | HCl | 192 | 470 | 2 |
| 133 | benzyl | H | 1-methylpiperidin-4-yl (R3+R4) | | HCl | 200 | 414 | 2 |
| 134 | cyclopentylmethyl | H | Et | benzyl | — | 170 | 427 | 2 |
| 135 | benzyl | H | 1-methylazepan-4-yl (R3+R4) | | HCl | 200 | 428 | 2 |
| 136 | 3-pyridylmethyl | H | H | neopentyl | HCl | 123 | 402 | 2 |

TABLE I-continued
(I')
| No. | R1 | R2 | R3 | R4 | Salt | m.p. | LC-MS MH+ | method |
|-----|----|----|----|----|------|------|-----------|--------|
| 137 | 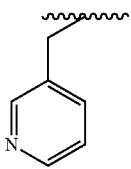 [SMILES: *Cc1cccnc1] (3-pyridylmethyl) | H | H | 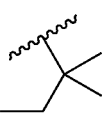 | HCl | 126 | 402 | 2 |
| 138 | 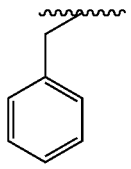 [SMILES: *Cc1ccccc1] (benzyl) | H | Me | 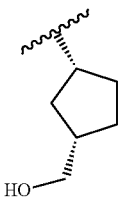 [SMILES: *[C@@H]1CC[C@H](CO)C1] | — | 108 | 443 | 2 |
| 139 | 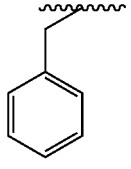 [SMILES: *Cc1ccccc1] (benzyl) | H | Me | 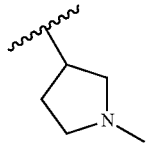 [SMILES: *C1CCN(C)C1] | HCl | 130 | 428 | 2 |
| 140 | 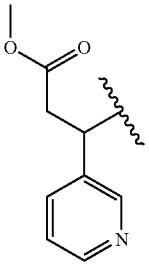 [SMILES: *C(CC(=O)OC)c1cccnc1] | H | Me | 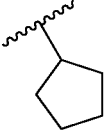 [SMILES: *C1CCCC1] | HCl | 124 | 485 | 2 |
| 141 | 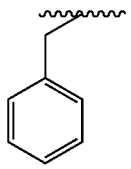 [SMILES: *Cc1ccccc1] (benzyl) | H | H | 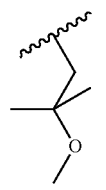 [SMILES: *CC(C)(C)OC] | HCl | 194 | 417 | 2 |
| 142 | 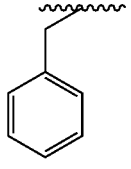 [SMILES: *Cc1ccccc1] (benzyl) | H | 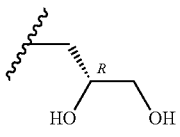 | 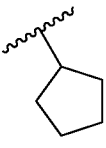 [SMILES: *C1CCCC1] | — | 184 | 473 | 2 |
| 143 | 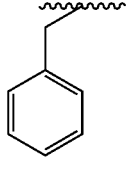 [SMILES: *Cc1ccccc1] (benzyl) | H | —CH$_2$—CHOH—CH$_2$OH | 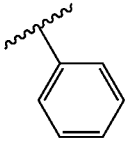 [SMILES: *c1ccccc1] | — | 174 | 481 | 2 |

TABLE I-continued
(I')
| No. | R1 | R2 | R3 | R4 | Salt | m.p. | LC-MS MH+ | method |
|---|---|---|---|---|---|---|---|---|
| 144 | 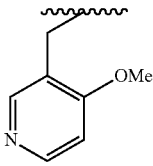 [SMILES: *Cc1cnccc1OC] | H | Me | 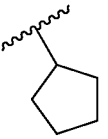 [SMILES: *C1CCCC1] | HCl | 40 | 444 | 2 |
| 145 | 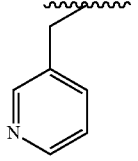 [SMILES: *Cc1cccnc1] | H | Me | 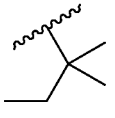 | — | 162 | 416 | 2 |
| 146 | 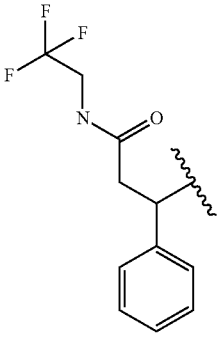 [SMILES: *C(CC(=O)NCC(F)(F)F)c1ccccc1] | H | Me | 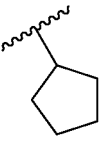 | — | 80 | 552 | 2 |
| 147 | 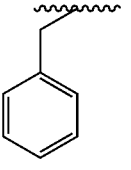 [SMILES: *Cc1ccccc1] | H | 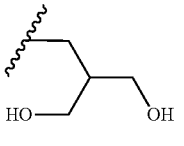 [SMILES: *CC(CO)CO] | 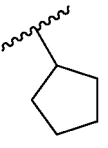 | — | >260 | 487 | 2 |
| 148 | 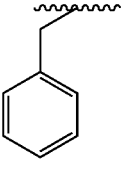 [SMILES: *Cc1ccccc1] | H | 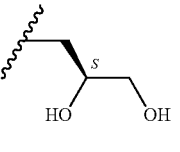 | 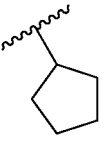 | — | 184 | 473 | 2 |
| 149 | 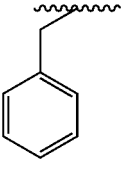 | H | H | 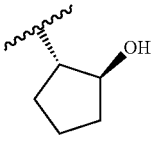 [SMILES: *[C@H]1CCC[C@@H]1O] | — | 176 | 415 | 2 |
| 150 | 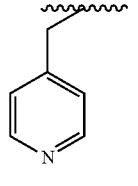 [SMILES: *Cc1ccncc1] | H | H | 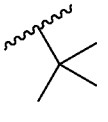 [SMILES: *C(C)(C)C] | — | 226 | 388 | 2 |

TABLE I-continued (I')

| No. | R1 | R2 | R3 | R4 | Salt | m.p. | LC-MS MH+ | method |
|---|---|---|---|---|---|---|---|---|
| 151 | benzyl | H | | N,N-dimethylaminocyclopentyl | HCl | 198 | 428 | 2 |
| 152 | benzyl | H | H | neopentyl-N,N-dimethylamine | HCl | 230 | 430 | 2 |
| 153 | benzyl | H | Me | phenyl | — | 198 | 421 | 2 |
| 154 | methyl 3-(pyridin-3-yl)propanoate | H | H | tert-butyl | HCl | 146 | 460 | 2 |
| 155 | ethyl 3-phenylpropanoate | H | H | tert-butyl | — | 130 | 473 | 2 |
| 156 | benzyl | H | —CH₂—CHOH—CH₂OH | tert-butyl | — | >260 | 461 | 2 |

TABLE I-continued (I')

| No. | R1 | R2 | R3 | R4 | Salt | m.p. | LC-MS MH+ | method |
|-----|----|----|----|----|------|------|-----------|--------|
| 157 | benzyl | H | H | 3-hydroxypropyl | — | 180 | 375 | 2 |
| 158 | benzyl | H | —CH₂—CHOH—CH₂OH | cyclopentyl | — | 168 | 473 | 2 |
| 159 | (pyridin-3-yl)methyl | Me | \[cycloheptyl ring spanning R3/R4\] | | Na | >220 | 428 | 2 |
| 160 | (5-methoxypyridin-2-yl)methyl | Me | Me | tert-butyl | — | 165 | 446 | 2 |
| 161 | (pyridin-3-yl)methyl | H | —CH₂—CHOH—CH₂OH | benzyl | HCl | 148 | 482 | 2 |

TABLE II (I")

| No. | R1 | R2 | R | Salt | m.p. | LC-MS MH+ | method |
|---|---|---|---|---|---|---|---|
| 162 | 2-chlorobenzyl | Me | —CF₃ | — | | 368 | 1 |
| 163 | 2-chlorobenzyl | Me | —C(O)OH | | 246 | 381 | 2 |
| 164 | 2-chlorobenzyl | Me | H | — | | 300 | 1 |
| 165 | 2-fluorobenzyl | Me | H | — | | 284 | 1 |
| 166 | 2-fluorobenzyl | Me | —CF₃ | — | | 352 | 1 |
| 167 | 2,4-dichlorobenzyl | Me | H | — | | 334 | 1 |
| 168 | 2,4-dichlorobenzyl | Me | —CF₃ | — | | 402 | 1 |

TABLE II-continued (I'')

| No. | R1 | R2 | R | Salt | m.p. | LC-MS MH+ | method |
|---|---|---|---|---|---|---|---|
| 169 | 2-Cl,6-F-benzyl | Me | —CF₃ | — | | 386 | 1 |
| 170 | 2-Cl-benzyl | Me | —C(O)OMe | HCl | 258 | 358 | 2 |
| 171 | 4-Cl-benzyl | Me | H | — | | 300 | 1 |
| 172 | 2-CN-benzyl | Me | H | — | 157 | 291 | 2 |
| 173 | 4-CN-benzyl | Me | H | — | 154 | 291 | 2 |
| 174 | 3-(CH₂—OMe)-benzyl | Me | H | — | 55 | 493 | 2 |
| 175 | pyridin-4-ylmethyl | Me | H | — | 162 | 267 | 2 |

TABLE II-continued (I")

| No. | R1 | R2 | R | Salt | m.p. | LC-MS MH+ | method |
|---|---|---|---|---|---|---|---|
| 176 | (4-pyridylmethyl) | Me | H | HCl | 208 | 267 | 2 |
| 177 | (3-cyanobenzyl) | Me | H | — | 90 | 291 | 2 |
| 178 | (benzyl) | Me | —Br | — | 164 | 345 | 2 |
| 179 | (3,5-dimethoxybenzyl) | Me | H | — | 96 | 326 | 2 |
| 180 | (4-methylsulfonylbenzyl) | Me | H | — | 144 | 344 | 2 |
| 181 | (3-(2-methoxyethoxy)benzyl) | Me | H | — | 68 | 340 | 2 |
| 182 | (benzyl) | Me | H | — | 110 | 266 | 2 |

TABLE II-continued
(I'')
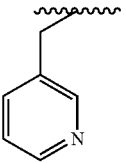 [SMILES: *Cc1cccnc1]
| No. | R1 | R2 | R | Salt | m.p. | LC-MS MH+ | method |
|---|---|---|---|---|---|---|---|
| 183 | 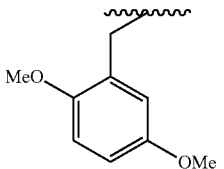 [SMILES: *Cc1cc(OC)ccc1OC] | Me | H | — | 80 | 267 | 2 |
| 184 | 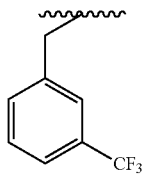 | Me | H | — | 62 | 326 | 2 |
| 185 | 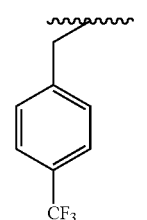 | Me | H | — | 78 | 334 | 2 |
| 186 | 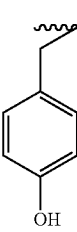 | Me | H | — | 94 | 334 | 2 |
| 187 | 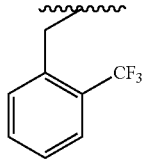 [SMILES: *Cc1ccccc1C(F)(F)F] | Me | H | — | 212 | 465 | 2 |
| 188 | 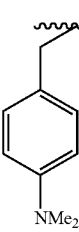 | Me | H | — | 106 | 334 | 2 |
| 189 |  | Me | H | — | 110 | 309 | 2 |

TABLE II-continued
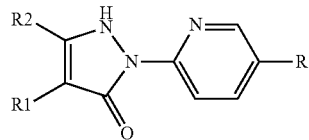
(I'')
| No. | R1 | R2 | R | Salt | m.p. | LC-MS MH+ | method |
|---|---|---|---|---|---|---|---|
| 190 | 3-NMe2-benzyl | Me | H | HCl | 132 | 309 | 2 |
| 191 | 4-OMe-benzyl | Me | H | — | 96 | 296 | 2 |
| 192 | 2-OMe-benzyl | Me | H | — | 254 | 296 | 2 |
| 193 | 3-OMe-benzyl | Me | H | — | 120 | 296 | 2 |
| 194 | 3-OH-benzyl | Me | H | — | 150 | 281 | 2 |
| 195 | benzyl | Et | H | — | 76 | 280 | 2 |
| 196 | phenethyl | Me | H | — | 128 | 280 | 2 |

TABLE II-continued (I")

| No. | R1 | R2 | R | Salt | m.p. | LC-MS MH+ | method |
|---|---|---|---|---|---|---|---|
| 197 | 3-pyridylmethyl | Me | phenylsulfonyl (O=S=O, Ph) | — | 176 | 407 | 2 |
| 198 | 3-pyridylmethyl | H | —CO2—CH2—tBu | — | 160 | 367 | 2 |
| 199 | 3-pyridylmethyl | Me | COO t-Bu | HCl | 156 | 367 | 2 |
| 200 | benzyl | H | —CO2—CH2—tBu | — | 130 | 366 | 2 |
| 201 | 4-pyridylmethyl | H | —CO2—CH2—tBu | — | 132 | 367 | 2 |
| 202 | 3-pyridylmethyl | H | CO2tBu | HCl | 160 | 353 | 2 |

The compounds according to the invention underwent pharmacological trials in order to determine their properties, with, in particular:

an in vitro test of direct measurement of stabilization of the protein HIF1-alpha, a transcription factor constitutively expressed in cells but degraded under normal oxygen conditions by the ubiquitin/proteasome system;

a functional test for measuring in He3pB cells the secretion of VEGF and EPO, which are two markers of activation of HIF1-alpha in hepatocytes.

These two tests are described below.

1. Measurement of the Stabilization of HIF1-Aloha in HEKEA Cells 1.1 Object

HIF is a transcription factor involved in the adaptation of cells to hypoxia. This transcription factor is at the minimum a heterodimer formed from two proteins, ARNT and HIF1-alpha. ARNT is constitutively and stably expressed in cells and the bulk of the transcription complex regulation is performed via stabilization of the protein HIF1-alpha. In point of fact, this protein, under normal oxygen conditions (20%, approximately equivalent to the value of ambient oxygen), is hydroxylated specifically on two prolines (proline 402 and 564 for the human protein) via HIF prolyl-hydroxylases, resulting in the binding of the von Hippell Lindau (VHL) protein. This binding of VHL to HIF1-alpha then causes the degradation of HIF1-alpha via the ubiquitin/proteasome system. Under hypoxia ($O_2$<5% in the cell tests), the HIF prolyl-hydroxylases are inhibited, which is reflected by an increase in the amount of HIF1-alpha protein in the cells. This protein can then combine with ARNT to transfer into the nucleus and activate its target genes.

Since the genes activated by HIF are involved in the adaptive response of cells to hypoxia and of tissues to ischaemia, the object is to identify and characterize compounds that stabilize HIF1-alpha in cells in order to amplify or mimic its beneficial effect.

Many tests exist describing the indirect measurement of the activity of HIF via reporter gene systems (HRE-luciferase) or via the measurement of HIF-induced proteins (for example VEGF or EPO). Furthermore, the only tests that allow direct measurement of the amount of HIF1-alpha protein in cells are tests using antibodies, for instance Western blotting comprising phases of cell extraction (total lysates or nuclear extracts) that are consuming in terms of cells and time, thus limiting the compound screening capacity. The object was thus to develop a sensitive screening test, adaptable to 384-well plates, for directly measuring the amount of HIF1-alpha protein in the nucleus of cells. This test was established in HEK cells (human epithelial cells derived from a renal adenocarcinoma).

1.2 Test Principle

The test is a cell test based on the principle of enzyme complementation, the enzyme used herein being beta-galactosidase. HEKEA cells are HEK cells stably expressing, and restricted in their nucleus, mutant beta-galactosidase (omega fragment, also known as EA) (line sold by DiscoverX). This construct makes it possible to obtain beta-galactosidase activity only when the protein comprising the Prolabel complementation fragment has migrated into the nucleus.

The protein of interest comprising the Prolabel fragment is in this case an HIF1-alpha or HIF1-alpha mutated at the two prolines 402 and 564 replaced with alanines, is C-terminal fused via molecular biology (DiscoverX vector sold by Clontech) with the small complementation peptide fragment (Prolabel or ED, about 4 kDa). The vector coding for the chimeric protein HIF1-alpha_Prolabel is then transfected into HEKEA cells to obtain stable clones (HEKEA_HIF1-alphaPLBL).

The amount of C-terminal Prolabel-"labelled" HIF1-alpha protein obtained after treating the cells to hypoxia or compounds that are potentially HIF activators is measured by adding to the cells a lysis buffer containing a chemiluminescent substrate for beta-galactosidase.

The measurement of the beta-galactosidase activity will be proportional to the amount of Prolabel and thus of HIF1-alpha that has migrated into the nucleus of the cells.

Experiments were performed internally in parallel to confirm that the Prolabel fragment alone was not stable in the cells and thus did not allow any activity to be measured.

1.3 Protocol 1.3.1 Experiment Plan
1) Inoculation of the cells on D0
2) Adherence for 24 hours under normoxia
3) Preparation and addition of the products (Biomek 2000 and FX) on D+1
4) Incubation under normoxia for 6 hours
5) Reading of the plates (by luminescence)

1.3.2 Inoculation of the Cells

The cells are inoculated with Multidrop in white, opaque-bottomed 384-well plates (Greiner ref 3704), in 30 µl of culture medium (1% FCS) at 10 000 cells/well (cell plate).

1.3.3 Treatment

Preparation of the Dilution Plate (DL Plate)

The test products are prepared at $3\times10^{-2}$ M in 100% DMSO and then diluted to $3\times10^{-4}$ M in medium containing 0.1% FCS (10 µl in 990 µl of MEM). They are then deposited by hand into column 12 of a round-bottomed 96-well plate (200 µl of each compound) known as the dilution plate (dl). The complete DL plate of $3\times10^{-4}$ M to $10^{-9}$ M is then prepared with Biomek 2000 (programme: range of 10 points in series). For the references and controls, 100 µl of DMEM containing 0.1% FCS are added to column 1, 100 µl of Deferoxamine $10^{-3}$M to column 2, wells A B C D and 100 µl of Deferoxamine $5\times10^{-3}$ M to column 2, wells E F G H.

DL Plate Distribution in Cell Plates 3.3 µL are taken from the DL plate by pipetting with a Biomek FX 96 and placed in horizontal duplicate (columns 1 to 24) in each 384-well cell plate (HEKEA_HIF1-alphaPLBL cell plate).

The cells are then placed for 6 hours in an incubator at 37° C. (ambient $O_2$, 6% $CO_2$).

1.3.4 Measurement of the Beta-Galactosidase Activity.

The kit used is the Prolabel chemiluminescent kit (Ref 93-0001 DiscoverX).

After incubation for 6 hours at 37° C., the cells are lysed with addition of 15 µl of lysis buffer containing the beta-galactosidase substrate (19 volumes of Path hunter cell assay buffer+5 volumes of Emarald II solution+1 volume of Galacton star) directly added to 30 µl of medium in the plate. The plates are incubated for 60 minutes in the absence of light, before reading the luminescence with a Top Count machine. The EC50 values for the compounds are then calculated with appropriate fitting software and given in Table III below.

The activating activity of a compound towards HIF is given by the molar concentration that produces 50% of the maximum response of this same compound.

TABLE III

| Compound No. | EC50 (M) |
| --- | --- |
| 14 | 3.8E−06 |
| 31 | 3.0E−06 |
| 37 | 3.2E−06 |
| 38 | 4.7E−06 |
| 39 | 1.8E−06 |
| 42 | 4.8E−06 |
| 43 | 3.1E−06 |
| 44 | 3.1E−06 |
| 46 | 9.6E−06 |
| 47 | 1.1E−06 |
| 48 | 4.3E−06 |
| 51 | 4.4E−06 |
| 53 | 2.6E−06 |
| 54 | 6.4E−06 |
| 56 | 2.1E−06 |
| 58 | 5.7E−06 |
| 59 | 1.7E−06 |
| 62 | 1.6E−05 |
| 63 | 9.2E−06 |
| 64 | 4.3E−06 |
| 68 | 1.5E−06 |
| 70 | 3.5E−06 |
| 71 | 5.0E−06 |
| 72 | 7.5E−06 |
| 74 | 3.7E−06 |
| 76 | 2.0E−06 |
| 77 | 4.8E−06 |
| 80 | 3.3E−06 |
| 81 | 7.5E−06 |
| 82 | 1.5E−06 |
| 83 | 3.3E−06 |
| 84 | 9.9E−06 |
| 85 | 1.8E−06 |

TABLE III-continued

| Compound No. | EC50 (M) |
|---|---|
| 87 | 9.8E−06 |
| 88 | 8.8E−07 |
| 92 | 8.6E−07 |
| 93 | 3.5E−07 |
| 98B | 2.5E−06 |

1.4 Annex 1.4.1. Maintenance of the HEKEA HIF1-Alpha PLBL Cells.

The cells are cultured in whole medium (cf. below) in a Flask T225 at 37° C. in a $CO_2$ incubator.

1.4.2. Culture Medium for the HEKEA HIF1-Alpha PLBL Cells

| DMEM | 500 mL |
|---|---|
| + FCS 10% (GIBCO 10500-056) | 50 mL |
| + Glutamine (2 mM final) | 5 mL |
| + Penicilllin + streptomycin (200 mg/mL) | 5 mL |
| + Hygromycin B (100 µg/mL) | 1.1 mL |
| + Geneticin (400 µg/mL final) | 4.4 mL |

2. Measurement of the Secretion of VEGF and EPO by Hep3B Hepatocytes 2.1. Object HIF is a transcription factor involved in the adaptation of cells to hypoxia. Since the genes activated by HIF are involved in the adaptive response of cells to hypoxia and of tissues to ischaemia, the object is to identify and characterize compounds that stabilize HIF1-alpha in cells in order to amplify or mimic its beneficial effect. HIF1-alpha was identified following the analysis of the EPO gene promoter, which makes this protein one of the first markers of HIF1-alpha activation. Moreover, VEGF is also identified in the literature as one of the main markers of HIF activation. It is for this reason that measurement of these two proteins was selected for characterizing compounds that are HIF activators in Hep3B cells.

The object was thus to develop a sensitive screening test, adaptable to 96-well plates, for directly measuring the amount of VEGF and EPO in the supernatant of the Hep3B cells (cells derived from a human hepatocarcinoma) in response to the potential HIF activators.

2.2. Test Principle

The test is an ELISA test for measuring VEGF and EPO in the supernatant of Hep3B cells treated under hypoxia or with deferoxamine as controls or with the potential HIF activators. The test was adapted to a 96-well plate, allowing greater compound screening capacity.

2.3. Protocol 2.3.1 Experiment Plan

1) Inoculation of the cells on D0
2) Adherence for 6 hours under normoxia
3) Preparation and addition of the products (Biomek 2000 and FX)
4) Incubation under normoxia for 18 hours
5) EPO and VEGF assay in the supernatant on D+1

2.3.2 Inoculation of the Cells

The cells are subcultured into 100 µl of culture medium (10% FCS) in black, opaque-bottomed 96-well plates (reference Costar 3916) at 30 000 cells/well, with Multidrop.

2.3.3 Treatment of the Cells

Preparation of the Dilution Plate (DL Plate)

The test products are prepared at $10^{-2}$ M in 100% DMSO and then diluted to $3 \times 10^4$ M in medium containing 0.1% FCS (6 µl in 194 µl of MEM). 200 µl of each compound are deposited in column 12 of a 96-well plate. Dilution ranges from $3 \times 10^4$ M to $3 \times 10^{-8}$ M are prepared with Biomek 2000 (programme: range of 9 points in series). 100 µl of MEM 0.1% FCS and Deferoxamine $5 \times 10^{-3}$ M are added as controls to column 3 and, respectively, to wells A,B,C,D and wells E,F,G,H DL Plate Distribution in Cell Plates The medium of the cells inoculated the day before into 96-well plates is changed for 90 µl of medium containing 0.1% FCS and 10 µl are distributed with FX 96 from the 96-well DL plates to the cell plates.

The cell plates thus treated are placed for 18 hours in an incubator at 37° C. (ambient $O_2$, 6% $CO_2$).

2.3.4 EPO and VEGF Assay

The supernatants (80 µl) of the Hep3B cells in the 96-well plates treated with the potential HIF activators are recovered with a multichannel pipette for simultaneous assay of the VEGF and the EPO by ELISA according to the supplier's instructions (Kit EPO Mesoscale (ref K15122B-2)). The EC50 values for EPO and VEGF of the compounds are then calculated with appropriate fitting software and reported in Table IV below.

2.4. Annex

Culture Medium for the Hep3B Cells:

| MEM + Earles (GIBCO 310095) | 500 mL |
|---|---|
| + 10% FCS (GIBCO 10500-056) | 50 mL |
| + Glutamine 2 mM final | 5 mL |
| + 1% non-essential amino acids | 5 mL |

3. Results

The activating activity of a compound with respect to HIF is given by the concentration that produces 50% of the maximum response of this same compound in Table IV below.

TABLE IV

| Compound No. | EC50 EPO (M) | EC50 VEGF (M) |
|---|---|---|
| 14 | 3.0E−07 | — |
| 20 | 1E−06 | 1.1E−06 |
| 31 | 2.1E−06 | — |
| 34 | 9E−07 | — |
| 37 | 1.0E−06 | — |
| 38 | 1.0E−06 | — |
| 39 | 2.0E−06 | — |
| 42 | 1.1E−06 | 1.3E−06 |
| 43 | 1.5E−06 | 1.7E−06 |
| 44 | 1.9E−06 | 2.1E−06 |
| 46 | 7.0E−07 | 1.2E−06 |
| 47 | 2.0E−06 | 2.8E−06 |
| 48 | 1.1E−06 | 1.9E−06 |
| 51 | 3.0E−07 | 4.0E−07 |
| 53 | 9.0E−07 | 3.2E−06 |
| 54 | 4.5E−07 | 3.0E−07 |
| 56 | 2E−06 | 2.5E−06 |
| 58 | 3.2E−06 | 3.6E−06 |
| 59 | 8.1E−07 | 6.8E−07 |
| 62 | 9.0E−07 | 1.0E−06 |
| 64 | 1.4E−06 | 2.4E−06 |
| 68 | 4.0E−07 | 5.0E−07 |
| 70 | 2.7E−06 | 2.9E−06 |
| 71 | 1.6E−06 | 1.6E−06 |
| 72 | 1.0E−06 | 1.7E−06 |
| 74 | 3E−07 | |

TABLE IV-continued

| Compound No. | EC50 EPO (M) | EC50 VEGF (M) |
|---|---|---|
| 76 | 2.0E−07 | 2.0E−07 |
| 77 | 1.4E−06 | 1.3E−06 |
| 80 | 4.0E−07 | 9.0E−07 |
| 81 | 1.2E−06 | 1.9E−06 |
| 82 | 1E−06 | 1.2E−06 |
| 83 | 1.4E−06 | 1.3E−06 |
| 84 | 2.9E−06 | 3.3E−06 |
| 85 | 2.5E−06 | 2.5E−06 |
| 88 | 3.0E−07 | 4.0E−07 |
| 92 | 5.0E−07 | 5.0E−07 |
| 93 | 4.0E−07 | 4.0E−07 |

The compounds according to the invention may thus be used for the preparation of medicaments, in particular medicaments that are activators of the HIF transcription factor.

Thus, according to another of its aspects, a subject of the invention is medicaments that comprise a compound of formula (I), or an addition salt thereof with a pharmaceutically acceptable acid of the compound of formula (I).

The invention also relates to a pharmaceutical composition comprising a compound of formula (I) according to the present invention, or a pharmaceutically acceptable salt of this compound, and also at least one pharmaceutically acceptable excipient.

These medicaments find their therapeutic use especially in treatment/prophylaxis, in particular of cardiovascular diseases, ischaemia of the lower limbs, cardiac insufficiency, coronary diseases of ischaemic origin, for instance angina pectoris or myocardial infarction, arteriosclerosis, strokes of ischaemic origin, pulmonary hypertension and any pathology caused by partial or total vascular occlusion in man and animals.

These medicaments also find their therapeutic use in the treatment/prophylaxis of glaucoma, renal diseases or in cerebral diseases of neurodegenerative origin or otherwise, and anaemia, or a medicament for promoting cicatrization or agents for shortening the post-operative convalescence period or a medicament for treating general fatigue conditions, or a medicament used for the purpose of obtaining blood in the context of autotransfusions necessary following major surgical interventions such as cranial or chest surgery, or cardiac, carotid or aortic operations.

These compounds find their therapeutic use especially in the treatment/prophylaxis of anaemia.

These compounds may also be used in man and animals for the purpose of obtaining blood in the context of autotransfusions necessary following major surgical interventions such as cranial or chest surgery or cardiac, carotid or aortic operations.

These compounds are potentially usable in man and animals as agents for promoting cicatrization or agents for shortening the post-operative convalescence period.

These compounds are potentially usable in man and animals in the treatment of general fatigue conditions ranging up to cachexia appearing in particular in the elderly.

These compounds are potentially usable in man and animals in the treatment of glaucoma, renal diseases or cerebral diseases of neurodegenerative origin or otherwise.

Finally, the compounds described in the invention are potentially usable in man and animals for treating cardiac or peripheral diseases of ischaemic origin via regenerative medicine in autologous and heterologous approaches using non-embryonic stem cells or myoblastic cells for therapeutic purposes, whether as treatment of these cells before administration or as treatment simultaneously with the local administration of these cells.

Moreover, the compounds described in the invention may be used, alone or, if necessary, in combination with one or more other active compounds that are useful in the treatment of hypertension, cardiac insufficiency, diabetes and anaemia.

For example, mention may be made of the combination of a compound according to the invention with one or more compounds chosen from converting enzyme inhibitors, angiotensin II receptor antagonists, beta-blockers, mineralocorticoid receptor antagonists, diuretics, calcium antagonists, statins and digitalin derivatives.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the prophylaxis or treatment of the above disorders or diseases.

The appropriate unit administration forms include oral forms such as tablets, soft or hard gel capsules, powders, granules and oral solutions or suspensions, sublingual, buccal, intratracheal, intraocular, nasal and inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate; such dosages do not depart from the scope of the invention. According to the usual practice, the dosage that is appropriate to each patient is determined by the doctor according to the mode of administration and the weight and response of the said patient.

According to another of its aspects, the present invention also relates to a method for treating the pathologies indicated above, which comprises the administration, to patient, of an effective dose of a compound according to the invention, or a pharmaceutically acceptable salt thereof.

We claim:
1. A compound of formula (I):

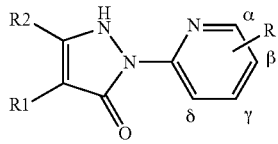

wherein
R represents —SO₂—NR3R4 or —SO₂—R4; R3 and R4 being as defined below;
R1 represents —W-aryl, the said aryl being optionally substituted on at least one carbon atom with at least one substituent chosen from halogen, (C1-C5)alkyl, —(C1-C5)alkylene-O—(C1-C5)alkyl, —(C1-C5)alkoxy, hydroxy, -halo(C1-C5)alkyl, cyano, —O(C1-C5)alkylene-O—(C1-C5)alkyl, —O—(C1-C5)alkylene-NR5R6, —SO₂—(C1-C5)alkyl, —NR5R6 and —CO₂R5,
R2 represents hydrogen, —(C1-C5)alkyl, —(C1-C5)alkylene-O—(C1-C5)alkyl, -halo(C1-C5)alkyl, —W—COOR5, —W—C(O)NHR5 or —W—C(O)—NR5R6; W, R5 and R6 being as defined below;
it being understood that:
n represents 0, 1 or 2;
W is
 (i) —(C1-C5)alkylene-, optionally substituted with a group chosen from —(CH₂)n-CO₂R5 and —(CH₂)n-(CO)NR5R6, with n as defined above and R5 and R6 as defined below; or
 (ii) —(C3-C6)cycloalkylene-,
R3 and R4 which may be identical or different, represent, independently of each other, hydrogen, —(C1-C5)alkyl, —(C3-C6)cycloalkyl, —(C1-C5)alkylene-O—(C1-C5)alkyl, aryl, —CH₂-aryl, —W—OH, —W—CHOH—CH₂OH, —W—CO₂R5, —W—NR5R6 or —W—O—(CH₂)n-aryl;
 the said —(C3-C6)cycloalkyl being optionally substituted
  on at least one carbon atom with at least one group chosen from —(C1-C5)alkyl, —(C1-C5)alkoxy, hydroxy, —W—NR5R6 and —W—CO₂R5,
 with W and n as defined previously and R5 and R6 as defined below and provided that when R3 and R4 are identical, they cannot be hydrogen; and
R5 and R6, which may be identical or different, represent, independently of each other, hydrogen, —(C1-C5)alkyl or —(C1-C5)haloalkyl,
in the form of the base or an acid-addition salt.

2. The compound according to claim 1, wherein R represents —SO₂—NR3R4; in the form of the base or an acid-addition salt.

3. The compound according to claim 1, wherein R represents —SO₂—R4; in the form of the base or an acid-addition salt.

4. The compound according to claim 1, wherein R is a substituent of the atom in the β position of pyridine; in the form of the base or an acid-addition salt.

5. The compound according to claim 1, wherein W is (C1-C5)alkylene or (C3-C6)cycloalkylene; in the form of the base or an acid-addition salt.

6. The compound according to claim 5, wherein the said aryl represents phenyl; in the form of the base or an acid-addition salt.

7. The compound according to claim 1, wherein R represents —SO₂—NR3R4; R2 represents hydrogen or —(C1-C5)alkyl; in the form of the base or an acid-addition salt.

8. The compound according to claim 7, wherein R1 represents methyl; W represents —CH₂—; and the said aryl represents phenyl; in the form of the base or an acid-addition salt.

9. The compound according to claim 1, which is:
 6-[4-(2-chlorobenzyl)-3-methyl-5-oxo-2,5-dihydro-1H-pyrazol-1-yl]-N,N-diethylpyridine-3-sulfonamide;
 6-[4-(2-chlorobenzyl)-3-methyl-5-oxo-2,5-dihydro-1H-pyrazol-1-yl]-N-ethyl-N-phenylpyridine-3-sulfonamide;
 6-[4-(2-chlorobenzyl)-3-methyl-5-oxo-2,5-dihydro-1H-pyrazol-1-yl]-N,N-di(propan-2-yl)pyridine-3-sulfonamide;
 N,N-diethyl-6-[4-(2-fluorobenzyl)-3-methyl-5-oxo-2,5-dihydro-1H-pyrazol-1-yl]pyridine-3-sulfonamide;
 N-ethyl-6-[4-(2-fluorobenzyl)-3-methyl-5-oxo-2,5-dihydro-1H-pyrazol-1-yl]-N-phenylpyridine-3-sulfonamide;
 6-[4-(2,4-dichlorobenzyl)-3-methyl-5-oxo-2,5-dihydro-1H-pyrazol-1-yl]-N-ethyl-N-phenylpyridine-3-sulfonamide;
 6-[4-(2,4-dichlorobenzyl)-3-methyl-5-oxo-2,5-dihydro-1H-pyrazol-1-yl]-N,N-di(propan-2-yl)pyridine-3-sulfonamide;
 6-[4-(2-chloro-6-fluorobenzyl)-3-methyl-5-oxo-2,5-dihydro-1H-pyrazol-1-yl]-N,N-diethylpyridine-3-sulfonamide;
 6-[4-(2-chloro-6-fluorobenzyl)-3-methyl-5-oxo-2,5-dihydro-1H-pyrazol-1-yl]-N-ethyl-N-phenylpyridine-3-sulfonamide;
 6-[4-(2-chloro-6-fluorobenzyl)-3-methyl-5-oxo-2,5-dihydro-1H-pyrazol-1-yl]-N,N-di(propan-2-yl)pyridine-3-sulfonamide;
 6-[4-(4-chlorobenzyl)-3-methyl-5-oxo-2,5-dihydro-1H-pyrazol-1-yl]-N,N-diethylpyridine-3-sulfonamide;
 6-[4-(4-chlorobenzyl)-3-methyl-5-oxo-2,5-dihydro-1H-pyrazol-1-yl]-N-ethyl-N-phenylpyridine-3-sulfonamide;
 6-[4-(4-chlorobenzyl)-3-methyl-5-oxo-2,5-dihydro-1H-pyrazol-1-yl]-N,N-di(propan-2-yl)pyridine-3-sulfonamide;
 6-[4-(2-fluorobenzyl)-3-methyl-5-oxo-2,5-dihydro-1H-pyrazol-1-yl]-N,N-di(propan-2-yl)pyridine-3-sulfonamide;
 N-ethyl-6-{4-[4-(methoxymethyl)benzyl]-3-methyl-5-oxo-2,5-dihydro-1H-pyrazol-1-yl}-N-phenylpyridine-3-sulfonamide;
 N-ethyl-6-{4-[3-(methoxymethyl)benzyl]-3-methyl-5-oxo-2,5-dihydro-1H-pyrazol-1-yl}-N-phenylpyridine-3-sulfonamide;
 6-[4-(3-cyanobenzyl)-3-methyl-5-oxo-2,5-dihydro-1H-pyrazol-1-yl]-N-ethyl-N-phenylpyridine-3-sulfonamide;
 6-[4-(4-cyanobenzyl)-3-methyl-5-oxo-2,5-dihydro-1H-pyrazol-1-yl]-N-ethyl-N-phenylpyridine-3-sulfonamide;
 6-[4-(2-cyanobenzyl)-3-methyl-5-oxo-2,5-dihydro-1H-pyrazol-1-yl]-N-ethyl-N-phenylpyridine-3-sulfonamide;
 N-ethyl-6-{4-[3-(2-methoxyethoxy)benzyl]-3-methyl-5-oxo-2,5-dihydro-1H-pyrazol-1-yl}-N-phenylpyridine-3-sulfonamide;

N-ethyl-6-{3-methyl-4-[4-(methylsulfonyl)benzyl]-5-oxo-2,5-dihydro-1H-pyrazol-1-yl}-N-phenylpyridine-3-sulfonamide;
6-(4-benzyl-3-methyl-5-oxo-2,5-dihydro-1H-pyrozol-1-yl)-N-ethyl-N-phenylpyridine-3-sulfonamide;
6-[4-(2,5-dimethoxybenzyl)-3-methyl-5-oxo-2,5-dihydro-1H-pyrazol-1-yl]-N-ethyl-N-phenylpyridine-3-sulfonamide;
N-ethyl-6-{3-methyl-5-oxo-4-[4-(trifluoromethyl)benzyl]-2,5-dihydro-1H-pyrazol-1-yl}-N-phenylpyridine-3-sulfonamide;
N-ethyl-6-{3-methyl-5-oxo-4-[3-(trifluoromethyl)benzyl]-2,5-dihydro-1H-pyrazol-1-yl}-N-phenylpyridine-3-sulfonamide;
6-[4-(3,5-dimethoxybenzyl)-3-methyl-5-oxo-2,5-dihydro-1H-pyrazol-1-yl]-N-ethyl-N-phenylpyridine-3-sulfonamide;
N-ethyl-6-[4-(4-hydroxybenzyl)-3-methyl-5-oxo-2,5-dihydro-1H-pyrazol-1-yl]-N-phenylpyridine-3-sulfonamide;
6-(4-{4-[2-(dimethylamino)ethoxy]benzy}-3-methyl-5-oxo-2,5-dihydro-1H-pyrazol-1-yl)-N-ethyl-N-phenylpyridine-3-sulfonamide;
6-{4-[4-(dimethylamino)benzyl]-3-methyl-5-oxo-2,5-dihydro-1H-pyrazol-1-yl}-N-ethyl-N-phenylpyridine-3-sulfonamide;
N-ethyl-6-{3-methyl-5-oxo-4-[2-(trifluoromethyl)benzyl]-2,5-dihydro-1H-pyrazol-1-yl}-N-phenylpyridine-3-sulfonamide;
6-(4-benzyl-3-methyl-5-oxo-2,5-dihydro-1H-pyrazol-1-yl)-N-(3-methylbutyl)pyridine-3-sulfonamide;
6-{4-[3-(dimethylamino)benzyl]-3-methyl-5-oxo-2,5-dihydro-1H-pyrazol-1-yl}-N-ethyl-N-phenylpyridine-3-sulfonamide;
N-ethyl-6-[4-(4-methoxybenzyl)-3-methyl-5-oxo-2,5-dihydro-1H-pyrazol-1-yl]-N-phenylpyridine-3-sulfonamide;
N-ethyl-6-[4-(3-methoxybenzyl)-3-methyl-5-oxo-2,5-dihydro-1H-pyrazol-1-yl]-N-phenylpyridine-3-sulfonamide;
6-(4-{3-[2-(dimethylamino)ethoxy]benzy}-3-methyl-5-oxo-2,5-dihydro-1H-pyrazol-1-yl)-N-ethyl-N-phenylpyridine-3-sulfonamide;
N-ethyl-6-[4-(2-methoxybenzyl)-3-methyl-5-oxo-2,5-dihydro-1H-pyrazol-1-yl]-N-phenylpyridine-3-sulfonamide;
N-ethyl-6-[4-(3-hydroxybenzyl)-3-methyl-5-oxo-2,5-dihydro-1H-pyrazol-1-yl]-N-phenylpyridine-3-sulfonamide;
6-(4-benzyl-3-ethyl-5-oxo-2,5-dihydro-1H-pyrazol-1-yl)-N-ethyl-N-phenylpyridine-3-sulfonamide;
N-ethyl-6-{4-[4-(2-methoxyethoxy)benzyl]-3-methyl-5-oxo-2,5-dihydro-1H-pyrazol-1-yl}-N-phenylpyridine-3-sulfonamide;
6-(4-benzyl-5-oxo-3-propyl-2,5-dihydro-1H-pyrazol-1-yl)-N-ethyl-N-phenylpyridine-3-sulfonamide hydrochloride;
N-ethyl-6-[3-methyl-5-oxo-4-(2-phenylethyl)-2,5-dihydro-1H-pyrazol-1-yl]-N-phenylpyridine-3-sulfonamide;
N-ethyl-6-[3-methyl-5-oxo-4-(2-phenylpropan-2-yl)-2,5-dihydro-1H-pyrazol-1-yl]-N-phenylpyridine-3-sulfonamide;
N-ethyl-6-[3-methyl-5-oxo-4-(1-phenylcyclopropyl)-2,5-dihydro-1H-pyrazol-1-yl]-N-phenylpyridine-3-sulfonamide;
6-[4-benzyl-3-(methoxymethyl)-5-oxo-2,5-dihydro-1H-pyrazol-1-yl]-N-ethyl-N-phenylpyridine-3-sulfonamide;
6-[4-benzyl-5-oxo-3-(trifluoromethyl)-2,5-dihydro-1H-pyrazol-1-yl]-N-ethyl-N-phenylpyridine-3-sulfonamide;
6-[4-benzyl-3-(2-methylpropyl)-5-oxo-2,5-dihydro-1H-pyrazol-1-yl]-N-ethyl-N-phenylpyridine-3-sulfonamide;
N-ethyl-6-[3-methyl-5-oxo-4-(3-phenylpropyl)-2,5-dihydro-1H-pyrazol-1-yl]-N-phenylpyridine-3-sulfonamide;
6-(4-benzyl-5-oxo-2,5-dihydro-1H-pyrazol-1-yl)-N-ethyl-N-phenylpyridine-3-sulfonamide;
6-(4-benzyl-5-oxo-2,5-dihydro-1H-pyrazol-1-yl)-N-tert-butyl-N-methylpyridine-3-sulfonamide;
(2-{5-[ethyl(phenyl)sulfamoyl]pyridin-2-yl}-3-oxo-2,3-dihydro-1H-pyrazol-4-yl)acetic acid;
2-(2-{5-[ethyl(phenyl)sulfamoyl]pyridin-2-yl}-3-oxo-2,3-dihydro-1H-pyrazol-4-yl)-N,N-dimethylacetamide;
methyl (2-{5-[ethyl(phenyl)sulfamoyl]pyridin-2-yl}-3-oxo-2,3-dihydro-1H-pyrazol-4-yl)acetate;
ethyl (4-benzyl-1-{5-[ethyl(phenyl)sulfamoyl]pyridin-2-yl}-5-oxo-2,5-dihydro-1H-pyrazol-3-yl)acetate;
2-(2-{5-[ethyl(phenyl)sulfamoyl]pyridin-2-yl}-3-oxo-2,3-dihydro-1H-pyrazol-4-yl)-N-methylacetamide;
2-(4-benzyl-1-{5-[ethyl(phenyl)sulfamoyl]pyridin-2-yl}-5-oxo-2,5-dihydro-1H-pyrazol-3-yl)-N,N-dimethylacetamide;
3-(2-{5-[ethyl(phenyl)sulfamoyl]pyridin-2-yl}-3-oxo-2,3-dihydro-1H-pyrazol-4-yl)propanoic acid;
methyl 3-[(2-{5-[ethyl(phenyl)sulfamoyl]pyridin-2-yl}-5-methyl-3-oxo-2,3-dihydro-1H-pyrazol-4-yl)methyl]benzoate;
methyl 3-(2-{5-[ethyl(phenyl)sulfamoyl]pyridin-2-yl}-3-oxo-2,3-dihydro-1H-pyrazol-4-yl)propanoate;
methyl {2-[5-(tert-butylsulfamoyl)pyridin-2-yl]-3-oxo-2,3-dihydro-1H-pyrazol-4-yl}(phenyl)acetate;
methyl 2-[(2-{5-[ethyl(phenyl)sulfamoyl]pyridin-2-yl}-5-methyl-3-oxo-2,3-dihydro-1H-pyrazol-4-yl)methyl]benzoate;
2-[(1-{5-[ethyl(phenyl)sulfamoyl]pyridin-2-yl}-3-methyl-5-oxido-1H-pyrazol-4-yl)methyl]benzoate;
methyl 3-(2-{5-[cyclopentyl(methyl)sulfamoyl]pyridin-2-yl}-3-oxo-2,3-dihydro-1H-pyrazol-4-yl)-3-phenylpropanoate;
6-(4-benzyl-5-oxo-2,5-dihydro-1H-pyrazol-1-yl)-N-[2-(benzyloxy)ethyl]-N-cyclopentylpyridine-3-sulfonamide;
6-(4-benzyl-5-oxo-2,5-dihydro-1H-pyrazol-1-yl)-N-[3-(benzyloxy)propyl]-N-cyclopentylpyridine-3-sulfonamide;
6-(4-benzyl-5-oxo-2,5-dihydro-1H-pyrazol-1-yl)-N-cyclopentyl-N-(3-hydroxypropyl)pyridine-3-sulfonamide;
6-(4-benzyl-5-oxo-2,5-dihydro-1H-pyrazol-1-yl)-N-cyclopentyl-N-(2-hydroxyethyl)pyridine-3-sulfonamide;
6-(4-benzyl-5-oxo-2,5-dihydro-1H-pyrazol-1-yl)-N-cyclopentyl-N-(2,3-dihydroxypropyl)pyridine-3-sulfonamide;
6-(4-benzyl-5-oxo-2,5-dihydro-1H-pyrazol-1-yl)-N-cyclopentyl-N-[2-(dimethylamino)ethyl]pyridine-3-sulfonamide;
6-[4-(cyclopentylmethyl)-5-oxo-2,5-dihydro-1H-pyrazol-1-yl]-N-ethyl-N-phenylpyridine-3-sulfonamide;

6-(4-benzyl-5-oxo-2,5-dihydro-1H-pyrazol-1-yl)-N-[(R1R,3S)-3-(hydroxymethyl)yclopentyl]-N-methylpyridine-3-sulfonamide;

6-(4-benzyl-5-oxo-2,5-dihydro-1H-pyrazol-1-yl)-N-(2-methoxy-2-methylpropyl)pyridine-3-sulfonamide;

6-(4-benzyl-5-oxo-2,5-dihydro-1H-pyrazol-1-yl)-N-cyclopentyl-N-[(2R)-2,3-dihydroxypropyl]pyridine-3-sulfonamide;

6-(4-benzyl-5-oxo-2,5-dihydro-1H-pyrazol-1-yl)-N-(2,3-dihydroxypropyl)-N-phenylpyridine-3-sulfonamide;

3-(2-{5-[cyclopentyl(methyl)sulfamoyl]pyridin-2-yl}-3-oxo-2,3-dihydro-1H-pyrazol-4-yl)-3-phenyl-N-(2,2,2-trifluoroethyl)propanamide;

6-(4-benzyl-5-oxo-2,5-dihydro-1H-pyrazol-1-yl)-N-cyclopentyl-N-[3-hydroxy-2-(hydroxymethyl)propyl]pyridine-3-sulfonamide;

6-(4-benzyl-5-oxo-2,5-dihydro-1H-pyrazol-1-yl)-N-cyclopentyl-N-[(2S)-2,3-dihydroxypropyl]pyridine-3-sulfonamide;

6-(4-benzyl-5-oxo-2,5-dihydro-1H-pyrazol-1-yl)-N-[(1S,2S)-2-hydroxycyclopentyl]pyridine-3-sulfonamide;

6-(4-benzyl-5-oxo-2,5-dihydro-1H-pyrazol-1-yl)-N-[1-(dimethylamino)-2-methylpropan-2-yl]pyridine-3-sulfonamide;

6-(4-benzyl-5-oxo-2,5-dihydro-1H-pyrazol-1-yl)-N-methyl-N-phenylpyridine-3-sulfonamide;

ethyl 3-{2-[5-(tert-butylsulfamoyl)pyridin-2-yl]-3-oxo-2,3-dihydro-1H-pyrazol-4-yl}-3-phenylpropanoate;

6-(4-benzyl-5-oxo-2,5-dihydro-1H-pyrazol-1-yl)-N-tert-butyl-N-(2,3-dihydroxypropyl)pyridine-3-sulfonamide;

6-(4-benzyl-5-oxo-2,5-dihydro-1H-pyrazol-1-yl)-N-(2-hydroxyethyl)pyridine-3-sulfonamide;

6-(4-benzyl-5-oxo-2,5-dihydro-1H-pyrazol-1-yl)-N-cyclopentyl-N-[3-(dimethylamino)propyl]pyridine-3-sulfonamide hydrochloride; or 6-(4-benzyl-5-oxo-2,5-dihydro-1H-pyrazol-1-yl)-N-cyclopentyl-N-[3-(dimethylamino)propyl]pyridine-3-sulfonamide hydrochloride;

in the form of the base or an acid-addition salt.

10. A pharmaceutical composition comprising the compound according to claim 1 or an acid-addition salt thereof, and at least one pharmaceutically acceptable excipient.

\* \* \* \* \*